US008124341B2

(12) United States Patent
Nakamura et al.

(10) Patent No.: US 8,124,341 B2
(45) Date of Patent: Feb. 28, 2012

(54) GENES AND POLYPEPTIDES RELATING TO HEPATOCELLULAR OR COLORECTAL CARCINOMA

(75) Inventors: Yusuke Nakamura, Tokyo (JP); Yoichi Furukawa, Tokyo (JP)

(73) Assignee: Oncotherapy Science, Inc., Kanagawa (JP)

( * ) Notice: Subject to any disclaimer, the term of this patent is extended or adjusted under 35 U.S.C. 154(b) by 3 days.

(21) Appl. No.: 12/699,711

(22) Filed: Feb. 3, 2010

(65) Prior Publication Data

US 2010/0291567 A1    Nov. 18, 2010

Related U.S. Application Data

(60) Division of application No. 11/948,790, filed on Nov. 30, 2007, now abandoned, which is a continuation of application No. 10/517,151, filed as application No. PCT/JP03/07070 on Jun. 4, 2003, now abandoned.

(60) Provisional application No. 60/386,985, filed on Jun. 6, 2002.

(51) Int. Cl.
*C12Q 1/68* (2006.01)
*G01N 33/53* (2006.01)

(52) U.S. Cl. .......................................... 435/6.1; 435/7.1

(58) Field of Classification Search ........................ None
See application file for complete search history.

(56) References Cited

U.S. PATENT DOCUMENTS

| | | | |
|---|---|---|---|
| 6,908,748 B2 | 6/2005 | Ota et al. | |
| 7,279,558 B2 | 10/2007 | Ota et al. | |
| 7,425,612 B2 | 9/2008 | Nakamura et al. | |
| 7,705,141 B2 | 4/2010 | Nakamura et al. | |
| 7,847,065 B2 | 12/2010 | Nakamura et al. | |
| 2003/0017480 A1 | 1/2003 | Ota et al. | |
| 2003/0082776 A1 | 5/2003 | Ota et al. | |
| 2005/0250144 A1 | 11/2005 | Ota et al. | |
| 2007/0105122 A1 | 5/2007 | Ota et al. | |
| 2008/0069826 A1 | 3/2008 | Ota et al. | |

FOREIGN PATENT DOCUMENTS

| | | |
|---|---|---|
| WO | WO 00/00610 A2 | 1/2000 |
| WO | WO 00/50588 A2 | 8/2000 |
| WO | WO 00/50588 A3 | 8/2000 |
| WO | WO 01/09318 A1 | 2/2001 |
| WO | WO 01/40466 A2 | 6/2001 |
| WO | WO 01/85775 A1 | 11/2001 |

OTHER PUBLICATIONS

Nolte et al (J Clin Pathol, 1998, 51(1): 47-51).*
Database; EMBL Accession No. AQ045454, "RPCI11-33A11.TJ RPCI-11 *Homo sapiens* genomic clone RPCI-11-33A11, genomic survey sequence", Jul. 14, 1998.
Database; EMBL Accession No. BE348232, "hw21a07.x1 NCI_CGAP_Kid11 *Homo sapiens* cDNA clone IMAGE:3183540 3' similar to WP:K07A1.11 CE11860 RBA-1: Hypothetical 46.7 KD TRP-ASP Repeats Containing Protein K07A1.11 In Chromosome I, mRNA sequence", Jul. 21, 2000.
Database; EMBL Accession No. AK074435, "*Homo sapiens* cDNA FLJ23855 fis, clone LNG06370", Feb. 15, 2002.
Database; EMBL Accession No. BC025392, "*Homo sapiens* hypothetical protein LOC146845, mRNA (cDNA clone MGC:26645 Image:4838276), complete cds", Mar. 12, 2002.
sequence comparison of Seq ID No:254 with instant SEQ ID No. 8, Feb. 3, 2010.
Bienz, Mariann and Hans Clevers; "Linking colorectal cancer to Wnt signaling"; *Cell* 103:311-320 (Oct. 13, 2000).
Brabletz, Thomas et al.; "β-catenin regulates the expression fo the matrix metalloproteinase-7 in human colorectal cancer"; *Am. J. Pathol.* 155(4):1033-1038 (Oct. 1999).
Bullions, Linda C., M.D. and Arnold J. Levine, M.D.; "The role of beta-catenin in cell adhesion, signal transduction, and cancer"; *Current Opinion in Oncology* 10:81-87 (1998).
Crawford, Howard C. et al.; "The metalloproteinase matrilysin is a target of β-catenin transactivation in intestinal tumors"; *Oncogene* 18:2883-2891 (1999).
He Tong-Chuan et al.; "Identification of c-*MYC* as a target of the APC pathway"; *Science* 281:1509-1512 (Sep. 4, 1998).
Korinek, Vladimir et al.; "Constitutive transcriptional activation by a β-catenin-Tcf complex APC$^{-/-}$ colon carcinoma"; *Science* 275:1784-1787 (Mar. 21, 1997).
Mann, B. et al.; "Target genes of β-catenin-T cell-factor/lymphoid-enhancer-factor signaling in human colorectal carcinomas"; *Proc. Natl. Acad. Sci. U.S.A.* 96:1603-1608 (Feb. 1999).
Polakis, Paul; "Wnt signaling and cancer"; *Genes and Development* 14:1837-1851 (2000).
Shtutman, Michael et al.; "The cyclin D1 gene is a target of the β-catenin/LEF-1 pathway"; *Proc. Natl. Acad. Sci. U.S.A.* 96:5522-5527 (May 1999).
Takahashi, Meiko et al.; "Identification and characterization of a gene down-regulated by transfer of wild-type APC"; In: *Proceedings of the 61st Annual Meeting of the Japanese Cancer Society*; *Jpn. J. Cancer Res.* 93(Supplement):69, Abstract 2553, Oct. 1-3, 2002, Tokyo.
Takahashi, Meiko et al.; "Isolation of a novel human gene, *APCDD1*, as a direct target of the β-catenin/T-cell factor 4 complex with probable involvement in colorectal carcinogenesis"; *Cancer Research* 62:5651-5656 (Oct. 15, 2002).
Tockman, M.S. et al.; "Considerations in bringing a cancer biomarker to clinical application"; *Cancer Research* SUPPL. 52:2711s-2718s (May 1, 1992).
Van Der Heyden, Marcel A. G. et al.; "Identification of connexin43 as a functional target for Wnt signaling"; *Journal of Cell Science* 111:1741-1749 (1998).
Wielenga, Vera J. M. et al.; "Expression of CD44 in *Apc* and *Tcf* mutant mice implies regulation by the WNT pathway"; *American Journal of Pathology* 154(2):515-523 (Feb. 1999).
Wodarz, Andreas and Roel Nusse; "Mechanisms of Wnt signaling in development"; *Annu. Rev. Cell Dev. Biol.* 14:59-88 (1998).
U.S. Appl. No. 12/910,015, filed Oct. 22, 2010, 142 pgs.

(Continued)

*Primary Examiner* — Sean Aeder
(74) *Attorney, Agent, or Firm* — Kilpatrick Townsend & Stockton LLP

(57) ABSTRACT

The present application provides novel human genes WDRPUH and KRZFPUH, and PPIL1 whose expression is markedly elevated in a great majority of HCCs and colorectal cancers, respectively, compared to corresponding non-cancerous tissues, as well as novel human gene APCDD1 whose expression is elevated in primary colon cancers and down-regulated in response to the transduction of wild-type APC1 into colon-cancer cells. The genes and polypeptides encoded by the genes can be used, for example, in the diagnosis of a cell proliferative disease, and as target molecules for developing drugs against the disease.

1 Claim, 36 Drawing Sheets

OTHER PUBLICATIONS

Silva, F., et al., "Identification of *WDRPUH*, a novel gene abundantly expressed in human hepatocellular carcinomas as a molecular target for diagnosis and treatment," *Proceedings of the American Association for Cancer Research*, vol. 45, p. 395, Abstract #1717 (Mar. 2004).

Silva, F., et al., "WDRPUH, A Novel WD-Repeat—Containing Protein, Is Highly Expressed in Human Hepatocellular Carcinoma and Involved in cell Proliferation," *Neoplasia*, vol. 7(4), pp. 348-355 (Apr. 2005).

Silva, F., et al., "WDRPUH, a novel WD-Repeat protein highly expressed in hepatocellular carcinoma, is involved in proliferation of cancer cells," *Proceedings of the American Association for Cancer Research*, vol. 46, pp. 548-549, Abstract #2337 (Apr. 2005).

Silva, F., et al., "Identification of a novel molecular target gene, *WDRPUH*, abundantly expressed in human hepatocellular carcinoma," *Proceedings 62$^{nd}$ Annual Meeting of the Japanese Cancer Association*, p. 284, Abstract #3327-OP (Aug. 25, 2005).

U.S. Appl. No. 13/132,891, which is a U.S. National Phase of PCT/JP2009/006573 filed Dec. 3, 2009, 53 pages.

\* cited by examiner a b pcDNA3.1myc/His-WDRPUH

FITC (anti-Myc)     DAPI     Merge a b a b a pcDNA-antisense    pcDNA-KRZFPUH b

A

Semiquantitative RT-PCR

Huh7

KRZFPUH
GAPDH

Mock    EGFP    Si-02

B

MTT Assay at day5

Huh7

C

MTT Assay at day 10

Huh7

D

Giemsa Staining

Huh7

Mock            EGFP            Si-02 a b a
NIH3T3 b
HCT116

A

B a b c a b a pcDNA     pcDNA-APCDD1     pcDNA-antisense b

APCDD1

A

Rhodamine    DAPI    Merge

B

Rhodamine    DAPI    Merge

A

B

SEQUENCE LISTING

```
<160> NUMBER OF SEQ ID NOS: 111

<210> SEQ ID NO 1
<211> LENGTH: 2152
<212> TYPE: DNA
<213> ORGANISM: Homo sapiens
<220> FEATURE:
<221> NAME/KEY: CDS
<222> LOCATION: (35)..(1897)
<223> OTHER INFORMATION:

<400> SEQUENCE: 1
agcgggagag caaagtaatc agaacctccc aagg atg gat aac aaa att tcg ccg        55
                                    Met Asp Asn Lys Ile Ser Pro
                                    1               5 gag gcc caa gtg gcg gag ctg gaa ctt gac gcc gtg atc ggc ttc aat         103
Glu Ala Gln Val Ala Glu Leu Glu Leu Asp Ala Val Ile Gly Phe Asn
        10                  15                  20 gga cat gtg ccc act ggt ctc aaa tgc cat cct gac cag gag cat atg         151
Gly His Val Pro Thr Gly Leu Lys Cys His Pro Asp Gln Glu His Met
    25                  30                  35 att tat cct ctt ggt tgc aca gtc ctc att cag gca ata aat act aaa         199
Ile Tyr Pro Leu Gly Cys Thr Val Leu Ile Gln Ala Ile Asn Thr Lys
40                  45                  50                  55 gag cag aac ttc cta cag ggt cat ggc aac aac gtc tcc tgc ttg gcc         247
Glu Gln Asn Phe Leu Gln Gly His Gly Asn Asn Val Ser Cys Leu Ala
                60                  65                  70 atc tcc agg tct gga gag tac atc gcc tcc gga caa gtc aca ttc atg         295
Ile Ser Arg Ser Gly Glu Tyr Ile Ala Ser Gly Gln Val Thr Phe Met
            75                  80                  85 ggg ttc aag gca gac atc att ttg tgg gat tat aag aac aga gag ctg         343
Gly Phe Lys Ala Asp Ile Ile Leu Trp Asp Tyr Lys Asn Arg Glu Leu
        90                  95                  100 ctt gct cgg ctg tcc ctt cac aaa ggc aaa att gaa gct ctg gcc ttt         391
Leu Ala Arg Leu Ser Leu His Lys Gly Lys Ile Glu Ala Leu Ala Phe
    105                 110                 115 tct cca aat gat ttg tac ttg gta tca cta gga ggc cca gat gac gga         439
Ser Pro Asn Asp Leu Tyr Leu Val Ser Leu Gly Gly Pro Asp Asp Gly
```

```
            120             125             130             135
agt gtg gtg gtg tgg agc ata gcc aag aga gat gcc atc tgt ggc agc        487
Ser Val Val Val Trp Ser Ile Ala Lys Arg Asp Ala Ile Cys Gly Ser
                140             145             150 cct gca gcc ggc ctc aat gtt ggc aat gcc acc aat gtg atc ttc tcc        535
Pro Ala Ala Gly Leu Asn Val Gly Asn Ala Thr Asn Val Ile Phe Ser
                155             160             165 agg tgc cgg gat gag atg ttt atg act gct gga aat ggg aca att cga        583
Arg Cys Arg Asp Glu Met Phe Met Thr Ala Gly Asn Gly Thr Ile Arg
                170             175             180 gta tgg gaa ttg gat ctt cca aat aga aaa atc tgg cca act gag tgc        631
Val Trp Glu Leu Asp Leu Pro Asn Arg Lys Ile Trp Pro Thr Glu Cys
                185             190             195 caa aca gga cag ttg aaa aga ata gtc atg agt att gga gtg gat gat        679
Gln Thr Gly Gln Leu Lys Arg Ile Val Met Ser Ile Gly Val Asp Asp
200             205             210             215 gat gat agc ttt ttc tac ctt ggc acc acg act gga gat att cta aaa        727
Asp Asp Ser Phe Phe Tyr Leu Gly Thr Thr Thr Gly Asp Ile Leu Lys
                220             225             230 atg aac ccc agg act aaa ctg ctg aca gat gtt ggg cct gcg aag gac        775
Met Asn Pro Arg Thr Lys Leu Leu Thr Asp Val Gly Pro Ala Lys Asp
                235             240             245 aaa ttc agt ttg gga gtg tca gct atc agg tgc ctg aag atg ggg ggt        823
Lys Phe Ser Leu Gly Val Ser Ala Ile Arg Cys Leu Lys Met Gly Gly
                250             255             260 ttg ttg gtg ggc tct gga gcc gga ctg ctg gtc ttc tgt aaa agc cct        871
Leu Leu Val Gly Ser Gly Ala Gly Leu Leu Val Phe Cys Lys Ser Pro
                265             270             275 ggc tac aaa ccc atc aag aag att cag tta caa ggc ggc atc act tct        919
Gly Tyr Lys Pro Ile Lys Lys Ile Gln Leu Gln Gly Gly Ile Thr Ser
280             285             290             295 atc aca ctt cga gga gaa gga cac cag ttt ctc gta gga aca gaa gaa        967
Ile Thr Leu Arg Gly Glu Gly His Gln Phe Leu Val Gly Thr Glu Glu
                300             305             310 tcg cac att tat cgt gtc agc ttc acg gat ttc aaa gag acg ctc ata       1015
Ser His Ile Tyr Arg Val Ser Phe Thr Asp Phe Lys Glu Thr Leu Ile
                315             320             325 gcg act tgt cac ttt gat gct gtc gag gat att gtc ttt cca ttt ggc       1063
Ala Thr Cys His Phe Asp Ala Val Glu Asp Ile Val Phe Pro Phe Gly
                330             335             340 act gct gag cta ttt gca acc tgt gcc aag aag gat atc agg gtg tgg       1111
Thr Ala Glu Leu Phe Ala Thr Cys Ala Lys Lys Asp Ile Arg Val Trp
                345             350             355 cac aca tca tcc aac agg gag ctg ctg cgg atc acc gtg ccc aac atg       1159
His Thr Ser Ser Asn Arg Glu Leu Leu Arg Ile Thr Val Pro Asn Met
360             365             370             375 acc tgc cac ggc atc gac ttc atg agg gac ggc aaa agc atc att tca       1207
Thr Cys His Gly Ile Asp Phe Met Arg Asp Gly Lys Ser Ile Ile Ser
                380             385             390 gca tgg aac gac ggt aaa atc cga gcc ttc gcc cca gag aca ggc cga       1255
Ala Trp Asn Asp Gly Lys Ile Arg Ala Phe Ala Pro Glu Thr Gly Arg
                395             400             405 ctg atg tat gtc att aac aat gct cac agg atc ggc gtc acc gcc atc       1303
Leu Met Tyr Val Ile Asn Asn Ala His Arg Ile Gly Val Thr Ala Ile
                410             415             420 gcc acc acc agt gac tgt aaa agg gtc atc agt ggc ggt ggg gaa ggg       1351
Ala Thr Thr Ser Asp Cys Lys Arg Val Ile Ser Gly Gly Gly Glu Gly
                425             430             435 gag gtg agg gta tgg cag ata ggc tgt cag acc cag aag ctg gag gag       1399
Glu Val Arg Val Trp Gln Ile Gly Cys Gln Thr Gln Lys Leu Glu Glu
```

```
                    440                 445                 450                 455
gcc ctg aag gaa cac aag tca tca gtg tcc tgc att agg gtg aag agg     1447
Ala Leu Lys Glu His Lys Ser Ser Val Ser Cys Ile Arg Val Lys Arg
                    460                 465                 470 aac aac gag gag tgt gtc acc gcc agc acc gat ggg act tgt atc att     1495
Asn Asn Glu Glu Cys Val Thr Ala Ser Thr Asp Gly Thr Cys Ile Ile
                475                 480                 485 tgg gac ctt gtg cgt ctc agg agg aat cag atg ata cta gcc aac acc     1543
Trp Asp Leu Val Arg Leu Arg Arg Asn Gln Met Ile Leu Ala Asn Thr
            490                 495                 500 tta ttc cag tgt gtg tgc tat cac cct gag gag ttc cag atc atc acc     1591
Leu Phe Gln Cys Val Cys Tyr His Pro Glu Glu Phe Gln Ile Ile Thr
        505                 510                 515 agc gga aca gac aga aag att gct tac tgg gaa gta ttt gat ggg aca     1639
Ser Gly Thr Asp Arg Lys Ile Ala Tyr Trp Glu Val Phe Asp Gly Thr
520                 525                 530                 535 gta atc aga gaa ttg gaa ggt tcc ctg tct ggg tcg ata aat ggc atg     1687
Val Ile Arg Glu Leu Glu Gly Ser Leu Ser Gly Ser Ile Asn Gly Met
                540                 545                 550 gat atc aca cag gaa ggg gtg cac ttt gtc aca ggt gga aat gac cat     1735
Asp Ile Thr Gln Glu Gly Val His Phe Val Thr Gly Gly Asn Asp His
                555                 560                 565 ctg gtc aaa gtt tgg gat tat aat gag ggt gaa gtg act cac gtt ggg     1783
Leu Val Lys Val Trp Asp Tyr Asn Glu Gly Glu Val Thr His Val Gly
            570                 575                 580 gtg gga cac agt ggc aac atc aca cgc atc cgc ata agt cca gga aat     1831
Val Gly His Ser Gly Asn Ile Thr Arg Ile Arg Ile Ser Pro Gly Asn
        585                 590                 595 caa tat att gtt agt gta agt gcc gat gga gcc att ttg cga tgg aag     1879
Gln Tyr Ile Val Ser Val Ser Ala Asp Gly Ala Ile Leu Arg Trp Lys
600                 605                 610                 615 tac cca tat acc tcc tga agctgatgag atgtctctga gccttggcgt            1927
Tyr Pro Tyr Thr Ser
            620 tgcacgcagt cctgttgaag actgagttta gataactcca acactagtct tcatttctca   1987 cagctctgtt tttgttcttg agtcaatttt tctctttttc tttatagaat gcattttata   2047 ttcttaaatt gcatattaaa attgaagtat gttcaagaat aatttgtgca gactctaatt   2107 agaacttta acattttgaa taaattctta gttgttggta aaaaa                    2152

<210> SEQ ID NO 2
<211> LENGTH: 620
<212> TYPE: PRT
<213> ORGANISM: Homo sapiens

<400> SEQUENCE: 2

Met Asp Asn Lys Ile Ser Pro Glu Ala Gln Val Ala Glu Leu Glu Leu
1               5                   10                  15

Asp Ala Val Ile Gly Phe Asn Gly His Val Pro Thr Gly Leu Lys Cys
                20                  25                  30

His Pro Asp Gln Glu His Met Ile Tyr Pro Leu Gly Cys Thr Val Leu
            35                  40                  45

Ile Gln Ala Ile Asn Thr Lys Glu Gln Asn Phe Leu Gln Gly His Gly
        50                  55                  60

Asn Asn Val Ser Cys Leu Ala Ile Ser Arg Ser Gly Glu Tyr Ile Ala
65                  70                  75                  80

Ser Gly Gln Val Thr Phe Met Gly Phe Lys Ala Asp Ile Ile Leu Trp
                85                  90                  95
```

-continued

```
Asp Tyr Lys Asn Arg Glu Leu Leu Ala Arg Leu Ser Leu His Lys Gly
            100                 105                 110
Lys Ile Glu Ala Leu Ala Phe Ser Pro Asn Asp Leu Tyr Leu Val Ser
        115                 120                 125
Leu Gly Gly Pro Asp Asp Gly Ser Val Val Trp Ser Ile Ala Lys
    130                 135                 140
Arg Asp Ala Ile Cys Gly Ser Pro Ala Gly Leu Asn Val Gly Asn
145                 150                 155                 160
Ala Thr Asn Val Ile Phe Ser Arg Cys Arg Asp Glu Met Phe Met Thr
                165                 170                 175
Ala Gly Asn Gly Thr Ile Arg Val Trp Glu Leu Asp Leu Pro Asn Arg
            180                 185                 190
Lys Ile Trp Pro Thr Glu Cys Gln Thr Gly Gln Leu Lys Arg Ile Val
        195                 200                 205
Met Ser Ile Gly Val Asp Asp Asp Ser Phe Phe Tyr Leu Gly Thr
    210                 215                 220
Thr Thr Gly Asp Ile Leu Lys Met Asn Pro Arg Thr Lys Leu Leu Thr
225                 230                 235                 240
Asp Val Gly Pro Ala Lys Asp Lys Phe Ser Leu Gly Val Ser Ala Ile
                245                 250                 255
Arg Cys Leu Lys Met Gly Gly Leu Leu Val Gly Ser Gly Ala Gly Leu
            260                 265                 270
Leu Val Phe Cys Lys Ser Pro Gly Tyr Lys Pro Ile Lys Lys Ile Gln
        275                 280                 285
Leu Gln Gly Gly Ile Thr Ser Ile Thr Leu Arg Gly Glu Gly His Gln
    290                 295                 300
Phe Leu Val Gly Thr Glu Glu Ser His Ile Tyr Arg Val Ser Phe Thr
305                 310                 315                 320
Asp Phe Lys Glu Thr Leu Ile Ala Thr Cys His Phe Asp Ala Val Glu
                325                 330                 335
Asp Ile Val Phe Pro Phe Gly Thr Ala Glu Leu Phe Ala Thr Cys Ala
            340                 345                 350
Lys Lys Asp Ile Arg Val Trp His Thr Ser Ser Asn Arg Glu Leu Leu
        355                 360                 365
Arg Ile Thr Val Pro Asn Met Thr Cys His Gly Ile Asp Phe Met Arg
    370                 375                 380
Asp Gly Lys Ser Ile Ile Ser Ala Trp Asn Asp Gly Lys Ile Arg Ala
385                 390                 395                 400
Phe Ala Pro Glu Thr Gly Arg Leu Met Tyr Val Ile Asn Asn Ala His
                405                 410                 415
Arg Ile Gly Val Thr Ala Ile Ala Thr Thr Ser Asp Cys Lys Arg Val
            420                 425                 430
Ile Ser Gly Gly Gly Glu Gly Glu Val Arg Val Trp Gln Ile Gly Cys
        435                 440                 445
Gln Thr Gln Lys Leu Glu Glu Ala Leu Lys Glu His Lys Ser Ser Val
    450                 455                 460
Ser Cys Ile Arg Val Lys Arg Asn Asn Glu Glu Cys Val Thr Ala Ser
465                 470                 475                 480
Thr Asp Gly Thr Cys Ile Ile Trp Asp Leu Val Arg Leu Arg Arg Asn
                485                 490                 495
Gln Met Ile Leu Ala Asn Thr Leu Phe Gln Cys Val Cys Tyr His Pro
            500                 505                 510
Glu Glu Phe Gln Ile Ile Thr Ser Gly Thr Asp Arg Lys Ile Ala Tyr
        515                 520                 525
```

```
Trp Glu Val Phe Asp Gly Thr Val Ile Arg Glu Leu Glu Gly Ser Leu
    530                 535                 540
Ser Gly Ser Ile Asn Gly Met Asp Ile Thr Gln Glu Gly Val His Phe
545                 550                 555                 560
Val Thr Gly Gly Asn Asp His Leu Val Lys Val Trp Asp Tyr Asn Glu
                565                 570                 575
Gly Glu Val Thr His Val Gly Val Gly His Ser Gly Asn Ile Thr Arg
            580                 585                 590
Ile Arg Ile Ser Pro Gly Asn Gln Tyr Ile Val Ser Val Ser Ala Asp
        595                 600                 605
Gly Ala Ile Leu Arg Trp Lys Tyr Pro Tyr Thr Ser
    610                 615                 620

<210> SEQ ID NO 3
<211> LENGTH: 2744
<212> TYPE: DNA
<213> ORGANISM: Homo sapiens
<220> FEATURE:
<221> NAME/KEY: CDS
<222> LOCATION: (343)..(1845)
<223> OTHER INFORMATION:

<400> SEQUENCE: 3
acacttgagg gcaaagaggt taggaagccg gcatggcgct ccggtcaata aaatcgatag      60
ctggaagctg cctgtgttcc aggcaaaggc ggtgcggtag cagcgccgcc atttccccg     120 aaggcatctt ccggtgcctt tcacccaagt tcgggcagga gtttcctgaa taacagcaaa    180
aggtttccgt tagccccgcg ggcgaccaat tccgattccc tccgggcctc cccggccacg    240
ctcagccctg gtccggcagg ggctcctcga tcccaggggc cgccagcgcc cgagggccga    300
ggcctggaca cggaaggccg tggcgccggc ttctcgggtc cc atg gcg cca cct      354
                                                 Met Ala Pro Pro
                                                  1 tcg gct ccg ctc cct gcg cag gga cca gga aag gcc aga ccc agt cgg    402
Ser Ala Pro Leu Pro Ala Gln Gly Pro Gly Lys Ala Arg Pro Ser Arg
 5              10                  15                  20 aaa agg ggc agg agg ccg agg gct ctg aag ttc gtg gac gtg gcc gtg    450
Lys Arg Gly Arg Arg Pro Arg Ala Leu Lys Phe Val Asp Val Ala Val
                25                  30                  35 tac ttc tcc ccg gag gag tgg ggc tgc ctg cgg ccc gcg cag agg gcc    498
Tyr Phe Ser Pro Glu Glu Trp Gly Cys Leu Arg Pro Ala Gln Arg Ala
            40                  45                  50 ctg tac cgg gac gtg atg cgg gag acc tac ggt cac ctg ggc gcg ctc    546
Leu Tyr Arg Asp Val Met Arg Glu Thr Tyr Gly His Leu Gly Ala Leu
        55                  60                  65 ggg tgc gca ggt ccc aaa cca gcc ctc atc tcc tgg ttg gaa cga aac    594
Gly Cys Ala Gly Pro Lys Pro Ala Leu Ile Ser Trp Leu Glu Arg Asn
    70                  75                  80 acc gat gac tgg gaa ccg gct gct cta gat ccg cag gag tac ccg aga    642
Thr Asp Asp Trp Glu Pro Ala Ala Leu Asp Pro Gln Glu Tyr Pro Arg
85                  90                  95                 100 ggg cta aca gtc cag aga aaa agc aga acc aga aag aag aat ggg gag    690
Gly Leu Thr Val Gln Arg Lys Ser Arg Thr Arg Lys Lys Asn Gly Glu
                105                 110                 115 aag gaa gta ttc ccg cct aag gag gca ccc cga aag ggg aag cga ggc    738
Lys Glu Val Phe Pro Pro Lys Glu Ala Pro Arg Lys Gly Lys Arg Gly
            120                 125                 130 cgg agg ccc agc aaa ccc cga ctg att cct agg cag acg tcc ggg ggc    786
Arg Arg Pro Ser Lys Pro Arg Leu Ile Pro Arg Gln Thr Ser Gly Gly
        135                 140                 145
```

```
ccc atc tgc cct gac tgc ggc tgt acc ttc cct gat cat cag gcc ctg      834
Pro Ile Cys Pro Asp Cys Gly Cys Thr Phe Pro Asp His Gln Ala Leu
    150                 155                 160 gag agc cac aag tgc gcc cag aat cta aaa aag cct tac cct tgc cca      882
Glu Ser His Lys Cys Ala Gln Asn Leu Lys Lys Pro Tyr Pro Cys Pro
165                 170                 175                 180 gac tgt ggg cgc cgc ttt tcc tat cca tcc ctg ctg gtc agt cac cgg      930
Asp Cys Gly Arg Arg Phe Ser Tyr Pro Ser Leu Leu Val Ser His Arg
                    185                 190                 195 cgg gca cac tcc ggc gag tgc ccc tat gtt tgt gac cag tgt ggc aaa      978
Arg Ala His Ser Gly Glu Cys Pro Tyr Val Cys Asp Gln Cys Gly Lys
                200                 205                 210 cgt ttc tcc cag cgc aag aac ctc tcc cag cac cag gtc atc cat aca     1026
Arg Phe Ser Gln Arg Lys Asn Leu Ser Gln His Gln Val Ile His Thr
            215                 220                 225 ggg gag aag ccc tat cac tgc cct gac tgt ggt cgc tgc ttc cgg agg     1074
Gly Glu Lys Pro Tyr His Cys Pro Asp Cys Gly Arg Cys Phe Arg Arg
        230                 235                 240 agc cgg tcc ttg gcc aat cac cgg acc aca cac aca ggt gaa aaa ccc     1122
Ser Arg Ser Leu Ala Asn His Arg Thr Thr His Thr Gly Glu Lys Pro
245                 250                 255                 260 cac cag tgc cct agc tgt gga cgt cgc ttc gcc tac ccc tcc ctg cta     1170
His Gln Cys Pro Ser Cys Gly Arg Arg Phe Ala Tyr Pro Ser Leu Leu
                    265                 270                 275 gcc atc cac cag cgt aca cac acg gga gag aag ccc tac act tgc ctc     1218
Ala Ile His Gln Arg Thr His Thr Gly Glu Lys Pro Tyr Thr Cys Leu
                280                 285                 290 gag tgc aac cgc cgc ttc cgc cag cgc acg gcc ctc gtc atc cac cag     1266
Glu Cys Asn Arg Arg Phe Arg Gln Arg Thr Ala Leu Val Ile His Gln
            295                 300                 305 cgc atc cac acg ggc gag aag ccc tac ccg tgc ccg gac tgc gag cgg     1314
Arg Ile His Thr Gly Glu Lys Pro Tyr Pro Cys Pro Asp Cys Glu Arg
        310                 315                 320 cgc ttc tcc tcc tcc tct cgc ctg gtc agt cac cgg gtg cac tct         1362
Arg Phe Ser Ser Ser Ser Arg Leu Val Ser His Arg Val His Ser
325                 330                 335                 340 ggg gag cgt ccc tat gcc tgc gag cac tgt gag gcc cgc ttc tcc cag     1410
Gly Glu Arg Pro Tyr Ala Cys Glu His Cys Glu Ala Arg Phe Ser Gln
                    345                 350                 355 cgc agc acg ctg ctc cag cac cag ctc ttg cac acc gga gag aag ccc     1458
Arg Ser Thr Leu Leu Gln His Gln Leu Leu His Thr Gly Glu Lys Pro
                360                 365                 370 tac ccc tgc cca gac tgt ggg cgt gcc ttc cgg cgg agc ggc tcc ctg     1506
Tyr Pro Cys Pro Asp Cys Gly Arg Ala Phe Arg Arg Ser Gly Ser Leu
        375                 380                 385 gcc atc cat cgc agc acg cac aca gag gag aag ctg cac gcc tgc gac     1554
Ala Ile His Arg Ser Thr His Thr Glu Glu Lys Leu His Ala Cys Asp
    390                 395                 400 gac tgt ggt cgc cgc ttt gcc tac ccc tca ctg ctg gcc agc cac cgg     1602
Asp Cys Gly Arg Arg Phe Ala Tyr Pro Ser Leu Leu Ala Ser His Arg
405                 410                 415                 420 cgc gtg cac tcg ggc gag cgg ccc tat gcc tgc gac ctt tgc tcc aag     1650
Arg Val His Ser Gly Glu Arg Pro Tyr Ala Cys Asp Leu Cys Ser Lys
                    425                 430                 435 cgt ttt gct cag tgg agc cac ctg gcc cag cac cag ctg ctg cac acg     1698
Arg Phe Ala Gln Trp Ser His Leu Ala Gln His Gln Leu Leu His Thr
                440                 445                 450 ggg gag aag cct ttc ccc tgc ctc gag tgt ggc cgg tgc ttc cgc cag     1746
Gly Glu Lys Pro Phe Pro Cys Leu Glu Cys Gly Arg Cys Phe Arg Gln
        455                 460                 465
```

-continued

```
agg tgg tct ctg gct gtc cac aag tgt agc ccc aag gcc cca aac tgt    1794
Arg Trp Ser Leu Ala Val His Lys Cys Ser Pro Lys Ala Pro Asn Cys
        470                 475                 480 agc cct aga tct gct atc ggg ggc tcc agt cag agg ggc aac gcc cat    1842
Ser Pro Arg Ser Ala Ile Gly Gly Ser Ser Gln Arg Gly Asn Ala His
    485                 490                 495             500 tag aaggggaagg actgcctacg ttcatttcat tttatggagg gtcccagaaa         1895
agggaaggag gagccccagg tcatacaggg cagagtcaga actaaacccg ggtctcctgc  1955
tgcacagagc tgaactttgt atcttgcaat gcgctggctg cctccctgtg cgtgtctgga  2015
acagtcccat taggagaggt gacgtcattt gcttaaagtt ttccaagcta ccctatccta  2075
aaatagtttg tgtggatatc agggctaaaa gttctcccca tctattttag gggctgtctg  2135
cttttctagt ctgtccacac aggattacc tgtcatcttg catgcaatca ggagaatctc   2195
ataggggcag gaccttcccc tactctgcct cttcctccat actaggttgg aaaaatctgg  2255
tttagcccac ttttgcaac actcctgcca agtggtcttc tacccattgc ttgaaaatct   2315
ctcttgacag ggagctcact acctcacaag gcaggtcatt tcattgtggg atctatagaa  2375
ggttaagtac cacattctcc tctaaacctt gcctacgaca tgtttaatac ttcatctaca  2435
tagcagccct tcagataatc acaaccactt tgcccccaag ttttcaggtt aagtagcatg  2495
aatttggtca ttccttaaag acagggtttc aatttccaca catgatctct gcaaacaggc  2555
actgggtttt cagtgtcctt tttgaagggt catataaaaa taaggtaaca ccacagtgcc  2615
actacacctt ctggggctgg acttgtttca gcagctttgg ttgcactgaa tttgggggag  2675
ctgcatggta ccagggggttt attgggttgc agatatataa atgccctaaa cttaaaaaaa  2735
aaaaaaaaa                                                          2744
```

<210> SEQ ID NO 4
<211> LENGTH: 500
<212> TYPE: PRT
<213> ORGANISM: Homo sapiens

<400> SEQUENCE: 4

```
Met Ala Pro Pro Ser Ala Pro Leu Pro Ala Gln Gly Pro Gly Lys Ala
1               5                   10                  15

Arg Pro Ser Arg Lys Arg Gly Arg Arg Pro Arg Ala Leu Lys Phe Val
            20                  25                  30

Asp Val Ala Val Tyr Phe Ser Pro Glu Glu Trp Gly Cys Leu Arg Pro
        35                  40                  45

Ala Gln Arg Ala Leu Tyr Arg Asp Val Met Arg Glu Thr Tyr Gly His
    50                  55                  60

Leu Gly Ala Leu Gly Cys Ala Gly Pro Lys Pro Ala Leu Ile Ser Trp
65                  70                  75                  80

Leu Glu Arg Asn Thr Asp Asp Trp Glu Pro Ala Ala Leu Asp Pro Gln
                85                  90                  95

Glu Tyr Pro Arg Gly Leu Thr Val Gln Arg Lys Ser Arg Thr Arg Lys
            100                 105                 110

Lys Asn Gly Glu Lys Glu Val Phe Pro Pro Lys Glu Ala Pro Arg Lys
        115                 120                 125

Gly Lys Arg Gly Arg Arg Pro Ser Lys Pro Arg Leu Ile Pro Arg Gln
    130                 135                 140

Thr Ser Gly Gly Pro Ile Cys Pro Asp Cys Gly Cys Thr Phe Pro Asp
145                 150                 155                 160

His Gln Ala Leu Glu Ser His Lys Cys Ala Gln Asn Leu Lys Lys Pro
```

```
                      165                 170                 175
Tyr Pro Cys Pro Asp Cys Gly Arg Arg Phe Ser Tyr Pro Ser Leu Leu
            180                 185                 190

Val Ser His Arg Arg Ala His Ser Gly Glu Cys Pro Tyr Val Cys Asp
            195                 200                 205

Gln Cys Gly Lys Arg Phe Ser Gln Arg Lys Asn Leu Ser Gln His Gln
            210                 215                 220

Val Ile His Thr Gly Glu Lys Pro Tyr His Cys Pro Asp Cys Gly Arg
225                 230                 235                 240

Cys Phe Arg Arg Ser Arg Ser Leu Ala Asn His Arg Thr His Thr
                245                 250                 255

Gly Glu Lys Pro His Gln Cys Pro Ser Cys Gly Arg Arg Phe Ala Tyr
            260                 265                 270

Pro Ser Leu Leu Ala Ile His Gln Arg Thr His Thr Gly Glu Lys Pro
            275                 280                 285

Tyr Thr Cys Leu Glu Cys Asn Arg Arg Phe Arg Gln Arg Thr Ala Leu
            290                 295                 300

Val Ile His Gln Arg Ile His Thr Gly Glu Lys Pro Tyr Pro Cys Pro
305                 310                 315                 320

Asp Cys Glu Arg Arg Phe Ser Ser Ser Arg Leu Val Ser His Arg
                325                 330                 335

Arg Val His Ser Gly Glu Arg Pro Tyr Ala Cys Glu His Cys Glu Ala
            340                 345                 350

Arg Phe Ser Gln Arg Ser Thr Leu Leu Gln His Gln Leu Leu His Thr
            355                 360                 365

Gly Glu Lys Pro Tyr Pro Cys Pro Asp Cys Gly Arg Ala Phe Arg Arg
            370                 375                 380

Ser Gly Ser Leu Ala Ile His Arg Ser Thr His Thr Glu Glu Lys Leu
385                 390                 395                 400

His Ala Cys Asp Asp Cys Gly Arg Arg Phe Ala Tyr Pro Ser Leu Leu
                405                 410                 415

Ala Ser His Arg Arg Val His Ser Gly Glu Arg Pro Tyr Ala Cys Asp
            420                 425                 430

Leu Cys Ser Lys Arg Phe Ala Gln Trp Ser His Leu Ala Gln His Gln
            435                 440                 445

Leu Leu His Thr Gly Glu Lys Pro Phe Pro Cys Leu Glu Cys Gly Arg
            450                 455                 460

Cys Phe Arg Gln Arg Trp Ser Leu Ala Val His Lys Cys Ser Pro Lys
465                 470                 475                 480

Ala Pro Asn Cys Ser Pro Arg Ser Ala Ile Gly Gly Ser Ser Gln Arg
                485                 490                 495

Gly Asn Ala His
            500

<210> SEQ ID NO 5
<211> LENGTH: 1706
<212> TYPE: DNA
<213> ORGANISM: Homo sapiens
<220> FEATURE:
<221> NAME/KEY: CDS
<222> LOCATION: (205)..(705)
<223> OTHER INFORMATION:

<400> SEQUENCE: 5
tgttcttgag cccagcttct tctcgtctcc caccccagct tcccggcatt ggaagaaggg      60
accgtcctct tccttgtctt ggccacccaa atcctggtat cgaaagggtt gaacggaccg     120
```

```
gaagtgtgca gcagcgacgg gtccccagct aatcgacgcc ggaagtagca attactagac      180
aagcattccg ccgccggctt cgct atg gcg gca att ccc cca gat tcc tgg         231
                           Met Ala Ala Ile Pro Pro Asp Ser Trp
                           1               5 cag cca ccc aac gtt tac ttg gag acc agc atg gga atc att gtg ctg        279
Gln Pro Pro Asn Val Tyr Leu Glu Thr Ser Met Gly Ile Ile Val Leu
10              15                  20                  25 gag ctg tac tgg aag cat gct cca aag acc tgt aag aac ttt gct gag        327
Glu Leu Tyr Trp Lys His Ala Pro Lys Thr Cys Lys Asn Phe Ala Glu
                30                  35                  40 ttg gct cgt cga ggt tac tac aat ggc aca aaa ttc cac aga att atc        375
Leu Ala Arg Arg Gly Tyr Tyr Asn Gly Thr Lys Phe His Arg Ile Ile
            45                  50                  55 aaa gac ttc atg atc caa gga ggt gac cca aca ggg aca ggt cga ggt        423
Lys Asp Phe Met Ile Gln Gly Gly Asp Pro Thr Gly Thr Gly Arg Gly
        60                  65                  70 ggt gca tct atc tat ggc aaa cag ttt gaa gat gaa ctt cat cca gac        471
Gly Ala Ser Ile Tyr Gly Lys Gln Phe Glu Asp Glu Leu His Pro Asp
    75                  80                  85 ttg aaa ttc acg ggg gct gga att ctc gca atg gcc aat gcg ggg cca        519
Leu Lys Phe Thr Gly Ala Gly Ile Leu Ala Met Ala Asn Ala Gly Pro
90                  95                  100                 105 gat acc aat ggc agc cag ttc ttt gtg acc ctc gcc ccc acc cag tgg        567
Asp Thr Asn Gly Ser Gln Phe Phe Val Thr Leu Ala Pro Thr Gln Trp
                110                 115                 120 ctt gac ggc aaa cac acc att ttt ggc cga gtg tgt cag ggc ata gga        615
Leu Asp Gly Lys His Thr Ile Phe Gly Arg Val Cys Gln Gly Ile Gly
            125                 130                 135 atg gtg aat cgc gtg gga atg gta gaa aca aac tcc cag gac cgc cct        663
Met Val Asn Arg Val Gly Met Val Glu Thr Asn Ser Gln Asp Arg Pro
        140                 145                 150 gtg gac gac gtg aag atc att aag gca tac cct tct ggg tag               705
Val Asp Asp Val Lys Ile Ile Lys Ala Tyr Pro Ser Gly
    155                 160                 165 acttgctacc ctcttgagca gctcttctga gatggcccca gtgaaccagc ttctagatga     765
catagaatga catgtaatgc taaatttcat tttggctttg caagtcatga agcttaggag     825
gcctggcatc ttgggtgagt tagagatgga agtacatttt aataggatgc ttcttttctc     885
ttcccccagt gcctaggttg ccagagcatt tgcacaaatg cccctgttta tcaataggtg     945
actacttact acacatgaac cataatgctg cttcttgtgc atgtctgctc tgatatacgt    1005
cgaacaatgt agcagccact gtcatttctc agtggttttg cctaaccaaa cttcttccta    1065
aggagattta tattctggcc tacacagcag tccttgatgg ctgacagcca cagaattcca    1125
aaccaagtag tgtctgtcag ccctcttaac tctgtgcacg ccctatttca gtcttttaca    1185
tttgttcttc tagggaatgt atgcatctct atatatattt tccctctcaa aaccagaaca    1245
tcaacagtgc tgtttctgac acttcagaca tcccacgcaa agccacattg aattttttgcc   1305 aaatgaaaaa cacatccaac aatcaagttt ctaagaaggt gtcaagtggg gaataataat    1365
aatgtataat aatcaagaaa ttagtttatt aaaaggaagc agaagcattg accatttttt    1425
cccagagaag aggagaaatc tgtagtgagc aaaggacaga ccatgaatcc tccttgagaa    1485
gtagtactct cagaaaggag aagcgccact caagttcttt taacccaaga ctttagaaaa    1545
attaggtcca agattttat atgttcagtt gtttatgtat aaaaataact ttctggattt     1605
tgtggggagc agcaggagag gaaggaagtt aatacctatg taatacatag aaacttccac    1665
aataaaatgc cattgatggt tgaaaaaaaa aaaaaaaaaa a                         1706
```

<210> SEQ ID NO 6
<211> LENGTH: 166
<212> TYPE: PRT
<213> ORGANISM: Homo sapiens

<400> SEQUENCE: 6

```
Met Ala Ala Ile Pro Pro Asp Ser Trp Gln Pro Pro Asn Val Tyr Leu
1               5                   10                  15

Glu Thr Ser Met Gly Ile Ile Val Leu Glu Leu Tyr Trp Lys His Ala
            20                  25                  30

Pro Lys Thr Cys Lys Asn Phe Ala Glu Leu Ala Arg Arg Gly Tyr Tyr
        35                  40                  45

Asn Gly Thr Lys Phe His Arg Ile Ile Lys Asp Phe Met Ile Gln Gly
    50                  55                  60

Gly Asp Pro Thr Gly Thr Gly Arg Gly Gly Ala Ser Ile Tyr Gly Lys
65                  70                  75                  80

Gln Phe Glu Asp Glu Leu His Pro Asp Leu Lys Phe Thr Gly Ala Gly
                85                  90                  95

Ile Leu Ala Met Ala Asn Ala Gly Pro Asp Thr Asn Gly Ser Gln Phe
            100                 105                 110

Phe Val Thr Leu Ala Pro Thr Gln Trp Leu Asp Gly Lys His Thr Ile
        115                 120                 125

Phe Gly Arg Val Cys Gln Gly Ile Gly Met Val Asn Arg Val Gly Met
    130                 135                 140

Val Glu Thr Asn Ser Gln Asp Arg Pro Val Asp Val Lys Ile Ile
145                 150                 155                 160

Lys Ala Tyr Pro Ser Gly
                165
```

<210> SEQ ID NO 7
<211> LENGTH: 2607
<212> TYPE: DNA
<213> ORGANISM: Homo sapiens
<220> FEATURE:
<221> NAME/KEY: CDS
<222> LOCATION: (354)..(1898)
<223> OTHER INFORMATION:

<400> SEQUENCE: 7

```
gaaatatgaa gagacgctgc agctgcggtg gcggtggcgg ccactgcagc tcagagcggc    60
gcacgcggcg gccggggcgg gacgcggggc cgggcgcgga gaagtcgggg cgggcggcag   120
agaggccggg acgcggaccg ggccggggcg cccacagccg cccgacggcg cccagagagc   180
gcgcgccccg cagccccgcg cctagcccgc cgggcatggg gcgcgcggca gccgcctgaa   240
gccccggcct ggcccggccg cacccggccg gaggggaggg cagagcgcgc gcccagttgc   300
ccgggcacca aatcggagcg cggcgtgcgg gagggcccag agcaggactg gaa atg      356
                                                        Met
                                                        1 tcc tgg ccg cgc cgc ctc ctg ctc aga tac ctg ttc ccg gcc ctc ctg    404
Ser Trp Pro Arg Arg Leu Leu Leu Arg Tyr Leu Phe Pro Ala Leu Leu
        5                   10                  15 ctt cac ggg ctg gga gag ggt tct gcc ctc ctt cat cca gac agc agg    452
Leu His Gly Leu Gly Glu Gly Ser Ala Leu Leu His Pro Asp Ser Arg
        20                  25                  30 tct cat cct agg tcc tta gag aaa agt gcc tgg agg gct ttt aag gag    500
Ser His Pro Arg Ser Leu Glu Lys Ser Ala Trp Arg Ala Phe Lys Glu
 35                  40                  45
```

| | | |
|---|---|---|
| tca cag tgc cat cac atg ctc aaa cat ctc cac aat ggt gca agg atc<br>Ser Gln Cys His His Met Leu Lys His Leu His Asn Gly Ala Arg Ile<br>50                          55                   60                   65 | | 548 |
| aca gtg cag atg cca cct aca atc gag ggc cac tgg gtc tcc aca ggc<br>Thr Val Gln Met Pro Pro Thr Ile Glu Gly His Trp Val Ser Thr Gly<br>                  70                   75                   80 | | 596 |
| tgt gaa gta agg tca ggc cca gag ttc atc aca agg tcc tac aga ttc<br>Cys Glu Val Arg Ser Gly Pro Glu Phe Ile Thr Arg Ser Tyr Arg Phe<br>            85                   90                   95 | | 644 |
| tac cac aat aac acc ttc aag gcc tac caa ttt tat tat ggc agc aac<br>Tyr His Asn Asn Thr Phe Lys Ala Tyr Gln Phe Tyr Tyr Gly Ser Asn<br>          100                   105                110 | | 692 |
| cgg tgc aca aat ccc act tat act ctc atc atc cgg ggc aag atc cgc<br>Arg Cys Thr Asn Pro Thr Tyr Thr Leu Ile Ile Arg Gly Lys Ile Arg<br>115                       120                125 | | 740 |
| ctc cgc cag gcc tcc tgg atc atc cga ggg ggc acg gaa gcc gac tac<br>Leu Arg Gln Ala Ser Trp Ile Ile Arg Gly Gly Thr Glu Ala Asp Tyr<br>130                       135                140                145 | | 788 |
| cag ctg cac aac gtc cag gtg atc tgc cac aca gag gcg gtg gcc gag<br>Gln Leu His Asn Val Gln Val Ile Cys His Thr Glu Ala Val Ala Glu<br>                  150                155                160 | | 836 |
| aag ctc ggc cag cag gtg aac cgc aca tgc ccg ggc ttc ctc gca gac<br>Lys Leu Gly Gln Gln Val Asn Arg Thr Cys Pro Gly Phe Leu Ala Asp<br>                165                170                175 | | 884 |
| ggg ggt ccc tgg gtg cag gac gtg gcc tat gac ctc tgg cga gag gag<br>Gly Gly Pro Trp Val Gln Asp Val Ala Tyr Asp Leu Trp Arg Glu Glu<br>180                       185                190 | | 932 |
| aac ggc tgt gag tgc acc aag gcc gtg aac ttt gcc atg cat gaa ctt<br>Asn Gly Cys Glu Cys Thr Lys Ala Val Asn Phe Ala Met His Glu Leu<br>          195                   200                205 | | 980 |
| cag ctc atc cgg gtg gag aag cag tac ctt cac cac aac ctc gac cac<br>Gln Leu Ile Arg Val Glu Lys Gln Tyr Leu His His Asn Leu Asp His<br>210                       215                220                225 | | 1028 |
| ctg gtc gag gag ctc ttc ctt ggt gac att cac act gat gcc acc cag<br>Leu Val Glu Glu Leu Phe Leu Gly Asp Ile His Thr Asp Ala Thr Gln<br>                230                235                240 | | 1076 |
| agg atg ttc tac cgg ccc tcc agt tac cag ccc cct ctg cag aat gcc<br>Arg Met Phe Tyr Arg Pro Ser Ser Tyr Gln Pro Pro Leu Gln Asn Ala<br>            245                   250                255 | | 1124 |
| aag aac cac gac cat gcc tgc atc gcc tgt cgg atc atc tat cgg tca<br>Lys Asn His Asp His Ala Cys Ile Ala Cys Arg Ile Ile Tyr Arg Ser<br>          260                   265                270 | | 1172 |
| gac gag cac cac cct ccc atc ctg ccc cca aag gca gac ctg acc atc<br>Asp Glu His His Pro Pro Ile Leu Pro Pro Lys Ala Asp Leu Thr Ile<br>275                       280                285 | | 1220 |
| ggc ctg cac ggg gag tgg gtg agc cag cgc tgt gag gtg cgc ccc gaa<br>Gly Leu His Gly Glu Trp Val Ser Gln Arg Cys Glu Val Arg Pro Glu<br>290                       295                300                305 | | 1268 |
| gtc ctc ttc ctc acc cgc cac ttc atc ttc cat gac aac aac aac acc<br>Val Leu Phe Leu Thr Arg His Phe Ile Phe His Asp Asn Asn Asn Thr<br>                310                315                320 | | 1316 |
| tgg gag ggc cac tac tac cac tac tca gac ccg gtg tgc aag cac ccc<br>Trp Glu Gly His Tyr Tyr His Tyr Ser Asp Pro Val Cys Lys His Pro<br>          325                   330                335 | | 1364 |
| acc ttc tcc atc tac gcc cgg ggc cgc tac agc cgc ggc gtc ctc tcg<br>Thr Phe Ser Ile Tyr Ala Arg Gly Arg Tyr Ser Arg Gly Val Leu Ser<br>340                       345                350 | | 1412 |
| tcc agg gtc atg gga ggc acc gag ttc gtg ttc aaa gtg aat cac atg<br>Ser Arg Val Met Gly Gly Thr Glu Phe Val Phe Lys Val Asn His Met<br>355                       360                365 | | 1460 |

```
aag gtc acc ccc atg gat gcg gcc aca gcc tca ctg ctc aac gtc ttc    1508
Lys Val Thr Pro Met Asp Ala Ala Thr Ala Ser Leu Leu Asn Val Phe
370                 375                 380                 385 aac ggg aat gag tgc ggg gcc gag ggc tcc tgg cag gtg ggc atc cag    1556
Asn Gly Asn Glu Cys Gly Ala Glu Gly Ser Trp Gln Val Gly Ile Gln
                390                 395                 400 cag gat gtg acc cac acc aat ggc tgc gtg gcc ctg ggc atc aaa cta    1604
Gln Asp Val Thr His Thr Asn Gly Cys Val Ala Leu Gly Ile Lys Leu
            405                 410                 415 cct cac acg gag tac gag atc ttc aaa atg gaa cag gat gcc cgg ggg    1652
Pro His Thr Glu Tyr Glu Ile Phe Lys Met Glu Gln Asp Ala Arg Gly
        420                 425                 430 cgc tat ctg ctg ttc aac ggt cag agg ccc agc gac ggg tcc agc cca    1700
Arg Tyr Leu Leu Phe Asn Gly Gln Arg Pro Ser Asp Gly Ser Ser Pro
    435                 440                 445 gac agg cca gag aag aga gcc acg tcc tac cag atg ccc ttg gtc cag    1748
Asp Arg Pro Glu Lys Arg Ala Thr Ser Tyr Gln Met Pro Leu Val Gln
450                 455                 460                 465 tgt gcc tcc tct tcg ccg agg gca gag gac ctc gca gaa gac agt gga    1796
Cys Ala Ser Ser Ser Pro Arg Ala Glu Asp Leu Ala Glu Asp Ser Gly
                470                 475                 480 agc agc ctg tat ggc cgg gcc cct ggg agg cac acc tgg tcc ctg ctg    1844
Ser Ser Leu Tyr Gly Arg Ala Pro Gly Arg His Thr Trp Ser Leu Leu
            485                 490                 495 ctg gct gca ctt gcc tgc ctt gtc cct ctg cat tgg aac atc cgc        1892
Leu Ala Ala Leu Ala Cys Leu Val Pro Leu Leu His Trp Asn Ile Arg
        500                 505                 510 aga tag aagttttaga aagttctatt ttttccaaac caggattcct tactattgac    1948
Arg agatttgctt taccaaaaga aaagacattt attcttttga tgcacttgaa tgccagagaa    2008
ctgtccttct ttttctcctc tccctccctc ccagccctg agtcatgaac agcaaggagt    2068
gtttgaagtt tctgctttga actccgtcca gcctgatccc tggcctgagc aacttcacaa    2128
cagtaattgc actttaagac agcctagagt tctggacgag cgtgtttggt agcagggatg    2188
aaagctaggg cctcttattt ttttctctta attattatta tatttctgag ttaaacttag    2248
aagaaacaac tatcaagcta caacttttcc tgccattttc ctgtggttgc agcctgtctt    2308
cctttgaaat tgttttactc tctgagtttt atatgctgga atccaatgca gagttggttt    2368
gggactgtga tcaagacacc ttttattaat aaagaagaga cacaggtgta gatatgtata    2428
tacaaaaaga tgtacggtct ggccaaacca ccttcccagc ctttatgcaa aaaaagggga    2488
gaatcaaagc tttcatttca gaaatgttgc gtggaaaagt atctgtaatt aaagtttcga    2548
agtaatttaa aaaaaaaaaa aaaaaaaaa aaaaaaaaaa agaaaaaaaa aaaaaaaa    2607
```

<210> SEQ ID NO 8
<211> LENGTH: 514
<212> TYPE: PRT
<213> ORGANISM: Homo sapiens

<400> SEQUENCE: 8

Met Ser Trp Pro Arg Arg Leu Leu Leu Arg Tyr Leu Phe Pro Ala Leu
1               5                   10                  15

Leu Leu His Gly Leu Gly Glu Gly Ser Ala Leu Leu His Pro Asp Ser
            20                  25                  30

Arg Ser His Pro Arg Ser Leu Glu Lys Ser Ala Trp Arg Ala Phe Lys
        35                  40                  45

Glu Ser Gln Cys His His Met Leu Lys His Leu His Asn Gly Ala Arg
    50                  55                  60

```
Ile Thr Val Gln Met Pro Pro Thr Ile Glu Gly His Trp Val Ser Thr
 65                  70                  75                  80

Gly Cys Glu Val Arg Ser Gly Pro Glu Phe Ile Thr Arg Ser Tyr Arg
             85                  90                  95

Phe Tyr His Asn Asn Thr Phe Lys Ala Tyr Gln Phe Tyr Gly Ser
            100                 105                 110

Asn Arg Cys Thr Asn Pro Thr Tyr Thr Leu Ile Ile Arg Gly Lys Ile
            115                 120                 125

Arg Leu Arg Gln Ala Ser Trp Ile Ile Arg Gly Thr Glu Ala Asp
        130                 135                 140

Tyr Gln Leu His Asn Val Gln Val Ile Cys His Thr Glu Ala Val Ala
145                 150                 155                 160

Glu Lys Leu Gly Gln Gln Val Asn Arg Thr Cys Pro Gly Phe Leu Ala
                165                 170                 175

Asp Gly Gly Pro Trp Val Gln Asp Val Ala Tyr Asp Leu Trp Arg Glu
            180                 185                 190

Glu Asn Gly Cys Glu Cys Thr Lys Ala Val Asn Phe Ala Met His Glu
            195                 200                 205

Leu Gln Leu Ile Arg Val Glu Lys Gln Tyr Leu His His Asn Leu Asp
210                 215                 220

His Leu Val Glu Glu Leu Phe Leu Gly Asp Ile His Thr Asp Ala Thr
225                 230                 235                 240

Gln Arg Met Phe Tyr Arg Pro Ser Ser Tyr Gln Pro Pro Leu Gln Asn
                245                 250                 255

Ala Lys Asn His Asp His Ala Cys Ile Ala Cys Arg Ile Ile Tyr Arg
                260                 265                 270

Ser Asp Glu His His Pro Pro Ile Leu Pro Pro Lys Ala Asp Leu Thr
            275                 280                 285

Ile Gly Leu His Gly Glu Trp Val Ser Gln Arg Cys Glu Val Arg Pro
290                 295                 300

Glu Val Leu Phe Leu Thr Arg His Phe Ile Phe His Asp Asn Asn Asn
305                 310                 315                 320

Thr Trp Glu Gly His Tyr Tyr His Tyr Ser Asp Pro Val Cys Lys His
                325                 330                 335

Pro Thr Phe Ser Ile Tyr Ala Arg Gly Arg Tyr Ser Arg Gly Val Leu
            340                 345                 350

Ser Ser Arg Val Met Gly Gly Thr Glu Phe Val Phe Lys Val Asn His
        355                 360                 365

Met Lys Val Thr Pro Met Asp Ala Ala Thr Ala Ser Leu Leu Asn Val
    370                 375                 380

Phe Asn Gly Asn Glu Cys Gly Ala Glu Gly Ser Trp Gln Val Gly Ile
385                 390                 395                 400

Gln Gln Asp Val Thr His Thr Asn Gly Cys Val Ala Leu Gly Ile Lys
                405                 410                 415

Leu Pro His Thr Glu Tyr Glu Ile Phe Lys Met Glu Gln Asp Ala Arg
            420                 425                 430

Gly Arg Tyr Leu Leu Phe Asn Gly Gln Arg Pro Ser Asp Gly Ser Ser
        435                 440                 445

Pro Asp Arg Pro Glu Lys Arg Ala Thr Ser Tyr Gln Met Pro Leu Val
    450                 455                 460

Gln Cys Ala Ser Ser Pro Arg Ala Glu Asp Leu Ala Glu Asp Ser
465                 470                 475                 480

Gly Ser Ser Leu Tyr Gly Arg Ala Pro Gly Arg His Thr Trp Ser Leu
```

```
                485                 490                 495
Leu Leu Ala Ala Leu Ala Cys Leu Val Pro Leu Leu His Trp Asn Ile
            500                 505                 510
Arg Arg

<210> SEQ ID NO 9
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 9
caggtggaaa tgaccatctg gtcaaag                                          27

<210> SEQ ID NO 10
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 10
catcagcttc aggaggtata tggtac                                           26

<210> SEQ ID NO 11
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 11
gtggcactgt ggtgttacct tat                                              23

<210> SEQ ID NO 12
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 12
cctctaaacc tttgcctacg act                                              23

<210> SEQ ID NO 13
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 13
ttaccgtcgt tccatgctga aatgatgc                                         28

<210> SEQ ID NO 14
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 14
ggggtaccac catggataac aaaatttcgc cggag                                 35
```

```
<210> SEQ ID NO 15
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 15
cggaattctc aggaggtata tgggtacttc catgc                              35

<210> SEQ ID NO 16
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 16
ggcctcacca ttgaag                                                  16

<210> SEQ ID NO 17
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 17
cttcaatggt gaggcc                                                  16

<210> SEQ ID NO 18
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 18
tggtagccaa gtgcaggtta ta                                           22

<210> SEQ ID NO 19
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 19
ccaaagggtt tctgcagttt ca                                           22

<210> SEQ ID NO 20
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 20
tgcggatcca gagcagattg tactgagagt                                   30

<210> SEQ ID NO 21
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 21
```
ctctatctcg agtgaggcgg aaagaacca                                    29

<210> SEQ ID NO 22
<211> LENGTH: 47
<212> TYPE: DNA
<213> ORGANISM: Artificial
<220> FEATURE:
<223> OTHER INFORMATION: an artificially synthesized primer sequence

<400> SEQUENCE: 22
tttaagcttg aagaccattt ttggaaaaaa aaaaaaaaa aaaaaac                 47

<210> SEQ ID NO 23
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 23
tttaagcttg aagacatggg aaagagtggt ctca                              34

<210> SEQ ID NO 24
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 24
caccaatgtg atcttctcca ggtgcttcaa gagagcacct ggagaagatc acatt       55

<210> SEQ ID NO 25
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 25
aaaaaatgtg atcttctcca ggtgctctct tgaagcacct ggagaagatc acatt       55

<210> SEQ ID NO 26
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 26
caccaaggac accagtttct cgtagttcaa gagactacga gaaactggtg tcctt       55

<210> SEQ ID NO 27
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 27
aaaaaaggac accagtttct cgtagtctct tgaactacga gaaactggtg tcctt       55

```
<210> SEQ ID NO 28
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 28
caccaaagag acgctcatag cgactttcaa gagaagtcgc tatgagcgtc tcttt            55

<210> SEQ ID NO 29
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 29
aaaaaaagag acgctcatag cgacttctct tgaaagtcgc tatgagcgtc tcttt            55

<210> SEQ ID NO 30
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 30
caccaacgac ggtaaaatcc gagccttcaa gagaggctcg gattttaccg tcgtt            55

<210> SEQ ID NO 31
<211> LENGTH: 55
<212> TYPE: DNA
<213> ORGANISM: Artificial
<220> FEATURE:
<223> OTHER INFORMATION: an artificially synthesized oligonucleotide for
      siRNA

<400> SEQUENCE: 31
aaaaaacgac ggtaaaatcc gagcctctct tgaaggctcg gattttaccg tcgtt            55

<210> SEQ ID NO 32
<211> LENGTH: 51
<212> TYPE: DNA
<213> ORGANISM: Artificial
<220> FEATURE:
<223> OTHER INFORMATION: an artificially synthesized oligonucleotide

<400> SEQUENCE: 32
caccgaagca gcacgacttc ttcttcaaga gagaagaagt cgtgctgctt c                51

<210> SEQ ID NO 33
<211> LENGTH: 51
<212> TYPE: DNA
<213> ORGANISM: Artificial
<220> FEATURE:
<223> OTHER INFORMATION: an artificially synthesized oligonucleotide

<400> SEQUENCE: 33
aaaagaagca gcacgacttc ttctctcttg aagaagaagt cgtgctgctt c                51

<210> SEQ ID NO 34
<211> LENGTH: 28
<212> TYPE: DNA
<213> ORGANISM: Artificial
```

```
<220> FEATURE:
<223> OTHER INFORMATION: an artificially synthesized primer sequence

<400> SEQUENCE: 34
tagattctgg gcgcacttgt ggctctcc                                        28

<210> SEQ ID NO 35
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 35
ggggtaccac catggcgcca ccttcg                                          26

<210> SEQ ID NO 36
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 36
cggaattcat gggcgttgcc cctctgactg g                                    31

<210> SEQ ID NO 37
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 37
ggcctcaccg agcgcg                                                     16

<210> SEQ ID NO 38
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 38
cgcgctcggt gaggcc                                                     16

<210> SEQ ID NO 39
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 39
ggacaggtcg aggtggtgc                                                  19

<210> SEQ ID NO 40
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 40
ctcgacgagt tctcccatcg                                                 20
```

```
<210> SEQ ID NO 41
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 41
agacaagctt ccgccgccg gc                                              22

<210> SEQ ID NO 42
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 42
gtctctcgag aagggtatgc cttaatgatc ttc                                 33

<210> SEQ ID NO 43
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 43
cttcgctatg gcggca                                                    16

<210> SEQ ID NO 44
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 44
tgccgccata gcgaag                                                    16

<210> SEQ ID NO 45
<211> LENGTH: 34
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (7)..(7)
<223> OTHER INFORMATION: q

<400> SEQUENCE: 45
tgggaanttc cggaagaaga tggcgctcac cagc                                34

<210> SEQ ID NO 46
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 46
gtgcctcgag cttcctcctc ttcttgcctt catgc                               35

<210> SEQ ID NO 47
<211> LENGTH: 51
<212> TYPE: DNA
<213> ORGANISM: Artificial
```

```
<220> FEATURE:
<223> OTHER INFORMATION: an artificially synthesized oligonucleotide for
      siRNA

<400> SEQUENCE: 47
tcccgcatgc tccaaagacc tgtttcaaga gaacaggtct ttggagcatg c         51

<210> SEQ ID NO 48
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 48
aaaagcatgc tccaaagacc tgttctcttg aaacaggtct ttggagcatg c         51

<210> SEQ ID NO 49
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 49
tcccagactt catgatccaa ggattcaaga gatccttgga tcatgaagtc t         51

<210> SEQ ID NO 50
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 50
aaaaagactt catgatccaa ggatctcttg aatccttgga tcatgaagtc t         51

<210> SEQ ID NO 51
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 51
tccctggcag ccagttcttt gtgttcaaga gacacaaaga actggctgcc a         51

<210> SEQ ID NO 52
<211> LENGTH: 51
<212> TYPE: DNA
<213> ORGANISM: Artificial
<220> FEATURE:
<223> OTHER INFORMATION: an artificially synthesized oligonucleotide for
      siRNA

<400> SEQUENCE: 52
aaaatggcag ccagttcttt gtgtctcttg aacacaaaga actggctgcc a         51

<210> SEQ ID NO 53
<211> LENGTH: 32
<212> TYPE: DNA
<213> ORGANISM: Artificial
<220> FEATURE:
<223> OTHER INFORMATION: an artificially synthesized primer sequence
```

```
<400> SEQUENCE: 53
cgccggatcc gctatggcgg caattccccc ag                                32

<210> SEQ ID NO 54
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 54
agcactcgag cccagaaggg tatgccttaa tgatc                             35

<210> SEQ ID NO 55
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 55
attggtacca tggagctgat tctcagccct cggtc                             35

<210> SEQ ID NO 56
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 56
aatctcgagg tcagcttcag tctcgtcagc ag                                32

<210> SEQ ID NO 57
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 57
attggtacca tggttccaga attccccctt tcccct                            36

<210> SEQ ID NO 58
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 58
aatctcgagg tcagcttcag tctcgtcagc ag                                32

<210> SEQ ID NO 59
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 59
attggtacca tggatctttc cctggaggaa attcag                            36

<210> SEQ ID NO 60
<211> LENGTH: 32
```

```
<212> TYPE: DNA
<213> ORGANISM: Artificial
<220> FEATURE:
<223> OTHER INFORMATION: an artificially synthesized primer sequence

<400> SEQUENCE: 60
aatctcgagg tcagcttcag tctcgtcagc ag                                32

<210> SEQ ID NO 61
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 61
attggtacca tggctgaggt cttgaagcag ctggc                             35

<210> SEQ ID NO 62
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 62
aatctcgagg tcagcttcag tctcgtcagc ag                                32

<210> SEQ ID NO 63
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 63
attggtacct tcaccatggc ttcttctgat atcc                              34

<210> SEQ ID NO 64
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 64
aatctcgagg cgtctttctt ctgcagcttc                                   30

<210> SEQ ID NO 65
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 65
ctggagaagc gtgccgcagg ccaggctttt g                                 31

<210> SEQ ID NO 66
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 66
caaaagcctg gcctgcggca cgcttctcca g                                 31
```

<210> SEQ ID NO 67
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 67
gcttttgagc tgattctcgc ccctcggtca aaagaatctg                             40

<210> SEQ ID NO 68
<211> LENGTH: 40
<212> TYPE: DNA
<213> ORGANISM: Artificial
<220> FEATURE:
<223> OTHER INFORMATION: an artificially synthesized primer sequence

<400> SEQUENCE: 68
cagattcttt tgaccgaggg gcgagaatca gctcaaaagc                             40

<210> SEQ ID NO 69
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 69
ccagaattcc cccttgcccc tccaaagaag aag                                    33

<210> SEQ ID NO 70
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 70
cttcttcttt ggaggggcaa gggggaattc tgg                                    33

<210> SEQ ID NO 71
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 71
cagaagaaag acgcaaggcc catgaagctg agg                                    33

<210> SEQ ID NO 72
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 72
cctcagcttc atgggccttg cgtctttctt ctg                                    33

<210> SEQ ID NO 73
<211> LENGTH: 21
<212> TYPE: DNA
<213> ORGANISM: Artificial
<220> FEATURE:
<223> OTHER INFORMATION: an artificially synthesized primer sequence

```
<400> SEQUENCE: 73
ggatcatcta tcggtcagac g                                            21

<210> SEQ ID NO 74
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 74
tgggtcacat cctgctggat g                                            21

<210> SEQ ID NO 75
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 75
gctcgtctga ccgatagatg atcc                                         24

<210> SEQ ID NO 76
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 76
aaggatccgc gtggacaatg gctactcaag                                   30

<210> SEQ ID NO 77
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 77
ggactcgaga caggtcagta tcaaaccagg ccag                              34

<210> SEQ ID NO 78
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 78
aagaattctg ctggtgggtg aaaaaaaaat gc                                32

<210> SEQ ID NO 79
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 79
ctactcgagt tctaaagact tggtgacgag cgac                              34

<210> SEQ ID NO 80
<211> LENGTH: 35
```

```
<212> TYPE: DNA
<213> ORGANISM: Artificial
<220> FEATURE:
<223> OTHER INFORMATION: an artificially synthesized primer sequence

<400> SEQUENCE: 80
aggaattcgt gcatcatggt cccaccacat catac                              35

<210> SEQ ID NO 81
<211> LENGTH: 7
<212> TYPE: DNA
<213> ORGANISM: Artificial
<220> FEATURE:
<223> OTHER INFORMATION: an artificially synthesized sequence

<400> SEQUENCE: 81 ctttggc                                                              7

<210> SEQ ID NO 82
<211> LENGTH: 16
<212> TYPE: DNA
<213> ORGANISM: Artificial
<220> FEATURE:
<223> OTHER INFORMATION: an artificially synthesized probe sequence

<400> SEQUENCE: 82
gctttgattg tggtga                                                   16

<210> SEQ ID NO 83
<211> LENGTH: 16
<212> TYPE: DNA
<213> ORGANISM: Artificial
<220> FEATURE:
<223> OTHER INFORMATION: an artificially synthesized probe sequence

<400> SEQUENCE: 83
tcaccacaat caaagc                                                   16

<210> SEQ ID NO 84
<211> LENGTH: 16
<212> TYPE: DNA
<213> ORGANISM: Artificial
<220> FEATURE:
<223> OTHER INFORMATION: an artificially synthesized probe sequence

<400> SEQUENCE: 84
cccctttgaa cacctt                                                   16

<210> SEQ ID NO 85
<211> LENGTH: 16
<212> TYPE: DNA
<213> ORGANISM: Artificial
<220> FEATURE:
<223> OTHER INFORMATION: an artificially synthesized probe sequence

<400> SEQUENCE: 85
aaggtgttca aagggg                                                   16

<210> SEQ ID NO 86
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 86
gcggaattca gggcccagag caggactg                                      28
```

<210> SEQ ID NO 87
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 87
tagctcgagc taaaacttct atctgcggat gt                                    32

<210> SEQ ID NO 88
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 88
atgtcctggc cgcgcc                                                      16

<210> SEQ ID NO 89
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 89
ggcgcggcca ggacat                                                      16

<210> SEQ ID NO 90
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 90
tacaggaccg gcgcgg                                                      16

<210> SEQ ID NO 91
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 91
atctggtccg gcgcgg                                                      16

<210> SEQ ID NO 92
<211> LENGTH: 16
<212> TYPE: DNA
<213> ORGANISM: Artificial
<220> FEATURE:
<223> OTHER INFORMATION: an artificially synthesized S-oligonucleotide

<400> SEQUENCE: 92
gttgcacagc gacgca                                                      16

<210> SEQ ID NO 93
<211> LENGTH: 21
<212> TYPE: DNA
<213> ORGANISM: Homo sapiens

<400> SEQUENCE: 93
aatgtgatct tctccaggtg c          21

<210> SEQ ID NO 94
<211> LENGTH: 21
<212> TYPE: DNA
<213> ORGANISM: Homo sapiens

<400> SEQUENCE: 94
aaggacacca gtttctcgta g          21

<210> SEQ ID NO 95
<211> LENGTH: 21
<212> TYPE: DNA
<213> ORGANISM: Homo sapiens

<400> SEQUENCE: 95
aaagagacgc tcatagcgac t          21

<210> SEQ ID NO 96
<211> LENGTH: 21
<212> TYPE: DNA
<213> ORGANISM: Homo sapiens

<400> SEQUENCE: 96
aacgacggta aaatccgagc c          21

<210> SEQ ID NO 97
<211> LENGTH: 21
<212> TYPE: DNA
<213> ORGANISM: Homo sapiens

<400> SEQUENCE: 97
aacgaaacac cgatgactgg g          21

<210> SEQ ID NO 98
<211> LENGTH: 21
<212> TYPE: DNA
<213> ORGANISM: Homo sapiens

<400> SEQUENCE: 98
aatcaccgga ccacacacac a          21

<210> SEQ ID NO 99
<211> LENGTH: 22
<212> TYPE: DNA
<213> ORGANISM: Homo sapiens

<400> SEQUENCE: 99
aaaccttgcc tacgacatgt tt         22

<210> SEQ ID NO 100
<211> LENGTH: 21
<212> TYPE: DNA
<213> ORGANISM: Homo sapiens

<400> SEQUENCE: 100
aaaaggtttc cgttagcccc g          21

<210> SEQ ID NO 101
<211> LENGTH: 20
<212> TYPE: DNA
<213> ORGANISM: Homo sapiens

<400> SEQUENCE: 101

```
gcatgctcca aagacctgtt                                                20

<210> SEQ ID NO 102
<211> LENGTH: 20
<212> TYPE: DNA
<213> ORGANISM: Homo sapiens

<400> SEQUENCE: 102
agacttcatg atccaaggat                                                20

<210> SEQ ID NO 103
<211> LENGTH: 20
<212> TYPE: DNA
<213> ORGANISM: Homo sapiens

<400> SEQUENCE: 103
tggcagccag ttctttgtgt                                                20

<210> SEQ ID NO 104
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 104
caccaacgaa acaccgatga ctgggttcaa gagacccagt catcggtgtt tcgtt          55

<210> SEQ ID NO 105
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 105
aaaaaacgaa acaccgatga ctgggtctct tgaacccagt catcggtgtt tcgtt          55

<210> SEQ ID NO 106
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 106
caccaatcac cggaccacac acacattcaa gagatgtgtg tgtggtccgg tgatt          55

<210> SEQ ID NO 107
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 107
aaaaaatcac cggaccacac acacatctct tgaatgtgtg tgtggtccgg tgatt          55

<210> SEQ ID NO 108
<211> LENGTH: 55
<212> TYPE: DNA
<213> ORGANISM: Artificial
```

```
<220> FEATURE:
<223> OTHER INFORMATION: Artificially synthesized target sequence for
      siRNA

<400> SEQUENCE: 108
caccaaacct tgcctacgac atgtttcaa gagaaacatg tcgtaggcaa ggttt          55

<210> SEQ ID NO 109
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 109
aaaaaaacct tgcctacgac atgtttctct tgaaaacatg tcgtaggcaa ggttt          55

<210> SEQ ID NO 110
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 110
caccaaaagg tttccgttag ccccgttcaa gagacggggc taacggaaac ctttt          55

<210> SEQ ID NO 111
<211> LENGTH: 55
<212> TYPE: DNA
<213> ORGANISM: Artificial
<220> FEATURE:
<223> OTHER INFORMATION: Artificially synthesized target sequence for
      siRNA

<400> SEQUENCE: 111
aaaaaaaagg tttccgttag ccccgtctct tgaacggggc taacggaaac ctttt          55
```

GENES AND POLYPEPTIDES RELATING TO HEPATOCELLULAR OR COLORECTAL CARCINOMA

The present application is a division of U.S. patent application Ser. No. 11/948,790, filed Nov. 30, 2007, which is a continuation of U.S. patent application Ser. No. 10/517,151, filed Aug. 18, 2005, which is a U.S. National Phase of International Application No. PCT/JP2003/07070, filed Jun. 4, 2003, which claims the benefit of U.S. Provisional Application No. 60/386,985, filed Jun. 6, 2002, all of which are incorporated herein by reference.

TECHNICAL FIELD

The present invention relates to the field of biological science, more specifically to the field of cancer research. In particular, the present invention relates to novel genes, WDRPUH, KRZFPUH, PPIL1, and APCDD1, involved in the proliferation mechanism of cells, as well as polypeptides encoded by the genes. The genes and polypeptides of the present invention can be used, for example, in the diagnosis of cell proliferative disease, and as target molecules for developing drugs against the disease.

BACKGROUND ART

Hepatocellular carcinoma (HCC) and colorectal carcinomas are leading causes of cancer death worldwide (Akriviadis et al., Br J Surg 85(10): 1319-31 (1998)). Although recent medical advances have made great progress in diagnosis and therapeutic strategies, a large number of patients with cancers are still diagnosed at advanced stages and their complete cures from the disease are matters of pressing concern. Recent advances in molecular studies have revealed that alteration of tumor suppressor genes and/or oncogenes are involved in carcinogenesis, however the precise mechanisms still remain to be elucidated.

Recent advances in molecular biology suggest that multistep processes underlie hepatocarcinogenesis as they do the genesis and progression of colon tumors. These processes involve qualitative and quantitative alterations of various gene products. The β-catenin/Tcf signaling pathway has been reported to be involved in morphogenesis during development (Wodarz and Nusse, Annu Rev Cell Dev Biol 14: 59-88 (1998); Polakis, Genes Dev 14: 1837-51 (2000); Bienz and Clevers, Cell 103: 311-20 (2000)). Recent progress in cancer research has underscored the importance of the signaling pathway in the development of human tumors, whether arising in the colon, liver, prostate, stomach, brain, endometrium, or elsewhere (Bullions and Levine, Curr Opin Oncol 10: 81-7 (1998)). Adenomatous polyposis coli (APC), a tumor suppressor, interacts with β-catenin, Axin, conductin, and glycogen synthase kinase-3β (GSK-3β) and facilitates the degradation of β-catenin via the ubiquitin-proteosome system (Polakis, Genes Dev 14: 1837-51 (2000)). Most sporadic colorectal tumors accumulate β-catenin in the cytoplasm and/or nucleus due to either the inactivating mutations in APC, AXIN1 or AXIN2 (conductin), or to stabilizing oncogenic mutations in CTNNB1 (β-catenin), which results in constitutive activation of β-catenin/Tcf transcriptional complex (Polakis, Genes Dev 14: 1837-51 (2000); Korinek et al., Science 275: 1784-7 (1997)). Consequently the complex activates target genes such as c-myc, cyclin D1, matrilysin (MMP-1), c-jun, fra-1, urokinase-type plasminogen activator receptor (uPAR), connexin43, CD44, PPAR-∂, AF-17 and ENC-1 (He et al., Science 281: 1509-12 (1998); Shtutman et al., Proc Natl Acad Sci USA 96: 5522-7 (1999); Brabletz et al., Am J Pathol 155: 1033-1038 (1999); Crawford et al., Oncogene 18: 2883-91 (1999); Mann et al., Proc Natl Acad Sci USA 96: 1603-8 (1999); van der Heyden et al., J Cell Sci 111: 1741-9 (1998); Wielenga et al., Am J Pathol 154: 515-23 (1999); He et al., Cell 99: 335-45 (1999); Lin et al. Cancer Res 61: 6345-9 (2001); Fujita et al., Cancer Res 61: 7722-6 (2001)). However, the precise mechanism of tumorgenesis by activation of this pathway in colorectal cancer remains to be solved.

Another protein, stathmin is also known to be associated with a wide range of cancers (Hanash et al., J Biol Chem 263: 12813-5 (1988); Roos et al., Leukemia 7: 1538-46 (1993); Nylander et al., Histochem J 27: 155-60 (1995); Friedrich et al., Prostate 27: 102-9 (1995); Bieche et al., Br J Cancer 78: 701-9 (1998)). Stathmin (Sobel et al., J Biol Chem 264: 3765-72 (1989); Sobel et al., Trends Biol Sci 16: 301-5 (1991)) is a cytosolic phosphorprotein consisting of 148 amino acid residues (19 kD) that has also been referred to as p19, prosolin, Lap18, oncoprotein 18, metablastin, and Op 18. The expression of stathmin was revealed to be very high in various multipotential embryonic carcinoma cells and in multipotential cells of the inner cell mass of the mouse blastocyst (Doge et al., Differentiation 50:89-96 (1992)). Stathmin exists in cells under several non-phosphorylated and phosphorylated forms, the pattern of which is depending on the state of proliferation, differentiation, or activation of the cells in many biological systems (Sobel et al., Trends Biol Sci 16: 301-5 (1991)). Further, the microtuble depolymerizing activity of stathmin is known to be regulated by the changes in its phosphorylation level, and the microtuble depolymerizing activity of stathmin is reported to play a critical role in the regulation of the dynamic instability of microtubles during the different phases of the cell cycle (Marklund et al., EMBO J15: 5290-8 (1996); Horwitz et al., J Biol Chem 272: 8129-31 (1997)). Extensive phosphorylation of stathmin occurs during mitosis (Strahler et al., Biochem Biophy Res Commun 185: 197-203 (1992); Luo et al., J Biol Chem 269: 10312-8 (1994); Brattsand et al., Eur J Biochem 220:359-68 (1994)) and seems essential for the progression of the cell cycle. However, the precise mechanism of the phosphorylation of stathmin and its relation to canceration remains to be elucidated.

cDNA microarray technologies have enabled to obtain comprehensive profiles of gene expression in normal and malignant cells (Okabe et al., Cancer Res 61: 2129-37 (2001); Lin et al., Oncogene 21: 4120-8 (2002); Hasegawa et al., Cancer Res 62: 7012-7 (2002)). This approach enables to disclose the complex nature of cancer cells, and helps to understand the mechanism of carcinogenesis. Identification of genes that are deregulated in tumors can lead to more precise and accurate diagnosis of individual cancers, and to develop novel therapeutic targets (Bienz and Clevers, Cell 103:311-20 (2000)). To disclose mechanisms underlying tumors from a genome-wide point of view, and discover target molecules for diagnosis and development of novel therapeutic drugs, the present inventors have been analyzing the expression profiles of tumor cells using a cDNA microarray of 23040 genes (Okabe et al., Cancer Res 61: 2129-37 (2001); Kitahara et al., Cancer Res 61: 3544-9 (2001); Lin et al., Oncogene 21: 4120-8 (2002); Hasegawa et al., Cancer Res 62: 7012-7 (2002)).

Studies designed to reveal mechanisms of carcinogenesis have already facilitated identification of molecular targets for anti-tumor agents. For example, inhibitors of farnexyltransferase (FTIs) which were originally developed to inhibit the growth-signaling pathway related to Ras, whose activation depends on posttranslational farnesylation, has been effective in treating Ras-dependent tumors in animal models (He et al., Cell 99: 335-45 (1999)). Clinical trials on human using a combination of anti-cancer drugs and anti-HER2 monoclonal antibody, trastuzumab, have been conducted to antagonize the proto-oncogene receptor HER2/neu; and have been achieving improved clinical response and overall survival of breast-cancer patients (Lin et al., Cancer Res 61: 6345-9 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (Fujita et al., Cancer Res 61: 7722-6 (2001)).

SUMMARY OF THE INVENTION

An object of the present invention is to provide novel proteins involved in the proliferation mechanism of hepatocellular or colorectal carcinoma cells and the genes encoding the proteins, as well as methods for producing and using the same in the diagnosis and treatment of hepatocellular carcinoma (HCC) or colorectal cancer.

To disclose the mechanism of hepatocellular and colorectal carcinogenesis and identify novel diagnostic markers and/or drug targets for the treatment of these tumors, the present inventors analyzed the expression profiles of genes in hepatocellular and colorectal carcinogenesis using a genome-wide cDNA microarray containing 23040 genes. From the pharmacological point of view, suppressing oncogenic signals is easier in practice than activating tumor-suppressive effects. Thus, the present inventors searched for genes that are up-regulated during hepatocellular and colorectal carcinogenesis.

Among the transcripts that were commonly up-regulated in hepatocellular carcinomas, novel human genes WDRPUH (WD40 repeat protein up-regulated in HCC) and KRZFPUH (Kruppel-type zinc finger protein up-regulated in HCC) were identified on chromosome band 17p13 and 16p11, respectively. Gene transfer of WDRPUH or KRZFPUH promoted proliferation of cells. Furthermore, reduction of WDRPUH or KRZFPUH expression by transfection of their specific antisense S-oligonucleotides inhibited the growth of HCC cells. Many anticancer drugs, such as inhibitors of DNA and/or RNA synthesis, metabolic suppressors, and DNA intercalators, are not only toxic to cancer cells but also for normally growing cells. However, agents suppressing the expression of WDRPUH and KRZFPUH may not adversely affect other organs due to the fact that normal expression of these genes are restricted to testis, and placenta and testis, respectively, and thus may be of great importance for treating cancer.

Further, among the transcripts that were commonly up-regulated in colorectal cancers, gene PPIL1 (Peptidyl prolyl isomerase-like 1) assigned at chromosomal band 6p21.1 was identified. In addition, immunoprecipitation assay revealed that PPIL1 protein associates with SNW1 (SKI interacting protein), a protein involved in transcriptional activity of vitamin D receptor, and stathmin, a cytosolic phosphorprotein involved in progression of the cell cycle. The present inventors also searched for genes regulating β-catenin/Tcf4 complex that is abnormally up-regulated in hepatomas and colorectal cancers, and identified a novel gene APCDD1 (Down-regulated by adenomatosis polyposis coli) assigned at chromosomal band 18p11.2. Its expression was reduced by the transduction of wild-type APC and elevated in a great majority of colon cancer tissues. Gene transfer of PPIL1 or APCDD1 promoted proliferation of cells that lacked endogenous expression of either of these genes. Furthermore, reduction of PPIL1 or APCDD1 expression by transfection of specific antisense S-oligonucleotides to PPIL1 or APCDD1 inhibited the growth of colorectal cancer cells.

Thus, the present invention provides isolated novel genes, WDRPUH, KRZFPUH, PPIL1, and APCDD1, which are candidates as diagnostic markers for cancer as well as promising potential targets for developing new strategies for diagnosis and effective anti-cancer agents. Further, the present invention provides polypeptides encoded by these genes, as well as the production and the use of the same. More specifically, the present invention provides the following:

The present application provides novel human polypeptides, WDRPUH, KRZFPUH, PPIL1, and APCDD1, or a functional equivalent thereof, that promotes cell proliferation and is up-regulated in cell proliferative diseases, such as HCC and colorectal carcinoma.

In a preferred embodiment, the WDRPUH polypeptide includes a putative 620 amino acid protein with 11 WD40 repeat domains encoded by the open reading frame of SEQ ID NO: 1. The WDRPUH polypeptide preferably includes the amino acid sequence set forth in SEQ ID NO: 2. The present application also provides an isolated protein encoded from at least a portion of the WDRPUH polynucleotide sequence, or polynucleotide sequences at least 15%, and more preferably at least 25% complementary to the sequence set forth in SEQ ID NO: 1.

On the other hand, in a preferred embodiment, the KRZFPUH polypeptide includes a putative 500 amino acid protein with homology to a rat gene zinc finger protein HIT-39 (GenBank Accession No. AF277902) and included a Krupple-type zinc finger domain (KRAB) encoded by the open reading frame of SEQ ID NO: 3. The KRZFPUH polypeptide preferably includes the amino acid sequence set forth in SEQ ID NO: 4. The present application also provides an isolated protein encoded from at least a portion of the KRZFPUH polynucleotide sequence, or polynucleotide sequences at least 15%, and more preferably at least 25% complementary to the sequence set forth in SEQ ID NO: 3.

Furthermore, in a preferred embodiment, the PPIL1 polypeptide includes a putative 166 amino acid protein showing 98.1% identity to Ppil1, 41.6% to PPIA, 57.4% to Cyp2, and 50% to CypE encoded by the open reading frame of SEQ ID NO: 5. The PPIL1 polypeptide preferably includes the amino acid sequence set forth in SEQ ID NO: 6. The present application also provides an isolated protein encoded from at least a portion of the PPIL1 polynucleotide sequence, or polynucleotide sequences at least 15%, and more preferably at least 25% complementary to the sequence set forth in SEQ ID NO: 5.

Furthermore, in a preferred embodiment, the APCDD1 polypeptide includes a putative 514 amino acid protein showing 31% identity to endo-1,4-beta-xylanase of *Themobacillus xylanilyticus* encoded by the open reading frame of SEQ ID NO: 7. The APCDD1 polypeptide preferably includes the amino acid sequence set forth in SEQ ID NO: 8. The present application also provides an isolated protein encoded from at least a portion of the APCDD1 polynucleotide sequence, or polynucleotide sequences at least 15%, and more preferably at least 25% complementary to the sequence set forth in SEQ ID NO: 7.

The present invention further provides novel human genes, WDRPUH and KRZFPUH, whose expressions are markedly elevated in a great majority of HCCs as compared to corresponding non-cancerous liver tissues. The isolated WDRPUH gene includes a polynucleotide sequence as described in SEQ ID NO: 1. In particular, the WDRPUH cDNA includes 2152 nucleotides that contain an open reading frame of 1860 nucleotides. The present invention further encompasses polynucleotides which hybridize to and which are at least 15%, and more preferably at least 25% complementary to the polynucleotide sequence set forth in SEQ ID NO: 1, to the extent that they encode a WDRPUH protein or a functional equivalent thereof. Examples of such polynucleotides are degenerates and allelic mutants of SEQ ID NO: 1. On the other hand, the isolated KRZFPUH gene includes a polynucleotide sequence as described in SEQ ID NO: 3. In particular, the KRZFPUH cDNA includes 2744 nucleotides that contain an open reading frame of 1500 nucleotides. The present invention further encompasses polynucleotides which hybridize to and which are at least 15%, and more preferably at least 25% complementary to the polynucleotide sequence set forth in SEQ ID NO: 3, to the extent that they encode a KRZFPUH protein or a functional equivalent thereof. Examples of such polynucleotides are degenerates and allelic mutants of SEQ ID NO: 3.

Furthermore, the present invention provides a novel human gene, PPIL1, whose expression is markedly elevated in a great majority of colorectal cancers as compared to corresponding non-cancerous tissues. The isolated PPIL1 gene includes a polynucleotide sequence as described in SEQ ID NO: 5. In particular, the PPIL1 cDNA includes 1734 nucleotides that contain an open reading frame of 498 nucleotides. The present invention further encompasses polynucleotides which hybridize to and which are at least 15%, and more preferably at least 25% complementary to the polynucleotide sequence set forth in SEQ ID NO: 5, to the extent that they encode a PPIL1 protein or a functional equivalent thereof. Examples of such polynucleotides are degenerates and allelic mutants of SEQ ID NO: 5.

Moreover, the present invention provides a novel human gene, APCDD1, whose expression is markedly elevated in a great majority of primary colon cancers as compared to corresponding non-cancerous tissues and down regulated in response to the transduction of wild-type APC1 into colon cancer cells. The isolated APCDD1 gene includes a polynucleotide sequence as described in SEQ ID NO: 7. In particular, the APCDD1 cDNA includes 2607 nucleotides that contain an open reading frame of 1542 nucleotides. The present invention further encompasses polynucleotides which hybridize to and which are at least 15%, and more preferably at least 25% complementary to the polynucleotide sequence set forth in SEQ ID NO: 7, to the extent that they encode a APCDD1 protein or a functional equivalent thereof. Examples of such polynucleotides are degenerates and allelic mutants of SEQ ID NO: 7.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1, 3, 5, or 7. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1, 3, 5, or 7. In the case of an isolated polynucleotide which is longer than or equivalent in length to the reference sequence, e.g., SEQ ID NO: 1, 3, 5, or 7, the comparison is made with the full length of the reference sequence. Where the isolated polynucleotide is shorter than the reference sequence, e.g., shorter than SEQ ID NO: 1, 3, 5, or 7, the comparison is made to segment of the reference sequence of the same length (excluding any loop required by the homology calculation).

The present invention also provides a method of producing a protein by transfecting or transforming a host cell with a polynucleotide sequence encoding the WDRPUH, KRZFPUH, PPIL1, or APCDD1 protein, and expressing the polynucleotide sequence. In addition, the present invention provides vectors comprising a nucleotide sequence encoding the WDRPUH, KRZFPUH, PPIL1, or APCDD1 protein, and host cells harboring a polynucleotide encoding the WDRPUH, KRZFPUH, PPIL1, or APCDD1 protein. Such vectors and host cells may be used for producing the WDRPUH, KRZFPUH, PPIL1, or APCDD1 protein.

An antibody that recognizes the WDRPUH, KRZFPUH, PPIL1, or APCDD1 protein is also provided by the present application. In part, an antisense polynucleotide (e.g., antisense DNA), ribozyme, and siRNA (small interfering RNA) of the WDRPUH, KRZFPUH, PPIL1, or APCDD1 gene is also provided.

The present invention further provides a method for diagnosis of cell proliferative diseases that includes determining an expression level of the gene in biological sample of specimen, comparing the expression level of WDRPUH, KRZFPUH, PPIL1, or APCDD1 gene with that in normal sample, and defining a high expression level of the WDRPUH, KRZFPUH, PPIL1, or APCDD1 gene in the sample as having a cell proliferative disease such as cancer. The disease diagnosed by the expression level of WDRPUH or KRZFPUH is suitably a hepatocellular carcinoma; and that detected by the expression level of PPIL1 or APCDD1 is colorectal carcinoma.

Further, a method of screening for a compound for treating a cell proliferative disease is provided. The method includes contacting the WDRPUH, KRZFPUH, PPIL1, or APCDD1 polypeptide with test compounds, and selecting test compounds that bind to the WDRPUH, KRZFPUH, PPIL1, or APCDD1 polypeptide.

The present invention further provides a method of screening for a compound for treating a cell proliferative disease, wherein the method includes contacting the WDRPUH, KRZFPUH, PPIL1, or APCDD1 polypeptide with a test compound, and selecting the test compound that suppresses the expression level or biological activity of the WDRPUH, KRZFPUH, PPIL1, or APCDD1 polypeptide.

Also provided is a method of screening for a compound for treating a cell proliferative disease, wherein the method includes contacting a test compound, β-catenin/Tcf 4 complex, and a reporter gene with a transcriptional regulatory region of APCDD1 comprising the two Tcf/LEF binding motifs under a suitable condition for the expression of the reporter gene, and selecting the test compound that inhibits the expression of the reporter gene.

Furthermore, the present invention provides a method of screening for a compound for treating a cell proliferative disease, wherein the method includes contacting PPIL1 and stathmin or SNW1 in the presence of a test compound, and selecting the test compound that inhibits the binding of PPIL1 and stathmin or SNW1.

The present application also provides a pharmaceutical composition for treating cell proliferative disease, such as cancer. The pharmaceutical composition may be, for example, an anti-cancer agent. The pharmaceutical composition can be described as at least a portion of the antisense S-oligonucleotides or siRNA of the WDRPUH, KRZFPUH, PPIL1, or APCDD1 polynucleotide sequence shown and described in SEQ ID NO: 1, 3, 5, or 7, respectively. A suitable antisense S-oligonucleotide has the nucleotide sequence selected from the group of SEQ ID NO: 16, 37, 44, or 89. The antisense S-oligonucleotide of WDRPUH including those having the nucleotide sequence of SEQ ID NO: 16 may be suitably used to treat hepatoma, and gastric cancer; the antisense S-oligonucleotide of KRZFPUH including those having the nucleotide sequence of SEQ ID NO: 37 suitably to treat hepatoma, gastric cancer, and lung cancer; the antisense S-oligonucleotide of PPIL1 including those having the nucleotide sequence of SEQ ID NO: 44 suitably for colon cancer; and the antisense S-oligonucleotide of APCDD1 including those having the nucleotide sequence of SEQ ID NO: 89 suitably for colorectal carcinoma. The pharmaceutical compositions may be also those comprising the compounds selected by the present methods of screening for compounds for treating cell proliferative diseases.

The course of action of the pharmaceutical composition is desirably to inhibit growth of the cancerous cells. The pharmaceutical composition may be applied to mammals including humans and domesticated mammals.

The present invention further provides methods for treating a cell proliferative disease using the pharmaceutical composition provided by the present invention.

In addition, the present invention provides method for treating or preventing cancer, which method comprises the step of administering the WDRPUH, KRZFPUH, PPIL1, or APCDD1 polypeptide. It is expected that anti tumor immunity be induced by the administration of the WDRPUH, KRZFPUH, PPIL1, or APCDD1 polypeptide. Thus, the present invention also provides method for inducing anti tumor immunity, which method comprises the step of administering the WDRPUH, KRZFPUH, PPIL1, or APCDD1 polypeptide, as well as pharmaceutical composition for treating or preventing cancer comprising the WDRPUH, KRZFPUH, PPIL1, or APCDD1 polypeptide.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 1a depicts the relative expression ratios (cancer/non-cancer) of WDRPUH in 20 HCCs examined by cDNA microarray. Its expression was up-regulated (Cy3:Cy5 intensity ratio, >2.0) in 11 of the 12 HCCs that passed through the cutoff filter (both Cy3 and Cy5 signals greater than 25,000). FIG. 1b depicts the relative expression ratios (cancer/non-cancer) of KRZFPUH in the 20 HCCs. Its expression was up-regulated (Cy3:Cy5 intensity ratio, >2.0) in 11 of the 14 HCCs that passed through the cutoff filter. FIGS. 1c and 1d present photographs depicting the expression of WDRPUH (c) and KRZFPUH (d) analyzed by semi-quantitative RT-PCR using additional 10 HCC cases (T, tumor tissue; N, normal tissue). Expression of GAPDH served as an internal control.

FIG. 2a is a photograph depicting the expression of WDRPUH in various human tissues analyzed by multiple-tissue northern blot analysis. FIG. 2b depicts the predicted protein structure of WDRPUH.

FIG. 4a is a photograph depicting the result of a colony formation assay of NIH3T3 cells transfected with WDRPUH, antisense against WDRPUH, and the vector alone. FIG. 4b depicts the number of colonies counted by electric densitometry. A (*) denotes a significant difference ($p<0.05$) from control cells as determined by a Student's t test.

FIG. 5a presents photographs depicting the expression of WDRPUH and GAPDH (control) in SNU475 cells treated with either sense (WDRPUH-S4) or antisense (WDRPUH-AS4) oligonucleotides for 12 h. FIG. 5b depict the cell viability of SNU475 cells 72 h after oligonucleotide treatment measured by MTT assay.

FIG. 6A presents photographs depicting the expression of WDRPUH and GAPDH (control) in HepG2 cells transfected with WDRPUH-siRNAs. FIG. 6B presents photographs depicting the result of Giemsa's staining of viable cells treated with control-siRNAs or WDRPUH-siRNAs.

FIG. 8a is a photograph depicting the expression of KRZFPUH in various human tissues analyzed by multiple-tissue northern blot analysis. FIG. 8b depicts the predicted protein structure of KRZFPUH.

FIG. 10a is a photograph depicting the result of a colony formation assay of COS7 cells transfected with KRZFPUH, and antisense against KRZFPUH. FIG. 10b depicts the number of colonies counted by electric densitometry. A (*) denotes a significant difference ($p<0.05$) from control cells as determined by a Student's t test.

FIG. 11a presents photographs depicting the expression of WDRPUH and GAPDH (control) in Alexander cells transfected with sense (KRZFPUH-S4) or antisense (KRZF-PUH-AS4) oligonucleotides. FIG. 11b depicts the expression of KRZFPUH in SNU475 cells treated with either KRZF-PUH-S4 or KRZFPUH-AS4 for 12 h. A (*) denotes a significant difference (p<0.05) from control cells as determined by a Student's t test.

FIG. 12A depicts the result of semiquantitative RT-PCR carried out using RNA extracted from Huh7 cells transfected with psiU6BX-KRZFPUH2 (Si-02), psiU6BX-EGFP (EGFP), or mock vector (Mock). GAPDH served as an internal control. FIG. 12B depicts the result of MTT assay of viable cells transfected with control plasmid (Mock and EGFP) or plasmids expressing KRZFPUH-siRNAs at Day5 of transfection. A (*) denotes a significant difference (p<0.01) as determined by a Fisher's protected least significant difference test. FIG. 12C depicts the result of MTT assay of viable cells transfected with control plasmid (Mock and EGFP) or psiU6BX-KRZFPUH2 (Si-02) at Day10 of transfection. A (*) denotes a significant difference (p<0.01) as determined by a Fisher's protected least significant difference test. FIG. 12D presents photographs depicting the result of Giemsa's staining of viable cells transfected with control plasmid (Mock and EGFP) or psiU6BX-KRZFPUH2 (Si-02) at Day10 of transfection.

FIG. 13A depicts the result of MTT assay carried out using Alexander cells transfected with control plasmid (Mock and EGFP) or psiU6BX-KRZFPUH2 (Si-02) at Day10 of transfection. FIG. 13B depicts the effect of MTT assay carried out using SNU449 cells transfected with control plasmid (Mock and EGFP) or psiU6BX-KRZF-PUH2 (Si-02) at Day10 of transfection. FIG. 13C depicts the effect of KRZFPUH-siRNAs on the viability of HepG2 cells measured by MTT assay. A (*) denotes significant difference (p<0.01) as determined by a Fisher's protected least significant difference test.

FIG. 14a depicts the relative expression ratio (cancer/non-cancer) of PPIL1 in 11 colon cancer cases examined by cDNA microarray. Its expression was up-regulated (Cy3:Cy5 intensity ratio, >2.0) in 6 of the 6 cases that passed through the cutoff filter. FIG. 14b presents photographs depicting the expression of PPIL1 analyzed by semi-quantitative RT-PCR using additional 20 colon cancer cases (T, tumor tissue; N, normal tissue). Expression of GAPDH served as an internal control.

FIG. 16a is a photograph depicting the result of a colony formation assay of NIH3T3 cells transfected with PPIL1. FIG. 16b is a photograph depicting the result of a colony formation assay of HCT116 cells transfected with PPIL1. In both experiments, pcDNA-LacZ and pcDNA3.1-antisense expressing complementary strand of the coding region of PPIL1 served as negative controls.

FIG. 17a presents photographs depicting the expression of PPIL1 and GAPDH (control) in SW480 cells treated with sense (PPIL1-S2), antisense (PPIL1-AS2), or scramble (PPIL1-SCR2) S-oligonucleotides. FIG. 17b is a photograph depicting the growth suppressive effect of PPIL1-AS2. FIG. 17c depicts the cell viability of SE480, SNUC4, and SNUC5 cells 72 h after oligonucleotides treatment measured by MTT assay.

FIG. 19a is a photograph of COS7 cells transfected with pFLAG CMV-PPIL1 and stained with anti-FLAG M2 monoclonal antibody. The tagged protein was visualized using anti mouse IgG antibody labeled with Rhodamine. FIG. 19b is a photograph of COS7 cells transfected with pcDNA3.1myc/His-SNW1 and stained with anti c-Myc antibody. The tagged protein was visualized by anti rabbit IgG antibody labeled with FITC. FIG. 19c is a photograph of the cells wherein the nuclei were counter-stained with DAPI. FIG. 19d is a merged image of (a), (b) and (c). PPIL1 and SNW1 were co-localized in the nucleus.

FIG. 21A presents photographs depicting the expression of PPIL1 and GAPDH (control) in SNUC4 and SNUC5 cells transfected with PPIL1-siRNAs. FIG. 21B presents photographs depicting the result of Giemsa's staining of viable cells treated with control-siRNAs or PPIL1-siRNAs.

FIG. 22A is a photograph depicting the expression of GST-fused PPIL1 protein. FIG. 22B is a photograph depicting the expression of His-tagged PPIL1 protein.

FIG. 23A is a photograph depicting the interaction of PPIL1 with stathmin in the two-hybrid system. FIG. 23B is a photograph depicting the interaction of PPIL1 with stathmin in vivo.

FIG. 24 present photographs depicting the result of fluorescent immunohistochemical staining of PPIL1 and stathmin in the cytoplasms of COS7 cells.

FIG. 25A shows schematic illustrations of the structure of various deletion mutants of stathmin. FIG. 25B presents photographs depicting the expression of stathmin and co-precipitation of PPIL1 with the deletion mutants in vivo.

FIG. 26A shows a schematic illustration of stathmin mutants wherein Ser was substituted with Ala. FIG. 26B presents photographs depicting the expression of stathmin and co-precipitation of PPIL1 with the mutants in vivo.

FIG. 27a presents photographs demonstrating the decrease in the expression of APCDD1 in SW480 cells transfected with either Ad-APC or Ad-Axin. RNAs and protein extracts were isolated from the SW480 cells infected with the indicated adenoviruses at MOI100 and incubated for 72 hours. FIG. 27b is a photograph depicting the expression of APCDD1 in adult human tissues analyzed by Northern blotting. APCDD1 is predominantly expressed in heart, pancreas, prostate and ovary but scarcely expressed in lung, liver, kidney, spleen, thymus, colon, and peripheral blood cells. FIG. 27c presents photographs showing the expression of APCDD1 in colon-cancer tissues (T) and corresponding non-cancerous mucosae (N) measured by semiquantitative RT-PCR. Increased expression was observed in 20 of the 30 cases examined (67%). Expression of GAPDH served as the internal control.

FIG. 28a is a schematic illustration showing putative Tcf4-binding elements in the 5' flanking region of APCDD1 and various reporter plasmids of APCDD1. The nucleotide positions from the putative transcription-initiating site are indicated with plus or minus number. FIG. 28b depicts the luciferase activity of HeLa cells that were co-transfected with the reporter plasmids and expression plasmids (pcDNA-mock, pcDNA-mut β-catenin, pcDNA-wtTcf-4, or pcDNA-dnTcf4) in various combinations. The reporter assay was carried out in triplicate 48 hours after transfection. Bars, SD. A (*) denotes significant difference (P<0.01) as determined by a Scheffé's F test.

FIG. 30a is a photograph showing the result of a colony-formation assay in LoVo cells. The cells were transfected with pcDNA3.1-APCDD1, pcDNA, or pcDNA-antisense. FIG. 30b is a photograph demonstrating the expression of APCDD1 in LoVo cells that express exogenous APCDD1 (LoVo-APCDD1) and control (LoVo-vector) cells. FIG. 30c depicts the growth of LoVo-APCDD1 and LoVo-vector cells. FIG. 30d depicts the growth of tumor in two clones of LoVo-APCDD1 cells and two clones of LoVo-vector cells in nude mice.

FIG. 31A presents photographs depicting the expression of APCDD1 in SW480 cells treated with sense (APCDD-S2) or antisense (APCDD-AS2) S-oligonucleotides for 24 hours. The expression of GAPDH served as an internal control. FIG. 31B is a photograph depicting the growth suppressive effect of APCDD-AS2. FIG. 31C depicts the cell viability of SW480 cells after oligonucleotide treatment measured by MTT assay. Bars, SD. A (*) denotes significant difference (P<0.01) as determined by a Scheffé's F test.

DETAILED DESCRIPTION OF THE INVENTION

Figure 1:
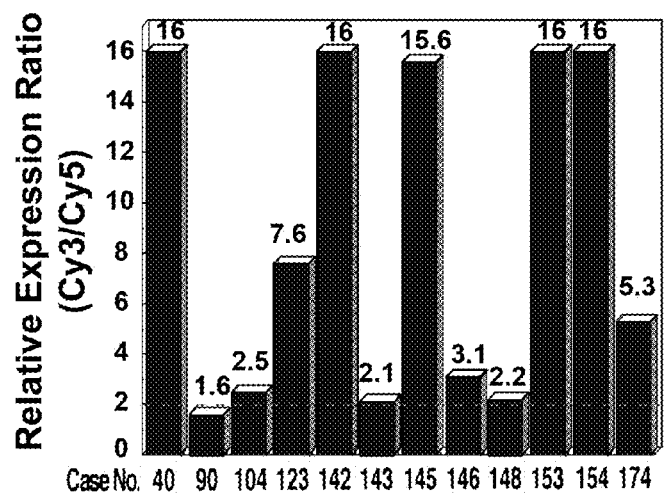
FIGS. 1a to 1d depict the expression of WDRPUH and KRZFPUH in HCCs.
Figure 1:
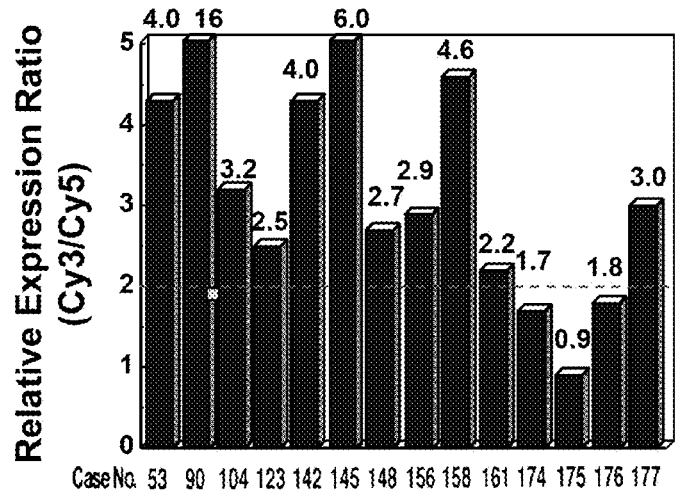
Figure 1:
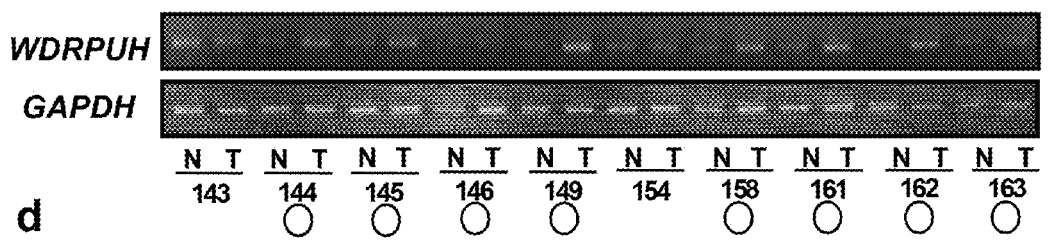
Figure 1:
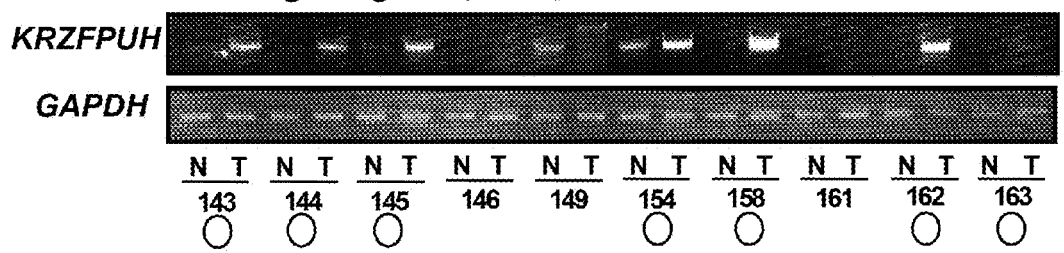

The words "a", "an", and "the" as used herein mean "at least one" unless otherwise specifically indicated.

The present application identifies novel human genes WDRPUH and KRZFPUH whose expression is markedly elevated in HCCs compared to corresponding non-cancerous liver tissues. The WDRPUH cDNA consists of 2152 nucleotides that contain an open reading frame of 1860 nucleotides as set forth in SEQ ID NO: 1. The open reading frame encodes a putative 620-amino acid protein with 11 WD40 repeats domains. Therefore this protein has been named WDRPUH (WD40 repeats protein up-regulated in HCCs). On the other hand, the KRZFPUH cDNA consists of 2744 nucleotides that contain an open reading frame of 1500 nucleotides as set forth in SEQ ID NO: 3. The open reading frame encodes a putative 500-amino acid protein containing a Kruppel-type zinc finger domain. Therefore this protein has been named KRZFPUH (Krupple-type zinc finger protein up-regulated in HCCs).

Furthermore, the present invention encompasses novel human genes PPIL1 and APCDD1 whose expression is markedly elevated in colorectal cancer compared to corresponding non-cancerous tissue. The PPIL1 cDNA consists of 1734 nucleotides that contain an open reading frame of 498 nucleotides as set forth in SEQ ID NO: 5. The open reading frame encodes a putative 166-amino acid protein. PPIL1 directly associates with a SKI interacting protein (SNW1), a protein involved in transcriptional activity of vitamin D receptor, and stathmin, a cytosolic phosphorprotein involved in the progression of the cell cycle. On the other hand the APCDD1 cDNA consists of 2607 nucleotides that contain an open reading frame of 1542 nucleotides as set forth in SEQ ID NO: 7. The open reading frame encodes a putative 514-amino acid protein with no known motif. The gene was dubbed APCDD1 (down-regulated by APC 1). Furthermore, the expression of APCDD1 is enhanced by the β-catenin/Tcf 4 complex through the binging of the complex to the two Tcf/LEF binding motifs in the transcriptional regulatory region of APCDD1.

Consistently, exogenous expression of WDRPUH, KRZFPUH, PPIL1, or APCDD1 into cells conferred increased cell growth, while suppression of its expression with antisense S-oligonucleotides or small interfering RNA (siRNA) resulted in a significant growth-inhibition of cancerous cells. These findings suggest that WDRPUH, KRZFPUH, PPIL1, and APCDD1 render oncogenic activities to cancer cells, and that inhibition of the activity of these proteins could be a promising strategy for the treatment of cancer.

The present invention encompasses novel human gene WDRPUH, including a polynucleotide sequence as described in SEQ ID NO: 1, as well as degenerates and mutants thereof, to the extent that they encode a WDRPUH protein, including the amino acid sequence set forth in SEQ ID NO: 2 or its functional equivalent. Examples of polypeptides functionally equivalent to WDRPUH include, for example, homologous proteins of other organisms corresponding to the human WDRPUH protein, as well as mutants of human WDRPUH proteins.

The present invention also encompasses novel human gene KRZFPUH, including a polynucleotide sequence as described in SEQ ID NO: 3, as well as degenerates and mutants thereof, to the extent that they encode a KRZFPUH protein, including the amino acid sequence set forth in SEQ ID NO: 4 or its functional equivalent. Examples of polypeptides functionally equivalent to KRZFPUH include, for example, homologous proteins of other organisms corresponding to the human KRZFPUH protein, as well as mutants of human KRZFPUH proteins.

Furthermore, the present invention encompasses novel human gene PPIL1, including a polynucleotide sequence as described in SEQ ID NO: 5, as well as degenerates and mutants thereof, to the extent that they encode a PPIL1 protein, including the amino acid sequence set forth in SEQ ID NO: 6 or its functional equivalent. Examples of polypeptides functionally equivalent to PPIL1 include, for example, homologous proteins of other organisms corresponding to the human PPIL1 protein, as well as mutants of human PPIL1 proteins.

The present invention further encompasses novel human gene APCDD1, including a polynucleotide sequence as described in SEQ ID NO: 7, as well as degenerates and mutants thereof, to the extent that they encode a APCDD1 protein, including the amino acid sequence set forth in SEQ ID NO: 8 or its functional equivalent. Examples of polypeptides functionally equivalent to APCDD1 include, for example, homologous proteins of other organisms corresponding to the human APCDD1 protein, as well as mutants of human APCDD1 proteins.

In the present invention, the term "functionally equivalent" means that the subject polypeptide has the activity to promote cell proliferation like WDRPUH, KRZFPUH, PPIL1, or APCDD1 protein and to confer oncogenic activity to cancer cells. Whether the subject polypeptide has a cell proliferation activity or not can be judged by introducing a DNA encoding the subject polypeptide into a cell expressing the respective polypeptide, and detecting promotion of proliferation of the cells or increase in colony forming activity. Such cells include, for example, NIH3T3, SNU475, and HepG2 for WDRPUH; COS7, and Alexander cells for KRZFPUH; NIH3T3, HCT 116, SW480, SNU-C4, and SNU-C5 for PPIL1; and LoVo cells, and SW480 for APCDD1. Alternatively, whether the subject polypeptide is functionally equivalent to PPIL1 may be judged by detecting its binding ability to SNW1 or stathmin.

Methods for preparing polypeptides functionally equivalent to a given protein are well known by a person skilled in the art and include known methods of introducing mutations into the protein. For example, one skilled in the art can prepare polypeptides functionally equivalent to the human WDRPUH, KRZFPUH, PPIL1, or APCDD1 protein by introducing an appropriate mutation in the amino acid sequence of either of these proteins by site-directed mutagenesis (Hashimoto-Gotoh et al., Gene 152: 271-275 (1995); Zoller and Smith, Methods Enzymol 100: 468-500 (1983); Kramer et al., Nucleic Acids Res. 12: 9441-9456 (1984); Kramer and Fritz, Methods Enzymol 154: 350-367 (1987); Kunkel, Proc Natl Acad Sci USA 82: 488-492 (1985); Kunkel, Methods Enzymol 85: 2763-2766 (1988)). Amino acid mutations can occur in nature, too. The polypeptide of the present invention includes those proteins having the amino acid sequences of the human WDRPUH, KRZFPUH, PPIL1, or APCDD1 protein in which one or more amino acids are mutated, provided the resulting mutated polypeptides are functionally equivalent to the human WDRPUH, KRZFPUH, PPIL1, or APCDD1 protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-5666 (1984); Zoller and Smith, Nucleic Acids Res 10: 6487-6500 (1982); Dalbadie-McFarland et al., Proc Natl Acad Sci USA 79: 6409-6413 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of human WDRPUH, KRZFPUH, PPIL1, or APCDD1 protein is a fusion protein containing the human WDRPUH, KRZFPUH, PPIL1, or APCDD1 protein. Fusion proteins are, fusions of the human WDRPUH, KRZFPUH, PPIL1, or APCDD1 protein and other peptides or proteins, and are included in the present invention. Fusion proteins can be made by techniques well known to a person skilled in the art, such as by linking the DNA encoding the human WDRPUH, KRZFPUH, PPIL1, or APCDD1 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-1210 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human WDRPUH, KRZFPUH, PPIL1, or APCDD1 protein (i.e., SEQ ID NO: 1, 3, 5, or 7), and isolate functionally equivalent polypeptides to the human WDRPUH, KRZFPUH, PPIL1, or APCDD1 protein from the isolated DNA. The polypeptides of the present invention include those that are encoded by DNA that hybridize with a whole or part of the DNA sequence encoding the human WDRPUH, KRZFPUH, PPIL1, or APCDD1 protein and are functionally equivalent to the human WDRPUH, KRZFPUH, PPIL1, or APCDD1 protein. These polypeptides include mammal homologues corresponding to the protein derived from human (for example, a polypeptide encoded by a monkey, rat, rabbit, and bovine gene). In isolating a cDNA highly homologous to the DNA encoding the human WDRPUH protein from animals, it is particularly preferable to use tissues from testis. Alternatively, in isolating a cDNA highly homologous to the DNA encoding the human KRZFPUH from animals, it is particularly preferable to use tissues from placenta or testis. Further, in isolating a cDNA highly homologous to the DNA encoding the human PPIL1 protein from animals, it is particularly preferable to use tissues from heart, skeletal muscle, testis, thyroid, or adrenal gland; and in isolating that to the DNA encoding the human APCDD1 protein, preferably tissue from heart, pancreas, prostate, ovary, lung, liver, kidney, spleen, thymus, colon, or peripheral leukocyte, and particularly preferably tissue from heart, pancreas, prostate, or ovary is used.

The condition of hybridization for isolating a DNA encoding a polypeptide functionally equivalent to the human WDRPUH, KRZFPUH, PPIL1, or APCDD1 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human WDRPUH, KRZFPUH, PPIL1, or APCDD1 protein, using a primer synthesized based on the sequence information of the protein encoding DNA (SEQ ID NO: 1, 3, 5, or 7).

Polypeptides that are functionally equivalent to the human WDRPUH, KRZFPUH, PPIL1, or APCDD1 protein encoded by the DNA isolated through the above hybridization techniques or gene amplification techniques, normally have a high homology to the amino acid sequence of the human WDRPUH, KRZFPUH, PPIL1, or APCDD1 protein. "High homology" typically refers to a homology of 40% or higher, preferably 60% or higher, more preferably 80% or higher, even more preferably 95% or higher. The homology of a polypeptide can be determined by following the algorithm in "Wilbur and Lipman, Proc Natl Acad Sci USA 80:726-730 (1983)".

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human WDRPUH, KRZFPUH, PPIL1, or APCDD1 protein of the present invention, it is within the scope of the present invention.

The polypeptides of the present invention can be prepared as recombinant proteins or natural proteins, by methods well known to those skilled in the art. A recombinant protein can be prepared by inserting a DNA, which encodes the polypeptide of the present invention (for example, the DNA comprising the nucleotide sequence of SEQ ID NO: 1, 3, 5, or 7), into an appropriate expression vector, introducing the vector into an appropriate host cell, obtaining the extract, and purifying the polypeptide by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the polypeptide of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines, or FLAG, it can be detected and purified using antibodies to c-myc, His, or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the WDRPUH, KRZFPUH, PPIL1, or APCDD1 protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for accelerators or inhibitors of the polypeptide of the present invention.

A partial peptide of the invention can be produced by genetic engineering, by known methods of peptide synthesis, or by digesting the polypeptide of the invention with an appropriate peptidase. For peptide synthesis, for example, solid phase synthesis or liquid phase synthesis may be used.

Furthermore, the present invention provides polynucleotides encoding the polypeptide of the present invention. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention include a DNA comprising given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 1, 3, 5, or 7) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 1, 3, 5, or 7), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue, or organ (e.g., testis for WDRPUH; placenta or testis for KRZFPUH; heart, skeletal muscle, testis, thyroid, or adrenal gland for PPIL1; and heart, pancreas, prostate, ovary, lung, liver, kidney, spleen, thymus, colon, or peripheral leukocyte, preferably, heart, pancreas, prostate, or ovary for APCDD1) in which the object polypeptide of the invention is expressed. Known methods can be used to isolate mRNAs; for instance, total RNA may be prepared by the guanidine ultracentrifugation (Chirgwin et al., Biochemistry 18: 5294-5299 (1979)) or the AGPC method (Chomczynski and Sacchi, Anal Biochem 162: 156-159 (1987)). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyaysky et al., Nucleic Acids Res 17: 2919-2932 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA, or TAG).

Specifically, the polynucleotide of the present invention encompasses the DNA comprising the nucleotide sequence of SEQ ID NO: 1, 3, 5, or 7.

Furthermore, the present invention provides a polynucleotide that hybridizes under stringent conditions with a polynucleotide having a nucleotide sequence of SEQ ID NO: 1, 3, 5, or 7, and encodes a polypeptide functionally equivalent to the WDRPUH, KRZFPUH, PPIL1, or APCDD1 protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

The present invention also provides a vector into which a polynucleotide of the present invention is inserted. A vector of the present invention is useful to keep a polynucleotide, especially a DNA, of the present invention in host cell, to express the polypeptide of the present invention, or to administer the polynucleotide of the present invention for gene therapy.

When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5α, HB101, or XL1 Blue, are used as a host cell, the vector should have a promoter, for example, lacZ promoter (Ward et al., Nature 341: 544-546 (1989); FASEB J 6: 2422-2427 (1992)), araB promoter (Better et al., Science 240: 1041-1043 (1988)), or T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the E. coli is the pclB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01), and expression vectors derived from *Bacillus subtilis* (e.g., pPL608, pKTH50) can be used for producing the polypeptide of the present invention.

In order to express the vector in animal cells, such as CHO, COS, or NIH3T3 cells, the vector should have a promoter necessary for expression in such cells, for example, the SV40 promoter (Mulligan et al., Nature 277:108 (1979)), the MMLV-LTR promoter, the EF1α promoter (Mizushima et al., Nucleic Acids Res 18:5322 (1990)), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells, and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and so on.

The present invention provides an antibody that binds to the polypeptide of the invention. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies, and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention. Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates, or a chemically synthesized polypeptide may be used as the antigen.

Any mammalian animal may be immunized with the antigen, but preferably the compatibility with parental cells used for cell fusion is taken into account. In general, animals of Rodentia, Lagomorpha, or Primates are used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells, or their lysates in vitro. Then, the immunized lymphocytes are fused with human-derived myeloma cells that are capable of indefinitely dividing, such as U266, to yield a hybridoma producing a desired human antibody that is able to bind to the polypeptide (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography, or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells, or their lysates. Antibody producing cells are then collected from the animals and fused with myeloma cells to obtain hybridoma, from which human antibodies against the polypeptide can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, F(ab')$_2$, Fv, or single chain Fv (scFv), in which Fv fragments from H and L chains are ligated by an appropriate linker (Huston et al., Proc Natl Acad Sci USA 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J Immunol 152: 2968-2976 (1994); Better and Horwitz, Methods Enzymol 178:476-496 (1989); Pluckthun and Skerra, Methods Enzymol 178: 497-515 (1989); Lamoyi, Methods Enzymol. 121: 652-663 (1986); Rousseaux et al., Methods Enzymol 121: 663-669 (1986); Bird and Walker, Trends Biotechnol 9: 132-137 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared using known technology.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto. A protein A column and a protein G column can be used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC, and FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as a polypeptide. BIAcore (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

The present invention also provides a polynucleotide which hybridizes with the polynucleotide encoding human WDRPUH, KRZFPUH, PPIL1, or APCDD1 protein (SEQ ID NO: 1, 3, 5, or 7) or the complementary strand thereof, and which comprises at least 15 nucleotides. The polynucleotide of the present invention is preferably a polynucleotide which specifically hybridizes with the DNA encoding the polypeptide of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides, and nucleotide derivatives (for example, antisense oligonucleotides, and ribozymes), which specifically hybridize with DNA encoding the polypeptide of the invention or its complementary strand. Moreover, such polynucleotide can be utilized for the preparation of DNA chip.

The present invention includes an antisense oligonucleotide that hybridizes with any site within the nucleotide sequence of SEQ ID NO: 1, 3, 5, or 7. This antisense oligonucleotide is preferably against at least 15 continuous nucleotides of the nucleotide sequence of SEQ ID NO: 1, 3, 5, or 7. The above-mentioned antisense oligonucleotide, which contains an initiation codon in the above-mentioned at least 15 continuous nucleotides, is even more preferred. More specifically, such antisense oligonucleotides include those comprising the nucleotide sequence of SEQ ID NO: 16 for suppressing the expression of WDRPUH; SEQ ID NO: 37 for KRZFPUH; SEQ ID NO: 44 for PPIL1; and SEQ ID NO: 89 for APCDD1.

Derivatives or modified products of antisense oligonucleotides can be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 1, 3, 5, or 7.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the polypeptide of the invention as stated in a later example or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA, and inhibiting the expression of the polypeptide of the invention, thereby resulting in the inhibition of the polypeptide's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops, and freeze-drying agents by adding excipients, isotonic agents, solubilizers, stabilizers, preservatives, pain-killers, and such. These can be prepared by following usual methods.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin, or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The present invention also includes an siRNA comprising a combination of a sense strand nucleic acid and an antisense strand nucleic acid of the nucleotide sequence of SEQ ID NO: 1, 3, 5, or 7. By the term "siRNA" is meant a double stranded RNA molecule which prevents translation of a target mRNA. Standard techniques of introducing siRNA into the cell are used, including those in which DNA is a template from which RNA is transcribed. The siRNA comprises a sense nucleic acid sequence and an anti-sense nucleic acid sequence of the polynucleotide encoding human WDRPUH, KRZFPUH, PPIL1, or APCDD1 protein (SEQ ID NO: 1, 3, 5, or 7). The siRNA is constructed such that a single transcript has both the sense and complementary antisense sequences from the target gene, e.g., a hairpin.

The method is used to alter gene expression in a cell in which expression of WDRPUH, KRZFPUH, PPIL1, or APCDD1 are up-regulated, e.g., as a result of malignant transformation of the cells. Binding of the siRNA to WDRPUH, KRZFPUH, PPIL1, or APCDD1 transcript in the target cell results in a reduction in the protein production by the cell. The length of the oligonucleotide is at least 10 nucleotides and may be as long as the naturally-occurring transcript. Preferably, the oligonucleotide is 19-25 nucleotides in length. Most preferably, the oligonucleotide is less than 75, 50, or 25 nucleotides in length. Examples of WDRPUH, KRZFPUH, PPIL1, or APCDD 1 siRNA oligonucleotides which inhibit the expression in mammalian cells include oligonucleotides containing any of SEQ ID NO: 93-103. These sequences are target sequence of the following siRNA sequences respectively.

SEQ ID NO: 93, SEQ ID NOs: 24 and 25 (WDRPUH);
SEQ ID NO: 94, SEQ ID NOs: 26 and 27 (WDRPUH);
SEQ ID NO: 95, SEQ ID NOs: 28 and 29 (WDRPUH);
SEQ ID NO: 96, SEQ ID NOs: 30 and 31 (WDRPUH);
SEQ ID NO: 97, SEQ ID NOs: 104 and 105 (KRZFPUH);
SEQ ID NO: 98, SEQ ID NOs: 106 and 107 (KRZFPUH);
SEQ ID NO: 99, SEQ ID NOs: 108 and 109 (KRZFPUH);
SEQ ID NO: 100, SEQ ID NOs: 110 and 111 (KRZFPUH);
SEQ ID NO: 101, SEQ ID NOs: 47 and 48 (PPIL1);
SEQ ID NO: 102, SEQ ID NOs: 49 and 50 (PPIL1); and
SEQ ID NO: 103, SEQ ID NOs: 51 and 52 (PPIL1).

The nucleotide sequence of the siRNAs were designed using an siRNA design computer program available from the Ambion website (see the world wide web at ambion.com/ techlib/misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/.
3. Select qualifying target sequences for synthesis. At Ambion, preferably several target sequences can be selected along the length of the gene for evaluation.

The antisense oligonucleotide or siRNA of the invention inhibit the expression of the polypeptide of the invention and is thereby useful for suppressing the biological activity of the polypeptide of the invention. Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as cancer.

Moreover, the present invention provides a method for diagnosing a cell proliferative disease using the expression level of the polypeptides of the present invention as a diagnostic marker.

This diagnosing method comprises the steps of: (a) detecting the expression level of the WDRPUH, KRZFPUH, PPIL1, or APCDD1 gene of the present invention; and (b) relating an elevation of the expression level to the cell proliferative disease, such as cancer.

The expression levels of the WDRPUH, KRZFPUH, PPIL1, or APCDD1 gene in a particular specimen can be estimated by quantifying mRNA corresponding to or protein encoded by the WDRPUH, KRZFPUH, PPIL1, or APCDD1 gene. Quantification methods for mRNA are known to those skilled in the art. For example, the levels of mRNAs corresponding to the WDRPUH, KRZFPUH, PPIL1, or APCDD1 gene can be estimated by Northern blotting or RT-PCR. Since the full-length nucleotide sequences of the WDRPUH, KRZFPUH, PPIL1, and APCDD1 genes are shown in SEQ ID NO:1, 3, 5, or 7, anyone skilled in the art can design the nucleotide sequences for probes or primers to quantify the WDRPUH, KRZFPUH, PPIL1, or APCDD1 gene.

Also the expression level of the WDRPUH, KRZFPUH, PPIL1, or APCDD1 gene can be analyzed based on the activity or quantity of protein encoded by the gene. A method for determining the quantity of the WDRPUH, KRZFPUH, PPIL1, or APCDD1 protein is shown below. For example, immunoassay method is useful for the determination of proteins in biological materials. Any biological material can be used for the determination of the protein or it's activity. For example, blood sample is analyzed for estimation of the protein encoded by a serum marker. On the other hand, a suitable method can be selected for the determination of the activity of a protein encoded by the WDRPUH, KRZFPUH, PPIL1, or APCDD1 gene according to the activity of each protein to be analyzed.

Expression levels of the WDRPUH, KRZFPUH, PPIL1, or APCDD1 gene in a specimen (test sample) are estimated and compared with those in a normal sample. When such a comparison shows that the expression level of the target gene is higher than those in the normal sample, the subject is judged to be affected with a cell proliferative disease. The expression level of the WDRPUH, KRZFPUH, PPIL1, or APCDD1 gene in the specimens from the normal sample and subject may be determined at the same time. Alternatively, normal ranges of the expression levels can be determined by a statistical method based on the results obtained by analyzing the expression level of the gene in specimens previously collected from a control group. A result obtained by comparing the sample of a subject with the normal range; when the result does not fall within the normal range, the subject is judged to be affected with the cell proliferative disease. In the present invention, the cell proliferative disease to be diagnosed is preferably cancer. More preferably, when the expression level of the WDRPUH or KRZFPUH gene is estimated and compared with those in a normal sample, the cell proliferative disease to be diagnosed is hepatocellular carcinoma; and when the PPIL1 or APCDD1 gene is estimated for its expression level, then the disease to be diagnosed is colorectal cancer. Further, when the expression level of the KRZFPUH gene is estimated and compared with those in a normal sample, the cell proliferative disease to be diagnosed may be gastric or lung cancer, in addition to hepatocellular carcinoma.

In the present invention, a diagnostic agent for diagnosing cell proliferative disease, such as cancer including hepatocellular carcinoma and colorectal cancer, is also provided. The diagnostic agent of the present invention comprises a compound that binds to a polynucleotide or a polypeptide of the present invention. Preferably, an oligonucleotide that hybridizes to the polynucleotide of the present invention, or an antibody that binds to the polypeptide of the present invention may be used as such a compound.

Moreover, the present invention provides a method of screening for a compound for treating a cell proliferative disease using a polypeptide of the present invention. An embodiment of this screening method comprises the steps of: (a) contacting a test compound with a polypeptide of the present invention, (b) detecting the binding activity between the polypeptide of the present invention and the test compound, and (c) selecting a compound that binds to the polypeptide of the present invention.

The polypeptide of the present invention to be used for screening may be a recombinant polypeptide or a protein derived from the nature, or a partial peptide thereof. Any test compound, for example, cell extracts, cell culture supernatant, products of fermenting microorganism, extracts from marine organism, plant extracts, purified or crude proteins, peptides, non-peptide compounds, synthetic micromolecular compounds, and natural compounds, can be used. The polypeptide of the present invention to be contacted with a test compound can be, for example, a purified polypeptide, a soluble protein, a form bound to a carrier, or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-1α promoter (Kim et al., Gene 91: 217-223 (1990)), the CAG promoter (Niwa et al., Gene 108: 193-200 (1991)), the RSV LTR promoter (Cullen, Methods in Enzymology 152: 684-704 (1987)), the SRα promoter (Takebe et al., Mol Cell Biol 8: 466 (1988)), the CMV immediate early promoter (Seed and Aruffo, Proc Natl Acad Sci USA 84: 3365-3369 (1987)), the SV40 late promoter (Gheysen and Fiers, J Mol Appl Genet 1: 385-394 (1982)), the Adenovirus late promoter (Kaufman et al., Mol Cell Biol 9: 946 (1989)), the HSV TK promoter, and so on. The introduction of the gene into animal cells to express a foreign gene can be performed according to any methods, for example, the electroporation method (Chu et al., Nucleic Acids Res 15: 1311-1326 (1987)), the calcium phosphate method (Chen and Okayama, Mol Cell Biol 7: 2745-2752 (1987)), the DEAE dextran method (Lopata et al., Nucleic Acids Res 12:5707-5717 (1984); Sussman and Milman, Mol Cell Biol 4: 642-1643 (1985)), the Lipofectin method (Derijard, B Cell 7: 1025-1037 (1994); Lamb et al., Nature Genetics 5:22-30 (1993): Rabindran et al., Science 259: 230-234 (1993)), and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP), and so on by the use of its multiple cloning sites are commercially available.

A fusion protein prepared by introducing only small epitopes consisting of several to a dozen amino acids so as not to change the property of the polypeptide of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the polypeptide of the present invention (Experimental Medicine 13:85-90 (1995)).

In immunoprecipitation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-552, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, tissues such as testis for screening proteins binding to WDRPUH; testis, and placenta for screening proteins binding to KRZFPUH; heart, skeletal muscle, testis, thyroid, and adrenal gland for screening those binding to PPIL1; and heart, pancreas, prostate, ovary, lung, liver, kidney, spleen, thymus, colon, and peripheral leukocyte for those binding to APCDD1), or cultured cells expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-292 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene, and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized polypeptide of the present invention is exposed to synthetic chemical compounds, or natural substance banks, or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

A compound isolated by the screening is a candidate for drugs which promote or inhibit the activity of the polypeptide of the present invention, for treating or preventing diseases attributed to, for example, cell proliferative diseases, such as cancer. A compound in which a part of the structure of the compound obtained by the present screening method having the activity of binding to the polypeptide of the present invention is converted by addition, deletion and/or replacement, is included in the compounds obtained by the screening method of the present invention.

In a further embodiment, the present invention provides methods for screening candidate agents which are potential targets in the treatment of cell proliferative disease. As discussed in detail above, by controlling the expression levels of the WDRPUH, KRZFPUH, PPIL1, or APCDD1, one can control the onset and progression of cancer. Thus, candidate agents, which are potential targets in the treatment of cell proliferative disease, can be identified through screenings that use the expression levels and activities of WDRPUH, KRZFPUH, PPIL1, or APCDD1 as indices. In the context of the present invention, such screening may comprise, for example, the following steps:

a) contacting a candidate compound with a cell expressing the WDRPUH, KRZFPUH, PPIL1, or APCDD1; and b) selecting a compound that reduces the expression level of WDRPUH, KRZFPUH, PPIL1, or APCDD1 in comparison with the expression level detected in the absence of the test compound.

Cells expressing at least one of the WDRPUH, KRZFPUH, PPIL1, or APCDD1 include, for example, cell lines established from HCC or colorectal carcinomas; such cells can be used for the above screening of the present invention. The expression level can be estimated by a methods well known by one skilled in the art. In the method of screening, a compound that reduces the expression level of at least one of WDRPUH, KRZFPUH, PPIL1, or APCDD1 can be selected as candidate agents.

In another embodiment of the method for screening a compound for treating a cell proliferative disease of the present invention, the method utilizes the biological activity of the polypeptide of the present invention as an index. Since the WDRPUH, KRZFPUH, PPIL1, and APCDD1 proteins of the present invention have the activity of promoting cell proliferation, a compound which promotes or inhibits this activity of one of these proteins of the present invention can be screened using this activity as an index. This screening method includes the steps of: (a) contacting a test compound with the polypeptide of the present invention; (b) detecting the biological activity of the polypeptide of step (a); and (c) selecting a compound that suppresses the biological activity of the polypeptide in comparison with the biological activity detected in the absence of the test compound.

Any polypeptides can be used for screening so long as they comprise the biological activity of the WDRPUH, KRZFPUH, PPIL1, or APCDD1 protein. Such biological activity include cell-proliferating activity of the human WDRPUH, KRZFPUH, PPIL1, or APCDD 1 protein, the activity of PPIL1 to bind to SNW1 or stathmin. For example, a human WDRPUH, KRZFPUH, PPIL1, or APCDD1 protein can be used and polypeptides functionally equivalent to these proteins can also be used. Such polypeptides may be expressed endogenously or exogenously by cells.

Any test compounds, for example, cell extracts, cell culture supernatant, products of fermenting microorganism, extracts of marine organism, plant extracts, purified or crude proteins, peptides, non-peptide compounds, synthetic micromolecular compounds, or natural compounds, can be used.

The compound isolated by this screening is a candidate for agonists or antagonists of the polypeptide of the present invention. The term "agonist" refers to molecules that activate the function of the polypeptide of the present invention by binding to the polypeptide. Likewise, the term "antagonist" refers to molecules that inhibit the function of the polypeptide of the present invention by binding to the polypeptide. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

The compound isolated by the above screenings is a candidate for drugs which inhibit the activity of the polypeptide of the present invention and can be applied to the treatment of diseases associated with the polypeptide of the present invention, for example, cell proliferative diseases including cancer.

More particularly, when the biological activity of WDRPUH or KRZFPUH protein is used as the index, compounds screened by the present method serve as a candidate for drugs for the treatment of hepatocellular carcinoma. Furthermore, when the biological activity of KRZFPUH protein is used as the index, apart from HCC, compounds screened by the present method serve as a candidate for drugs for the treatment of gastric or lung carcinoma. On the other hand, when the biological activity of PPIL1 or APCDD1 protein is used as the index, compounds screened by the present method serve as a candidate for drugs for the treatment of colorectal carcinoma.

Moreover, compound in which a part of the structure of the compound inhibiting the activity of WDRPUH, KRZFPUH, PPIL1, or APCDD1 proteins is converted by addition, deletion and/or replacement are also included in the compounds obtainable by the screening method of the present invention.

Alternatively, the screening method of the present invention may comprise the following steps:
 a) contacting a candidate compound with a cell into which a vector comprising the transcriptional regulatory region of one or more marker genes and a reporter gene that is expressed under the control of the transcriptional regulatory region has been introduced, wherein the one or more marker genes are selected from the group consisting of WDRPUH, KRZFPUH, PPIL1, and APCDD1,
 b) measuring the activity of said reporter gene; and
 c) selecting a compound that reduces the expression level of said reporter gene as compared to a control.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

Further, in another embodiment of the method for screening a compound for treating a cell proliferative disease of the present invention, the method utilizes the promoter region of APCDD1. According to the present invention, the β-catenin/Tcf4 complex was discovered to bind to the two Tcf/LEF binding motifs in the transcriptional regulatory region of the APCDD1 gene and to be involved in the transcriptional activation of APCDD1. Therefore, compounds that inhibit the activation of the transcription of APCDD1 serve as candidates for drugs which inhibit the activity of the APCDD1 polypeptide of the present invention and can be applied to the treatment of diseases associated with the polypeptide, for example, cell proliferative diseases, such as cancer, especially colorectal cancer.

This screening method includes the steps of: (a) constructing a vector comprising the two Tcf/LEF binding motifs of APCDD1 upstream of a reporter gene; (b) transforming a cell with the vector of step (a); (c) contacting a test compound and the β-catenin/Tcf-4 complex with the cell of step (b); (d) detecting the expression of the reporter gene; and (e) selecting a compound that suppresses the expression of the reporter gene in comparison to that in the absence of the test compound.

Any test compound, for example, cell extracts, cell culture supernatant, products of fermenting microorganism, extracts from marine organism, plant extracts, purified or crude proteins, peptides, non-peptide compounds, synthetic micromolecular compounds, and natural compounds, can be used.

The screening can be conducted, for example, according to the method described in Example 28. For example, the vector comprising the two Tcf/LEF binding motifs of APCDD1 upstream of a reporter gene can be constructed by inserting the promoter region of APCDD1 into an expression vector comprising the reporter gene. The promoter region of APCDD1 may be obtained from genomic libraries using the 5' region of the human APCDD1 gene (SEQ ID NO: 7) as the probe. β-catenin and Tcf-4 can be prepared as in Example 28.

Any reporter gene may be used in the screening so long as its expression can be detected. Examples of reporter genes include β-gal gene, the CAT gene, and the luciferase gene. Detection of the expression of the reporter gene can be conducted corresponding to the type of the reporter gene. Although there are no particular restrictions on the cells into which the vector is introduced, preferable examples include HeLa cells.

The compound isolated by the screening is a candidate for drugs which inhibit the expression of the APCDD1 protein of the present invention and can be applied to the treatment of diseases associated with the APCDD1 protein, for example, cell proliferative diseases such as cancer, more particularly colorectal carcinoma. Moreover, compounds in which a part of the structure of the compound inhibiting the transcriptional activation of the APCDD1 protein by the β-catenin/Tcf-4 complex is converted by addition, deletion, substitution and/or insertion are also included in the compounds obtainable by the screening method of the present invention.

In a further embodiment of the method for screening a compound for treating a cell proliferative disease of the present invention, the method utilizes the binding ability of PPIL1 to SNW1 (SKI interacting protein) or stathmin. The PPIL1 protein of the present invention was revealed to associate with SNW1, a protein involved in the transcriptional activity of vitamin D receptor, and stathmin, a cytosolic phosphorprotein involved in the progression of the cell cycle. These findings suggest that the PPIL1 protein of the present invention exerts the function of cell proliferation via its binding to molecules, such as SNW1 and stathmin. Thus, it is expected that the inhibition of the binding between the PPIL1 protein and SNW1 or stathmin leads to the suppression of cell proliferation, and compounds inhibiting the binding serve as pharmaceuticals for treating cell proliferative disease such as cancer. Preferably, the cell proliferative disease treated by the compound screened by the present method is colorectal cancer.

This screening method includes the steps of: (a) contacting a polypeptide of the present invention with stathmin or SNW1 in the presence of a test compound; (b) detecting the binding between the polypeptide and stathmin or SNW1; and (c) selecting the compound that inhibits the binding between the polypeptide and stathmin or SNW1.

The PPIL1 polypeptide of the present invention, and SNW1 or stathmin to be used for the screening may be a recombinant polypeptide or a protein derived from the nature, or may also be a partial peptide thereof so long as it retains the binding ability to each other. The PPIL1 polypeptide, SNW1 or stathmin to be used in the screening can be, for example, a purified polypeptide, a soluble protein, a form bound to a carrier, or a fusion protein fused with other polypeptides.

Any test compound, for example, cell extracts, cell culture supernatant, products of fermenting microorganism, extracts from marine organism, plant extracts, purified or crude proteins, peptides, non-peptide compounds, synthetic micromolecular compounds, and natural compounds, can be used.

As a method of screening for compounds that inhibit the binding between the PPIL1 protein and SNW1 or stathmin, many methods well known by one skilled in the art can be used. Such a screening can be carried out as an in vitro assay system, for example, in a cellular system. More specifically, first, either the PPIL1 polypeptide, or SNW1 or stathmin is bound to a support, and the other protein is added together with a test sample thereto. Next, the mixture is incubated, washed, and the other protein bound to the support is detected and/or measured.

Examples of supports that may be used for binding proteins include insoluble polysaccharides, such as agarose, cellulose, and dextran; and synthetic resins, such as polyacrylamide, polystyrene, and silicon; preferably commercial available beads, and plates (e.g., multi-well plates, biosensor chip, etc.) prepared from the above materials may be used. When using beads, they may be filled into a column.

The binding of a protein to a support may be conducted according to routine methods, such as chemical bonding, and physical adsorption. Alternatively, a protein may be bound to a support via antibodies specifically recognizing the protein. Moreover, binding of a protein to a support can be also conducted by means of avidin and biotin binding.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia). Therefore, it is possible to evaluate the binding between the PPIL1 polypeptide and SNW1 or stathmin using a biosensor such as BIAcore.

Alternatively, either the PPIL1 polypeptide, or SNW1 or stathmin, may be labeled, and the label of the bound protein may be used to detect or measure the bound protein. Specifically, after pre-labeling one of the proteins, the labeled protein is contacted with the other protein in the presence of a test compound, and then, bound proteins are detected or measured according to the label after washing.

Labeling substances such as radioisotope (e.g., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine), and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, the binding of the PPIL1 polypeptide and SNW1 or stathmin can be also detected or measured using antibodies to the PPIL1 polypeptide and SNW1 or stathmin. For example, after contacting the PPIL1 polypeptide immobilized on a support with a test compound and SNW1 or stathmin, the mixture is incubated and washed, and detection or measurement can be conducted using an antibody against SNW1 or stathmin. Alternatively, SNW1 or stathmin may be immobilized on a support, and an antibody against PPIL1 may be used as the antibody.

In case of using an antibody in the present screening, the antibody is preferably labeled with one of the labeling substances mentioned above, and detected or measured based on the labeling substance. Alternatively, the antibody against the PPIL1 polypeptide, SNW1, or stathmin, may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, the PPIL1 polypeptide of the invention is fused to the SRF-binding region or GAL4-binding region and expressed in yeast cells. The SNW1 or stathmin binding to the PPIL1 polypeptide of the invention is fused to the VP16 or GAL4 transcriptional activation region and also expressed in the yeast cells in the existence of a test compound. When the test compound does not inhibit the binding between the PPIL1 polypeptide and SNW1 or stathmin, the binding of the two activates a reporter gene, making positive clones detectable.

As a reporter gene, for example, Ade2 gene, lacZ gene, CAT gene, luciferase gene and such can be used besides HIS3 gene.

The compound isolated by the screening is a candidate for drugs which inhibit the activity of the PPIL1 protein of the present invention and can be applied to the treatment of diseases associated with the PPIL1 protein, for example, cell proliferative diseases such as cancer, more particularly colorectal carcinoma. Moreover, compounds in which a part of the structure of the compound inhibiting the binding between the PPIL1 protein and SNW1 or stathmin is converted by addition, deletion, substitution and/or insertion are also included in the compounds obtainable by the screening method of the present invention.

When administrating the compound isolated by the methods of the invention as a pharmaceutical for humans and other mammals, such as mice, rats, guinea-pigs, rabbits, chicken, cats, dogs, sheep, pigs, cattle, monkeys, baboons, chimpanzees, for treating a cell proliferative disease (e.g., cancer) the isolated compound can be directly administered or can be formulated into a dosage form using known pharmaceutical preparation methods. For example, according to the need, the drugs can be taken orally, as sugarcoated tablets, capsules, elixirs, and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum, and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil, and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular, or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Moreover, the present invention provides a method for treating or preventing a cell proliferative disease, such as cancer, using an antibody against the polypeptide of the present invention. According to the method, a pharmaceutically effective amount of an antibody against the polypeptide of the present invention is administered. Since the expression of the WDRPUH, KRZFPUH, PPIL1, and APCDD1 protein are up-regulated in cancer cells, and the suppression of the expression of these proteins leads to the decrease in cell proliferating activity, it is expected that cell proliferative diseases can be treated or prevented by binding the antibody and these proteins. Thus, an antibody against the polypeptide of the present invention are administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day. Alternatively, an antibody binding to cell surface marker specific for tumor cell can be used as a tool for drug delivery. For example, the antibody having a cytotoxic agent are administered at a dosage sufficient to injure the tumor cell.

The present invention also relates to a method of inducing anti-tumor immunity comprising a step of administering WDRPUH, KRZFPUH, PPIL1, or APCDD1 protein or an immunologically active fragment thereof, or nucleic acids encoding any one of the protein and the fragments thereof. The WDRPUH, KRZFPUH, PPIL1, or APCDD1 protein or the immunologically active fragments thereof are useful as vaccines against cell proliferative disease. In the present invention, vaccine against cell proliferative disease refers to a substance that has the effect of inducing anti-tumor immunity when it is inoculated upon animals. In general, anti-tumor immunity includes immune responses such as the following:
  induction of cytotoxic lymphocytes against tumors,
  induction of antibodies that recognize tumors, and
  induction of anti-tumor cytokine production.

Therefore, when inoculation of a certain protein into an animal induces any one of these immune responses, the protein is said to have an anti-tumor immunity inducing effect. The induction of the anti-tumor immunity by a protein can be detected by observing the response of the immune system in the host against the protein in vivo or in vitro.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to the stimulation by the antigen, and then proliferate (this is referred to as activation of T cells). Therefore, CTL induction by a certain peptide can be evaluated by presenting the peptide to T cell by APC, and detecting induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

For example, the method of evaluating the inducing action of CTL using dendritic cells (DCs) as APC is well known. DC is a representative APC having the strongest CTL inducing action. In this method, the test polypeptide is initially contacted with DC, and then this DC is contacted with T cells. Detection of T cells having cytotoxic effects against the cells of interest after contacting with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

APC is not limited to DC, and peripheral blood mononuclear cells (PBMCs) may be used. In this case, there are reports that the induction of CTL can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using the polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide has the ability to induce anti-tumor immunity.

Anti-tumor immunity is induced by administering the vaccine of this invention, and this enables treatment and prevention of HCC or colon cancer. Therapy against cancer, or effect of preventing the onset of cancer may be any one of the following steps, such as inhibitory activity against growth of cancerous cells, involution of cancer, and suppression of occurrence of cancer. Otherwise, it may be decrease of mortality of individuals having cancer, decrease of tumor markers in the blood, alleviation of detectable symptoms accompanying cancer, or such. Such effects are preferably statistically significant, for example, observation, at a significance level of 5% or less, of therapeutic effect against cancer, or preventive effect against cancer onset compared to a control to which the vaccine was not administered is preferred. For example, Student's t-test, the Mann-Whitney U-test, or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, salmonella toxin, alum, and such, but are not limited thereto. Furthermore, the vaccine of this invention may be combined appropriately with a pharmaceutically acceptable carrier. Examples of such carriers are sterilized water, physiological saline, phosphate buffer, culture fluid, and such. Furthermore, it may contain as necessary, stabilizers, suspensions, preservatives, surfactants, and such. The vaccine is administered systemically or locally. Vaccine administration may be by single administration, or boosted by multiple administrations.

When using APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and after inducing APC or CTL, the cells can be administered to the subject. APC can be also induced by introducing a vector encoding the polypeptide into PBMCs ex vivo. APC or CTL induced in vitro can be cloned prior to administration. By cloning and growing cells which have high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of the polypeptide of the present invention is provided. The pharmaceutical composition may be used for raising anti tumor immunity. The normal expression of WDRPUH and KRZFPUH are restricted to testis, and placenta and testis, respectively, and therefore, suppression of these genes may not adversely affect other organs. Thus, the WDRPUH and KRZFPUH polypeptides are preferable for treating cell proliferative disease, especially HCCs.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications, and publications cited herein are incorporated by reference.

BEST MODE FOR CARRYING OUT THE INVENTION

The present invention is illustrated in details by following Examples, but is not restricted to these Examples.

Example 1

Identification of Two Novel Genes, WDRPUH and KRZFDUH, Frequently Up-Regulated in HCCs The expression profile of 20 HCCs were compared with that of corresponding non-cancerous liver tissues using in-house genome-wide cDNA microarray containing 23040 genes. More specifically, HCC tissues, and corresponding non-cancerous tissues were obtained with informed consent from surgical specimens of patients who underwent surgery. Total RNA was extracted from microdissected tissue with Qiagen RNeasy kit (Qiagen) or Trizol reagent (Life Technologies) according to the manufacturers' protocol. The extracted total RNA was treated with DNase I, amplified with Ampliscribe T7 Transcription Kit (Epicentre Technologies) and labeled during reverse transcription using Cy-dye (Amersham). Cy5 and Cy3 were used for labeling RNAs from non-cancerous tissue and tumor, respectively. Then, hybridization, washing, and detection were carried out according to the method of Ono et al. (Cancer Res 60: 5007-11 (2000)). The fluorescent intensity of Cy5 and Cy3 at each target spot was measured using Array Vision software (Amersham Pharmacia). The measurement was conducted in duplicate, and after subtracting background signal from the detected fluorescent intensities at each target spot, the average was calculated. Then, all fluorescent intensities detected on slides were normalized to adjust the mean Cy5 and Cy3 intensity of 52 housekeeping genes for each slide. Genes with a fluorescent intensity below 25000 units for both Cy3 and Cy5 were excluded from further investigation, and genes with >2.0 Cy3/Cy5 signal ratios were selected for further evaluation.

Among the commonly up-regulated genes in HCCs, a gene with in-house accession number D3197, corresponding to an EST (Hs. 122614) of UniGene cluster (see the world wide web at ncbi.nlm.nih.gov/UniGene/), was over-expressed in eleven of twelve HCCs compared with the corresponding no-cancerous liver tissues (FIG. 1a). The gene comprised an open reading frame encoding a protein with WD40 repeats, and thus was dubbed WDRPUH (WD40 repeats protein up-regulated in HCCs). WDRPUH was also up-regulated in 1 of 2 cases of gastric cancer. Further, gene with the in-house accession number C6242 (EST Hs. 58461) was detected as a gene significantly up-regulated in eleven of fourteen HCCs compared with the corresponding non-cancerous liver tissues (FIG. 1b) and was dubbed KRZFPUH (Krupple-type zinc finger protein up-regulated in HCC) based on its coding protein containing a zinc finger motif KRZFPUH was also up-regulated in all the tested gastric cancer cases (two cases) and 2 of 36 lung cancer cases.

Subsequently, semi-quantitative RT-PCR was conducted to confirm the elevated expression of WDRPUH and KRZF-PUH in another ten HCC cases (FIGS. 1c and d). Specifically, total RNA was extracted with Qiagen RNeasy kit (Qiagen) or Trizol reagent (Life Technologies) according to the manufacturers' protocol. Ten-microgram aliquot of total RNA were reverse transcribed into cDNAs using poly $dT_{12-18}$ primer (Amersham Pharmacia Biotech) with Superscript II reverse transcriptase (Life Technologies). Obtained single-stranded cDNA preparation was diluted in 20 μl of PCR buffer (TaKaRa). Then PCR amplification by standard RT-PCR experiment was conducted using following primers:

```
WDRPUH forward primer:
5'-CAGGTGGAAATGACCATCTGGTCAAAG-3'    [SEQ ID NO: 9]
and reverse primer:
5'-CATCAGCTTCAGGAGGTATATGGTAC-3';    [SEQ ID NO: 10]
and KRZFPUH forward primer:
5'-GTGGCACTGTGGTGTTACCTTAT-3'        [SEQ ID NO: 11]
and reverse primer:
5'-CCTCTAAACCTTTGCCTACGACT-3'.       [SEQ ID NO: 12]
```

The amplification was conducted using GeneAmp PCR system 9700 (Perkin-Elmer) under following condition: denaturing at 94° C. for 4 min; 35 cycles of 94° C. for 30 s, 56° C. for 30 s, and 72° C. for 45 s.

Example 2

Expression, Isolation, and Characterization of the Novel Human Gene WDRPUH

Figure 2:
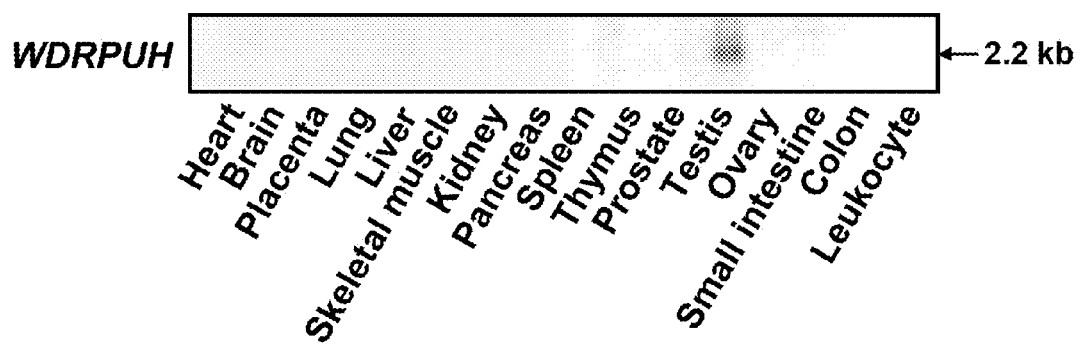
FIGS. 2a and 2b depict the expression of WDRPUH in various human tissues and the predicted protein structure and protein motifs of WDRPUH.
Figure 2:
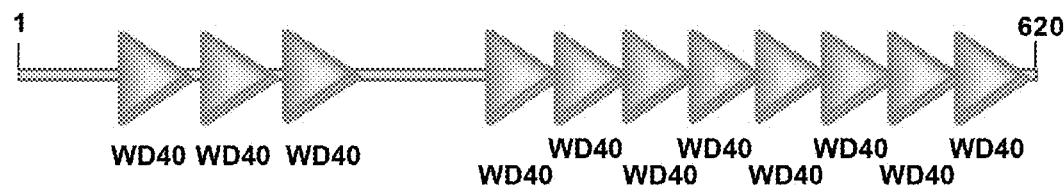

Next, multi-tissue northern blot analysis was performed using the PCR product of WDRPUH as a probe. More specifically, human multiple-tissue blots (Clontech) were hybridized with $^{32}$P-labeled PCR product of WDRPUH. Pre-hybridization, hybridization, and washing were performed according to the supplier's recommendations. The blots were autoradiographed with intensifying screens as −80° C. for 24 to 72 h. As a result, a 2-kb transcript was detected to be abundantly expressed in testis (FIG. 2a). Since D3197 was smaller than the WDRPUH cDNA detected on the Northern blot, next the inventors investigated the 5' sequence of WDRPUH cDNA. First, the genomic sequence corresponding to D3197 was searched in genomic databases (see the world wide web at ncbi.nlm.nih.gov/BLAST/) using BLAST program to find a cosmid sequence (GenBank Accession No. AC026855) assigned to chromosomal band 17p13. Candidate-exon sequences of the genomic sequence were predicted using GENSCAN, Gene Recognition, and Assembly Internet Link program, and the predicted exon sequences were connected. Then, 5' rapid amplification of cDNA ends (5'-RACE) was carried as follows: 5' RACE was carried out using Marathon cDNA amplification kit (Clontech) according to the manufacturer's instruction. The 5' part of WDRPUH was prepared using gene-specific reverse primers 5'-TTAC-CGTCGTTCCATGCTGAAATGATGC-3' [SEQ ID NO:13] and AP-1 primer supplied with the kit. cDNA template was synthesized from human testis mRNA (Clontech), and the amplified product was cloned using TA cloning kit (Invitrogen) to determine its sequence with ABI PRISM 3700 DNA sequencer (Applied Biosystems). The determined assembled sequence consisted of 2152 nucleotides containing an open reading frame of 1860 nucleotides encoding a protein of 620 amino acid residues (GenBank Accession No. AB065281). A search for protein motifs with Simple Modular Architecture Research Tool (SMART, see smart.embl-heidelberg.de) revealed 11 WD40 repeats domains for the predicted protein (FIG. 2b). The determined nucleotide sequence of WDRPUH and its predicted amino acid sequence are shown in SEQ ID NOs:1 and 2, respectively.

Example 3

Subcellular Localization of WDRPUH

Figure 3:
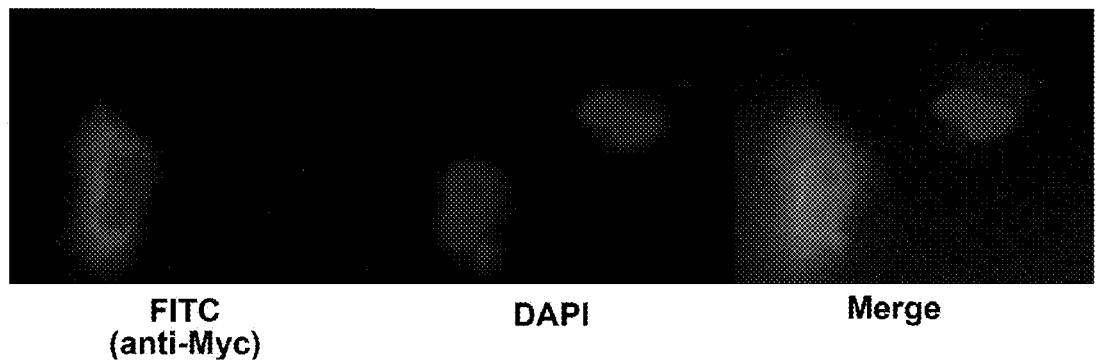
FIG. 3 is a photograph depicting the sub-cellular localization of WDRPUH observed by immunocytochemistry on SNU475 cells transfected with pcDNA3.1myc/His-WDRPUH, particularly using anti-myc monoclonal antibody and for visualization FITC conjugated secondary anti-mouse IgG antibody. Nuclei were counter-stained with DAPI.

The entire coding region corresponding to WDRPUH was amplified using gene specific primer set: 5'-GGGGTACCAC-CATGGATAACAAAATTTCGCCGGAG-3' [SEQ ID NO: 14] and 5'-CGGAATTCTCAGGAGGTATATGGGTACT-TCCATGC-3' [SEQ ID NO: 15]; and cloned into pcDNA3.1myc/His vector (Invitrogen). Then, the constructed vector pcDNA3.1myc/His-WDRPUH was transiently transfected into SNU475 cells (Korea cell-line bank) and the cells were grown in RPMI1640. The cells were fixed with PBS containing 4% paraformaldehyde for 15 min, then permeabilized with PBS containing 0.1% Triton X-100 for 2.5 min at room temperature (RT). Subsequently, cells were covered with 2% BSA in PBS for 24 h at 4° C. to block non-specific hybridization. 1:1000 diluted mouse anti-myc monoclonal antibody (Sigma) was used as the primary antibody for immunocytochemical staining, and the reaction was visualized after incubation with Rhodamine-conjugated anti-mouse secondary antibody (Leinco and ICN). Nuclei were counter-stained with 4',6'-diamidine-2'-phenylindole dihydrochloride (DAPI). Fluorescent images were obtained under an ECLIPSE E800 microscope. As a result, the tagged-WDRPUH protein was revealed to be present in the cytoplasm of the cells (FIG. 3).

Example 4

Effect of WDRPUH on Cell Growth

To investigate the effect of WDRPUH on cell growth, colony-formation assay by transfecting NIH3T3 cells (ATCC, Rockville, Md.) with a plasmid expressing WDRPUH (pcDNA-WDRPUH) was carried out. Specifically, the entire coding region corresponding to WDRPUH was amplified as in Example 3 and cloned into pcDNA3.1 (Invitrogen). The cells were transfected with the plasmid pcDNA-WDRPUH, control plasmids (mock), and plasmids expressing the complementary strand of WDRPUH (pcDNA-antisense), respectively. The transfected cells were incubated in Dulbecco's modified Eagle's medium (DMEM) with appropriate concentration of geneticin for 10 to 21 days. Then, the cells were fixed with 100% methanol and stained by Giemsa solution. All experiments were carried out in triplicate.

Figure 4:
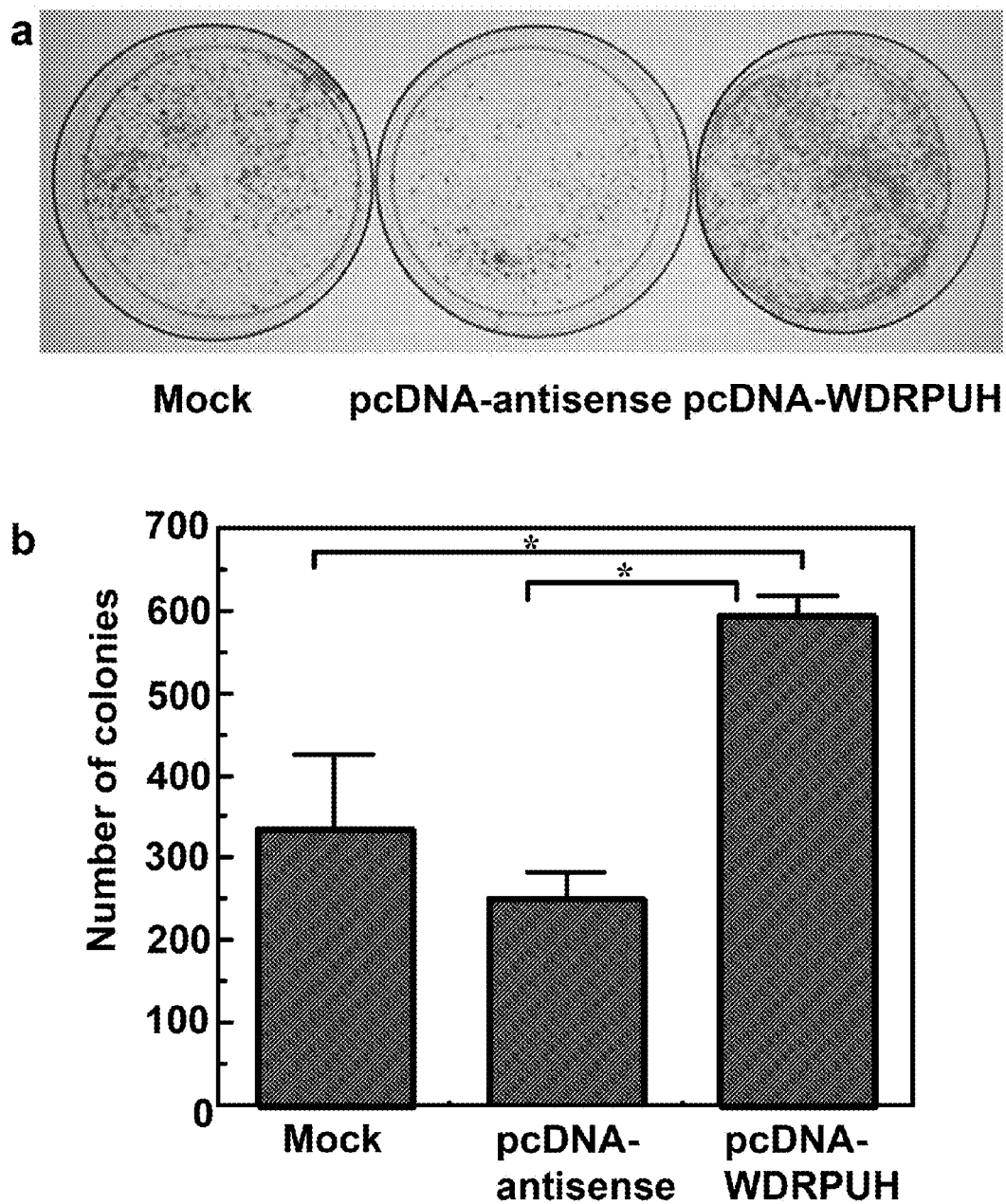
FIGS. 4a and 4b depict the effect of WDRPUH on the cell growth of NIH3T3 cells.

As a result, compared with the control plasmid (mock) or pcDNA-antisense, markedly more colonies were produced by cells transfected with pcDNA-WDRPUH (FIGS. 4a and b). Statistical analysis was conducted according to the Student's t test to determine the significant difference.

Example 5

Growth Suppression of Hepatoma Cells by Antisense S-Oligonucleotides Designated to Reduce Expression of WDRPUH To test whether the suppression of WDRPUH may result in growth retardation and/or cell death in HCC cells, various antisense S-oligonucleotides designated to suppress the expression of WDRPUH were synthesized. SNU475 cells (Korea cell-line bank) plated onto 10-cm dishes ($2 \times 10^5$ cells/dish) were transfected with antisense S-oligonucleotides encompassing the first exon-intron boundary of WDRPUH (WDRPUH-AS4; 5'-GGCCTCACCATTGAAG-3' [SEQ ID NO: 16]) or control S-oligonucleotides (WDRPUH-S4; 5'-CTTCAATGGTGAGGCC-3' [SEQ ID NO: 17]) using LIPOFECTIN Reagent (GIBCO BRL); and cultured in RPMI1640 supplemented with an appropriate concentration of geneticin for six to twelve days. The cells were analyzed for their expression of WDRPUH and GAPDH by RT-PCR and western blotting.

Figure 5:
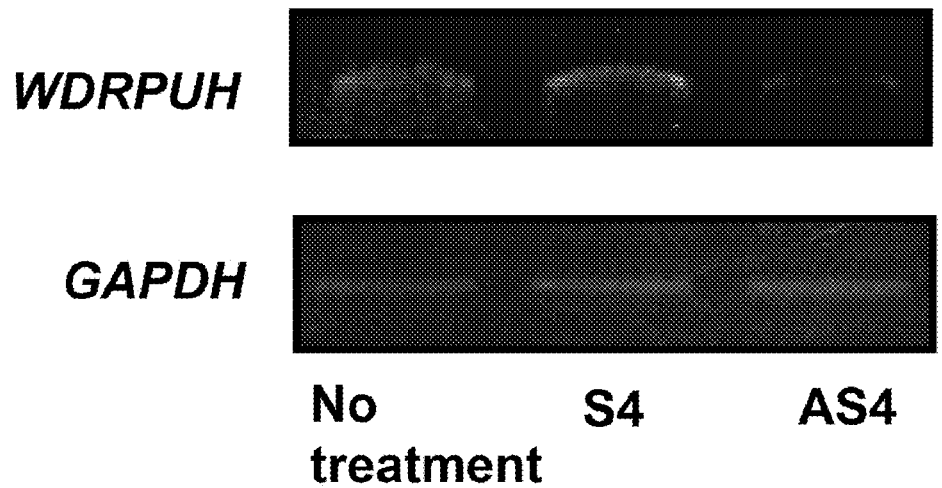
FIGS. 5a and 5b depict the growth suppressive effect of antisense S-oligonucleotides designated to suppress WDRPUH.
Figure 5:
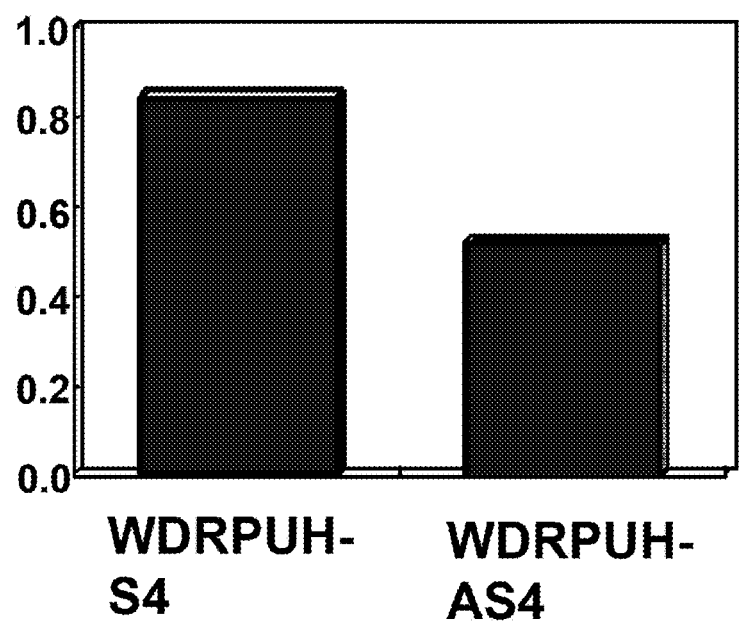

Endogenous expression of WDRPUH was significantly reduced by the transfection of WDRPUH-AS4 compared to control (WDRPUH-S4) in SNU475 cells (FIG. 5a).

Next, a 3-(4,5-dimethylthiazol-2-yl)-2,5-diphenyltetrazolium bromide (MTT) assay was performed by plating SNU475 cells at a density of $5 \times 10^5$ cells/100 mm dish. The cells were transfected in triplicate with sense or antisense S-oligonucleotides designated to suppress WDRPUH. After 72 h of culture, the medium was replaced with fresh medium containing 500 µg/ml of MTT (Sigma) and the plates were incubated for 4 h at 37° C. Then, the cells were lysed by the addition of 1 ml of 0.01 N HCl/10% SDS. The color reaction was quantified with an ELISA plate reader at a test wavelength of 570 nm (reference 630 nm). The cell viability was represented by the absorbance compared to the control.

Similarly to the above analysis by RT-PCR and western blotting, transfection of WDRPUH-AS4 significantly reduced the number of surviving cells compared with WDRPUH-S4 (FIG. 5b), suggesting that WDRPUH may play an important role in cell growth and/or survival of hepatocellular carcinoma cells. This result was confirmed by three independent experiments.

Example 6

Construction of Plasmids Expressing WDRPUH siRNAs and their Effect on Growth of HCC Cells In mammalian cells, short interfering RNA (siRNA) composed of 20 to 21-mer double stranded RNA (d5RNA) with 19 complementary nucleotides and 3' terminal complementary dimers of thymidine or uridine, have been recently shown to have a gene specific gene silencing effect without inducing global changes in gene expression. Therefore, the present inventors constructed plasmids expressing various WDRPUH-siRNAs and examined their effect on WDRPUH expression.

First, psiH1BX3.0 vector was constructed as follows. Since H1RNA gene was reported to be transcribed by RNA polymerase III, which produce short transcripts with uridines at the 3' end, the genomic fragment of H1RNA gene containing its promoter region was amplified by PCR using a set of primers: 5'-TGGTAGCCAAGTGCAGGTTATA-3' [SEQ ID NO: 18] and 5'-CCAAAGGGTTTCTGCAGTTTCA-3' [SEQ ID NO: 19]; and human placental DNA as a template. The product was purified and cloned into pCR2.0 plasmid vector using TA cloning kit (Invitrogen) according to the supplier's protocol. A fragment containing the H1RNA gene was amplified by PCR with a set of primers: 5'-TGCGGATCCAGAGCAGATTGTACTGAGAGT-3' [SEQ ID NO: 20] and 5'-CTCTATCTCGAGTGAGGCGGAAAGAACCA-3' [SEQ ID NO: 21]; digested with BamHI and XhoI, and was purified. Then, the purified BamHI-XhoI fragment containing the H1RNA gene was cloned into nucleotide 1257 to 56 fragment of pcDNA3.1(+) (Invitrogen). The ligated DNA was used as a template for PCR with primers:

5'-TTTAAGCTTGAAGACCATTTTTG-
GAAAAAAAAAAAAAAAAAAAAAAAC-3' [SEQ ID NO 22] and

5'-TTTAAGCTTGAAGACATGGGAAAGAGTG-
GTCTCA-3' [SEQ ID NO: 23]. The product was digested with HindIII, and subsequently self-ligated to produce psiH1BX3.0 vector plasmid.

Control plasmid and plasmids expressing WDRPUH-siRNAs were prepared by cloning double-stranded oligonucleotides into the BbsI site of psiH1BX3.0 vector. The oligonucleotides cloned into the vector was as follows:

psiH1BX-WDRPUH01,
[SEQ ID NO: 24]
5'-CACC<u>AATGTGATCTTCTCCAGGTGCTT</u>CAAGAGAGCACCTGGAG AAGATCACATT-3'
and
[SEQ ID NO: 25]
5'-AAAA<u>AATGTGATCTTCTCCAGGTGC</u>TCTCTTGAAGCACCTGGAG

AAGATCACATT-3';

psiH1BX-WDRPUH02,
[SEQ ID NO: 26]
5'-CACC<u>AAGGACACCAGTTTCTCGTAGT</u>TCAAGAGACTACGAGAAA CTGGTGTCCTT-3'
and
[SEQ ID NO: 27]
5'-AAAA<u>AAGGACACCAGTTTCTCGTAGT</u>CTCTTGAACTACGAGAAA

CTGGTGTCCTT-3';

psiH1BX-WDRPUH03,
[SEQ ID NO: 28]
5'-CACC<u>AAAGAGACGCTCATAGCGACT</u>TTCAAGAGAAGTCGCTATG AGCGTCTCTTT-3'
and
[SEQ ID NO: 29]
5'-AAAA<u>AAAGAGACGCTCATAGCGACT</u>TCTCTTGAAAGTCGCTATG

AGCGTCTCTTT-3';

psiH1BX-WDRPUH05,

-continued

[SEQ ID NO: 30]
5'-CACCAACGACGGTAAAATCCGAGCCTTCAAGAGAGGCTCGGATT

TTACCGTCGTT-3' and

[SEQ ID NO: 31]
5'-AAAAAACGACGGTAAAATCCGAGCCTCTCTTGAAGGCTCGGATT

TTACCGTCGTT-3';

and control psiH1BX-EGFP (mock),

[SEQ ID NO: 32]
5'-CACCGAAGCAGCACGACTTCTTCTTCAAGAGAGAAGAAGTCGTG

CTGCTTC-3'
and

[SEQ ID NO: 33]
5'-AAAAGAAGCAGCACGACTTCTTCTCTCTTGAAGAAGAAGTCGTG

CTGCTTC-3'.

The target sequence of siRNA in each of the sequences is underlined. The plasmids were transfected into HepG2 cells using FuGENE6 reagent (Roche) according to the supplier's recommendations. Total RNA was extracted from the cells 48 h after the transfection.

Figure 6:
FIGS. 6A and 6B depict the growth suppressive effect of WDRPUH-siRNAs.
Figure 6:
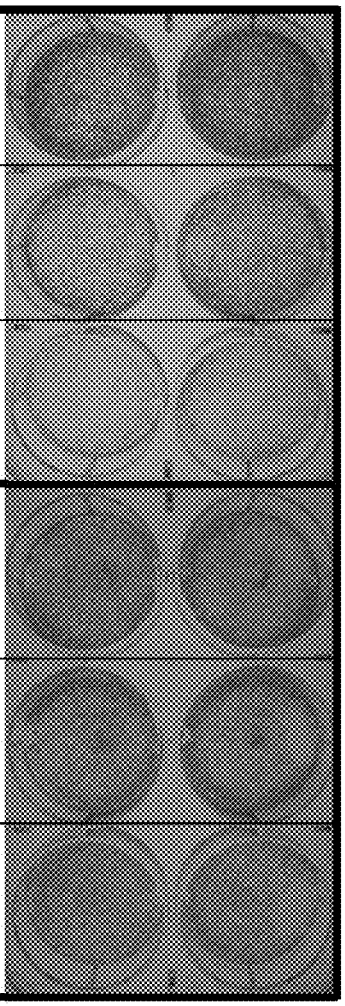

As a result, among them, psiH1BX-WDRPUH01 but not psiH1BX-WDRPUH02, psiH1BX-WDRPUH03 or psiH1BX-WDRPUH05 significantly suppressed expression of WDRPUH in the cells (FIG. 6A). To test whether the suppression of WDRPUH may result in growth suppression of hepatoma cells, HepG2 cells were transfected with psiH1BX-WDRPUH01, psiH1BX-WDRPUH02, psiH1BX-WDRPUH03, or psiH1BX-WDRPUH05, psiH1BX-EGFP or mock vector. Viable cells transfected with psiH1BX-WDRPUH01 were markedly reduced compared to those transfected with psiH1BX-WDRPUH02, psiH1BX-WDRPUH03, or psiH1BX-WDRPUH05, psiH1BX-EGFP or the control, suggesting that decreased expression of WDRPUH suppresses the growth of hepatoma cells (FIG. 6B).

Example 7

Preparation of Anti-WDRPUH Antibody

To examine the expression and explore the function of WDRPUH, polyclonal antibody against WDRPUH was prepared as follows. First, recombinant His-tagged WDRPUH was produced in *E. coli* and purified from the cells using Pro Bond™ histidine Resin (Invitrogen) according to the manufacturer's recommendations. The recombinant protein was used for the immunization of rabbits. The polyclonal antibody against WDRPUH was purified from the sera.

Figure 7:
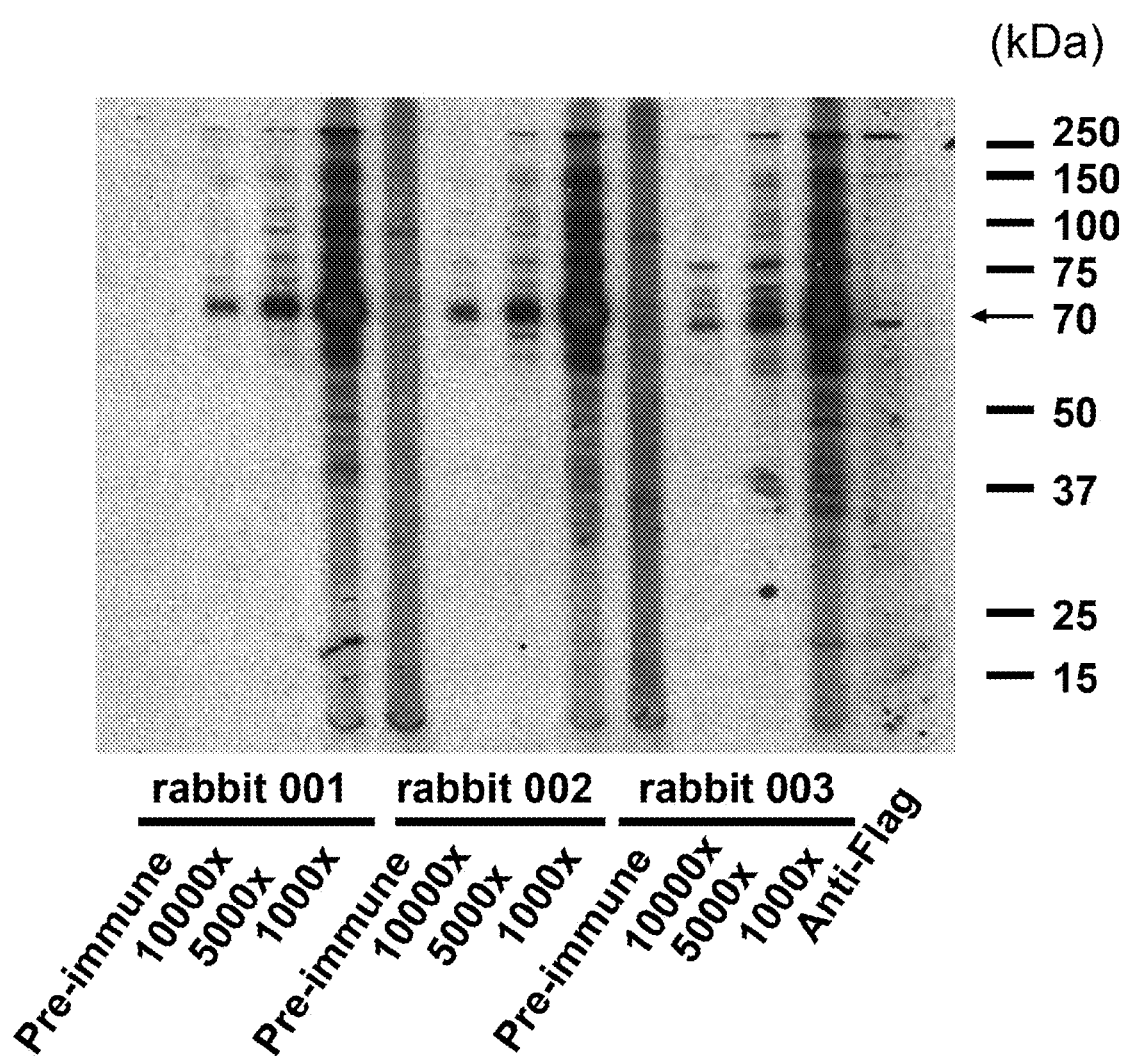
FIG. 7 is a photograph depicting the result of a Slot blot analysis of FLAG-tagged WDRPUH protein using anti-WDRPUH anti-sera (#1, #2, and #3), pre-immune sera, and anti-FLAG antibody.

The immunoblotting with the anti-WDRPUH sera but not pre-immune sera showed a 70 kD band of FLAG-tagged WDRPUH, which was identical by size to that detected using anti-FLAG antibody (FIG. 7).

Example 8

Expression, Isolation, and Characterization of Novel Human Gene, KRZFPUH

Figure 8:
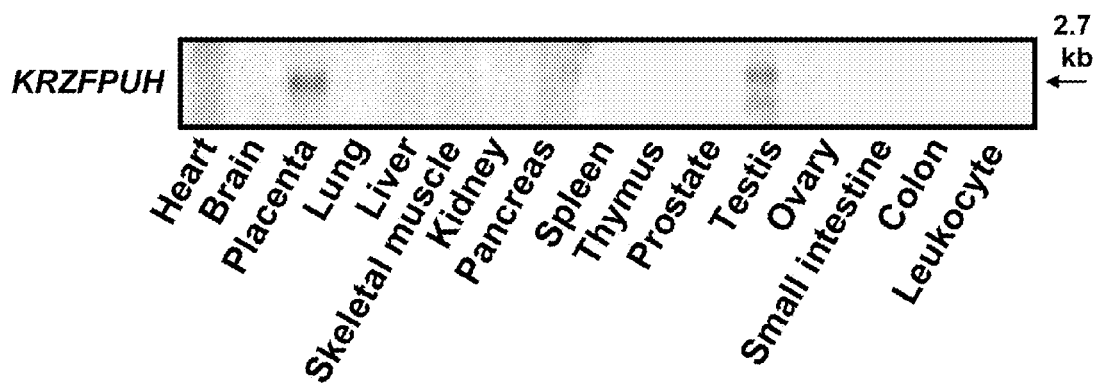
FIGS. 8a and 8b depict the expression of KRZFPUH in various human tissues and the predicted protein structure and protein motifs of KRZFPUH.
Figure 8:
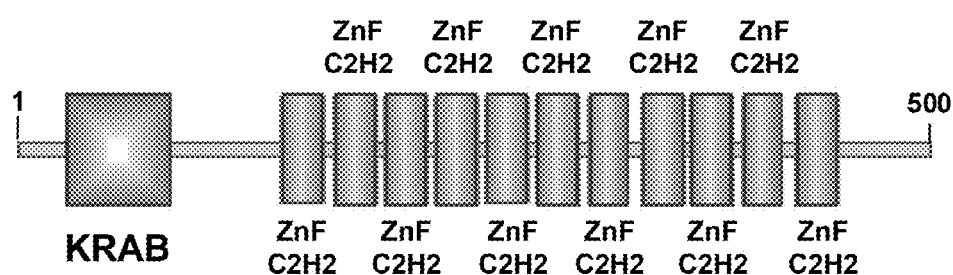

Multi-tissue northern blot analysis was conducted as in Example 2 using C6242 cDNA as a probe. The result showed that a 2.8-kb transcript was abundantly expressed in placenta and testis (FIG. 8a). Since C6242 was smaller than that detected on Northern blot, the sequence of the 5' part of KRZFPUH cDNA was investigated. First, the genomic sequences corresponding to C6242 was searched using BLAST program in genomic databases (see the world wide web at ncbi.nlm.nih.gov/BLAST/) to find a working draft sequence (GenBank accession number:NT-024802) that had been assigned to chromosomal band 16p11. Using GEN-SCAN, Gene Recognition, and Assembly Internet Link program with the genomic sequences, candidate-exon sequences were predicted, and the predicted exon sequences were connected. Then, 5'RACE was carried out as in Example 2 except 5'-TAGATTCTGGGCGCACTTGTGGCTCTCC-3' [SEQ ID NO: 34] was used as the primer to consequently obtain an assembled sequence of 2744 nucleotides containing an open reading frame of 1500 nucleotides encoding a 500-amino-acid protein (GenBank Accession No. AB065282). A search for protein motifs with Simple Modular Architecture Research Tool (SMART, see smart.embl-heidelberg.de) revealed that the predicted protein contained a Kruppel-type zinc finger domain (FIG. 8b). The determined nucleotide sequence of KRZFPUH and its predicted amino acid sequence are shown in SEQ ID NOs: 3 and 4, respectively.

Example 9

Subcellular Localization of KRZFPUH

Figure 9:
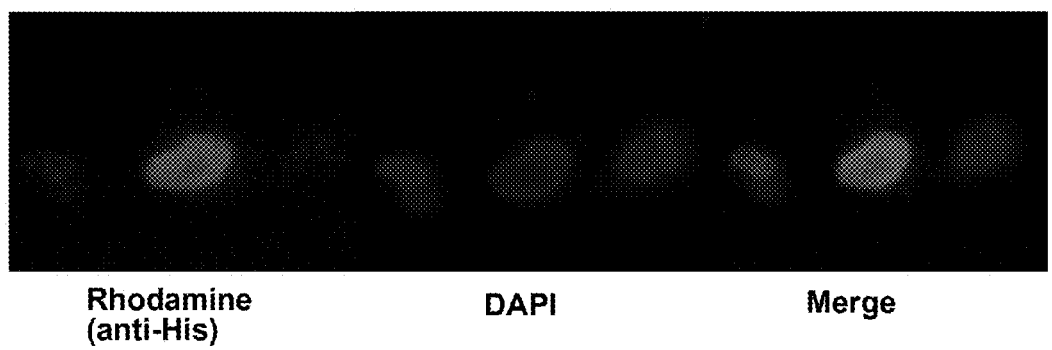
FIG. 9 is a photograph depicting the sub-cellular localization of KRZFPUH observed by immunocytochemistry on SNU475 cells transfected with pcDNA3.1myc/His-KRZFPUH, particularly using anti-His monoclonal antibody and for visualization Rhodamine conjugated secondary anti-mouse IgG antibody. Nuclei were counter-stained with DAPI.

The entire coding region corresponding to KRZFPUH was amplified using gene specific primer set: 5'-GGGGTACCAC-CATGGCGCCACCTTCG-3' [SEQ ID NO: 35] and 5'-CG-GAATTCATGGGCGTTGCCCCTCTGACTGG-3' [SEQ ID NO: 36]; and cloned into a pcDNA3.1myc/His vector (Invitrogen). Then this construct was transiently transfected into SNU475 cells (Korea cell-line bank) and subcellular localization of KRZFPUH was studied as in Example 3. The immunocytochemical staining of the cells revealed that the tagged-KRZFPUH protein was present in the nucleus (FIG. 9).

Example 10

Effect of KRZFPUH on Cell Growth

To analyze the effect of KRZFPUH on cell growth, colony-formation assay was conducted by transfecting COS7 cells (ATCC, Rockville, Md.) with a plasmid expressing KRZF-PUH (pcDNA-KRZFPUH). Specifically, the entire coding region corresponding to KRZFPUH was amplified as in Example 9 and cloned into pcDNA3.1 (Invitrogen). The cells were transfected with the plasmid pcDNA-KRZFPUH, control plasmids (mock), and plasmids expressing the complementary strand of KRZFPUH (pcDNA-antisense), respectively. The transfected cells were incubated in DMEM with appropriate concentration of geneticin for 10 to 21 days. Then, the cells were fixed with 100% methanol and stained by Giemsa solution. All experiments were carried out in triplicate.

Figure 10:
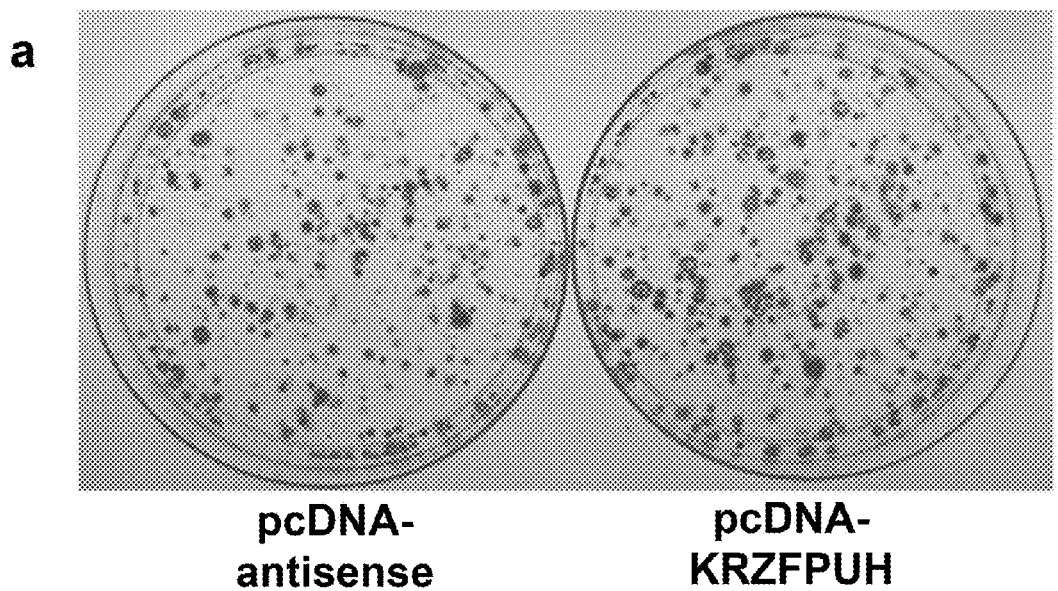
FIGS. 10a and 10b depict the effect of KRZFPUH on the cell growth of COS7 cells.
Figure 10:
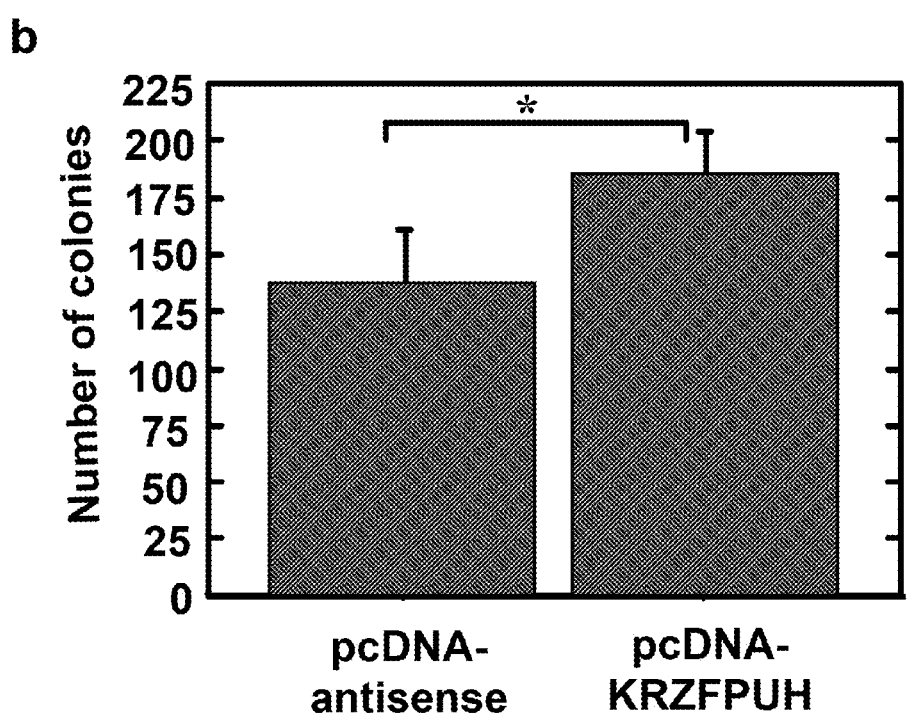

Compared with control plasmids expressing complementary strand of KRZFPUH (pcDNA-antisense), pcDNA-KRZFPUH produced markedly more colonies in COS7 cells as shown in FIGS. 10a and b. This result was confirmed by three independent experiments. Statistical analysis was conducted according to the Student's t test to determine the significant difference.

Example 11

Figure 11:
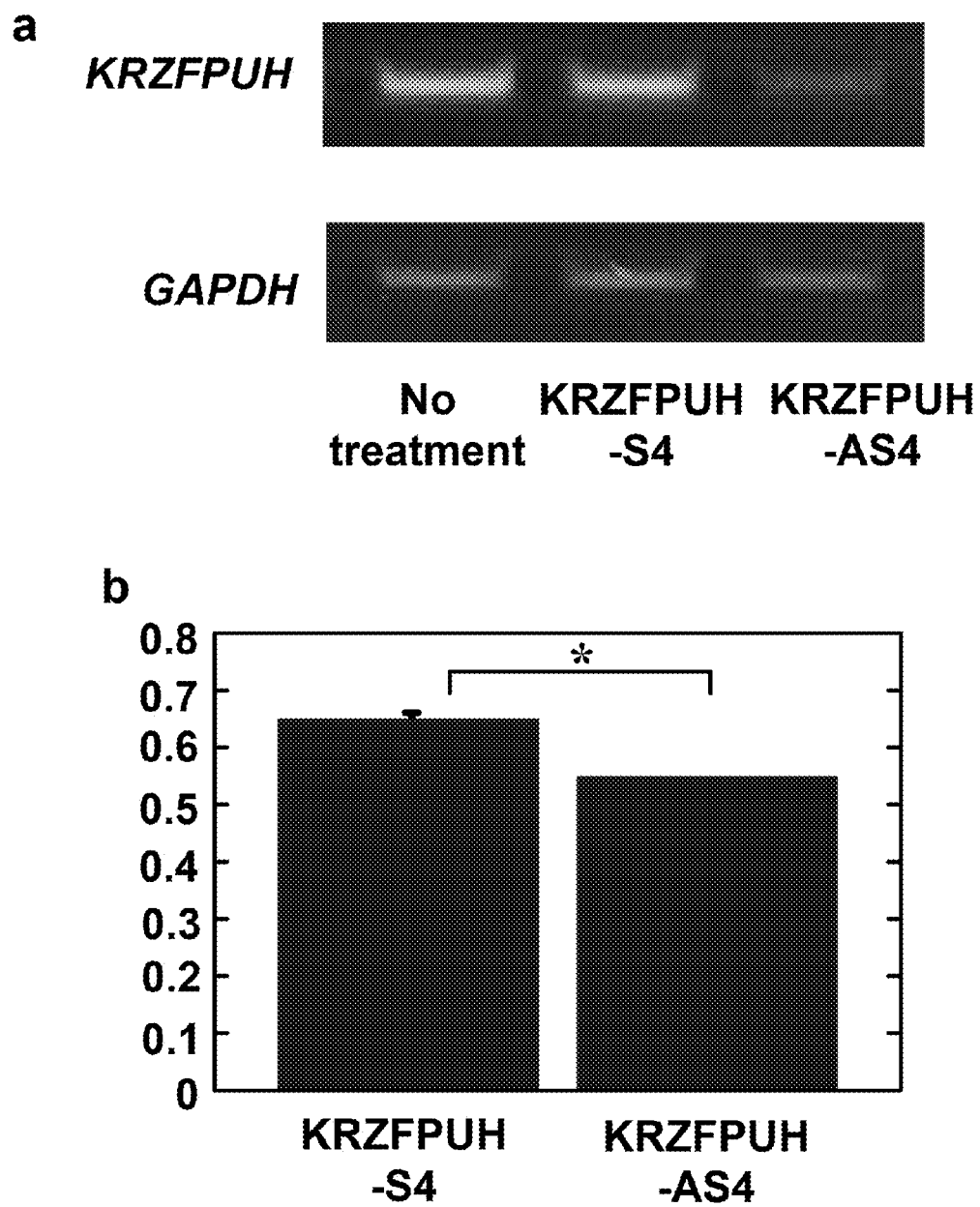
FIGS. 11a and 11b depict the growth suppressive effect of antisense S-oligonucleotides designated to suppress KRZFPUH.

Growth Suppression of Hepatoma Cells by Antisense S-Oligonucleotides Designated to Reduce Expression of KRZFPUH To test whether the suppression of the expression of KRZFPUH may result in growth retardation and/or cell death of HCC cells, various antisense S-oligonucleotides designated to suppress its expression were synthesized. Alexander cells (ATCC, Rockville, Md.) plated onto 10-cm dishes ($2\times10^5$ cells/dish) were transfected with antisense S-oligonucleotides encompassing the first exon-intron boundary of KRZFPUH (KRZFPUH-AS4; 5'-GGCCTCAC-CGAGCGCG-3' [SEQ ID NO: 37] or control S-oligonucleotides (KRZFPUH-S4; 5'-CGCGCTCGGTGAGGCC-3' [SEQ ID NO: 38]) using LIPOFECTIN Reagent (GIBCO BRL); and cultured in RPMI1640 supplemented with an appropriate concentration of geneticin for six to twelve days. The cells were then fixed with 100% methanol and stained with Giemsa solution. The endogenous expression of KRZFPUH and number of surviving cells were significantly reduced by the transfection of antisense S-oligonucleotides (KRZFPUH-AS4) compared with that of control sense S-oligonucleotides (KRZFPUH-S4) in Alexander cells that constitutively express abundant amount of KRZFPUH (FIGS. 11a and b), suggesting that KRZFPUH may play an important role for cell growth and/or survival of HCC cells. This result was confirmed by three independent experiments. Statistical analysis was conducted according to the Student's t test to determine the significant difference.

Example 12

Construction of Plasmids Expressing KRZFPUH siRNAs and their Effect on Growth of HCC Cells Plasmids expressing KRZFPUH-siRNAs were prepared by cloning double-stranded oligonucleotides into psiU6BX3.0 vector. The oligonucleotides used for KRZFPUH-siRNAs were:

```
                                      (SEQ ID NO: 104)
5'-CACCAACGAAACACCGATGACTGGGTTCAAGAGACCCAGTCATCGG

TGTTTCGTT-3'
and (SEQ ID NO: 105)
5'-AAAAAACGAAACACCGATGACTGGGTCTCTTGAACCCAGTCATCGG TGTTTCGTT-3' for psiU6BX-KRZFPUH1;

(SEQ ID NO: 106)
5'- CACCAATCACCGGACCACACACACATTCAAGAGATGTGTGTGTGG

TCCGGTGATT-3'
and (SEQ ID NO: 107)
5'-AAAAAATCACCGGACCACACACACATCTCTTGAATGTGTGTGTGGT CCGGTGATT-3' for psiU6BX-KRZFPUH2;

(SEQ ID NO: 108)
5'-CACCAAACCTTGCCTACGACATGTTTTCAAGAGAAACATGTCGTAG

GCAAGGTTT-3'
and
```

```
                                      (SEQ ID NO: 109)
5'-AAAAAAACCTTGCCTACGACATGTTTCTCTTGAAAAACATGTCGTAG

GCAAGGTTT-3' for psiU6BX-KRZFPUH3;

and (SEQ ID NO: 110)
5'-CACCAAAAGGTTTCCGTTAGCCCCGTTCAAGAGACGGGGCTAACG

AAACCTTTT-3'
and (SEQ ID NO: 111)
5'-AAAAAAAAGGTTTCCGTTAGCCCCGTCTCTTGAACGGGGCTAACGG AAACCTTTT-3' for psiU6BX-KRZFPUH4.
```

The target sequence of siRNA in each of the sequences is underlined.

psiU6BX-KRZFPUH, psiU6BX-EGFP or psiH1BX-mock plasmid was transfected into cells using FuGENE6 reagent according to the supplier's recommendations (Roche). Total RNA was extracted from the cells 48 hours after the transfection.

Figure 12:
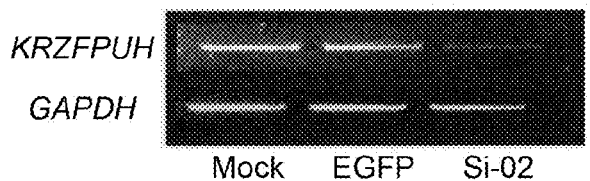
FIGS. 12A to 12D depict the growth suppressive effect of KRZFPUH-siRNAs on the expression of KRZFPUH in Huh7 cells.
Figure 12:
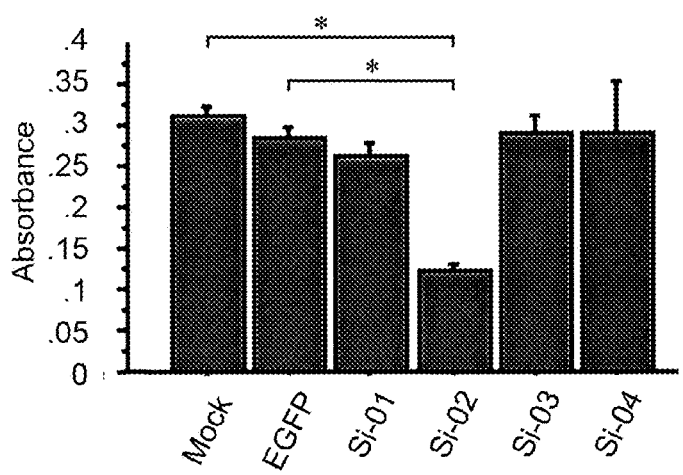
Figure 12:
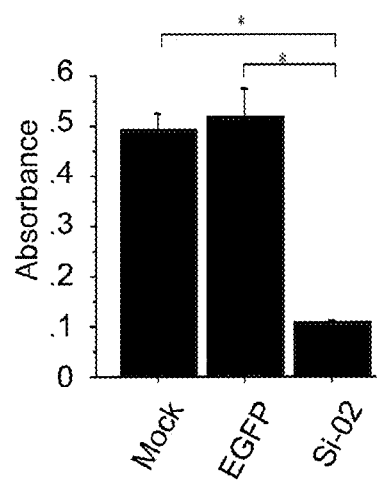
Figure 12:
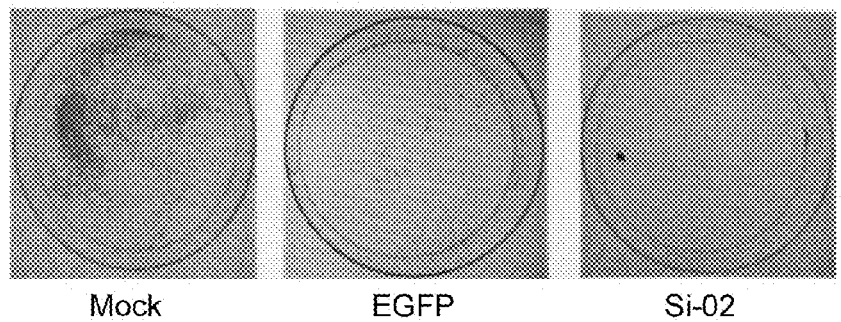
Figure 13:
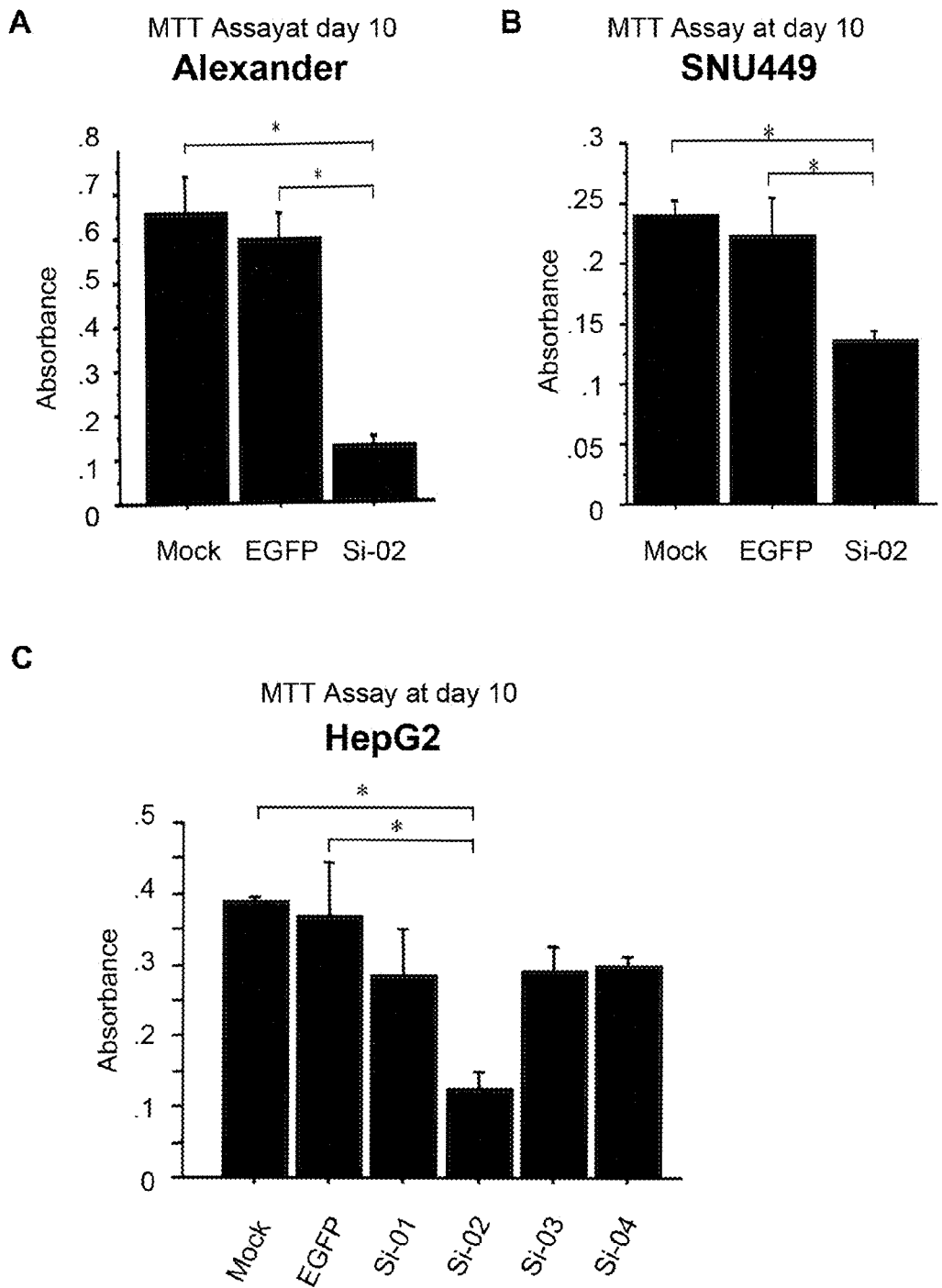
FIGS. 13A to 13C depict the effect of KRZFPUH-siRNAs on the viability of various cells.

In mammalian cells, short interfering RNA (siRNA) composed of 20 or 21-mer double-stranded RNA (dsRNA) with 19 complementary nucleotides and 3' terminal complementary dimmers of thymidine or uridine, have been recently shown to have a gene specific gene silencing effect without inducing global changes in gene expression. Therefore, plasmids expressing various KRZFPUH-siRNAs were constructed and examined for their effect on KRZFPUH expression. Among the siRNAs, psiU6BX-KRZFPUH2 but not psiU6BX-KRZFPUH1, psiU6BX-KRZFPUH3 or psiU6BX-KRZFPUH4 significantly suppressed the expression of KRZFPUH in Huh7, Alexander, HepG2 and SNU449 cells (FIGS. 12 and 13, data not shown). To test whether the suppression of KRZFPUH may result in growth suppression of hepatoma cells, Huh7, Alexander cells were transfected with psiU6BX-KRZFPUH2, psiH1BX-KRZFPUH1, psiH1BX-KRZFPUH3, psiH1BX-KRZFPUH4, psiH1BX-EGFP or mock vector. Viable cells transfected with psiU6BX-KRZFPUH2 were markedly reduced compared to those transfected with psiH1BX-KRZFPUH1, psiH1BX-KRZFPUH3, psiH1BX-KRZFPUH4, psiU6BX-EGFP or the control suggesting that decreased expression of KRZPUH suppresses the growth of hepatoma cells (FIGS. 12 and 13).

Example 13

Figure 14:
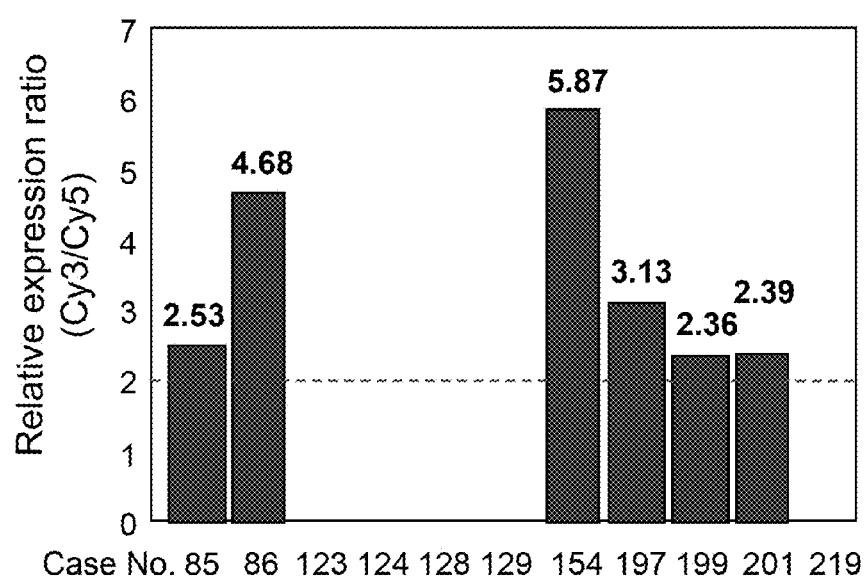
FIGS. 14a and 14b depict the expression of PPIL1 in colon cancer.
Figure 14:
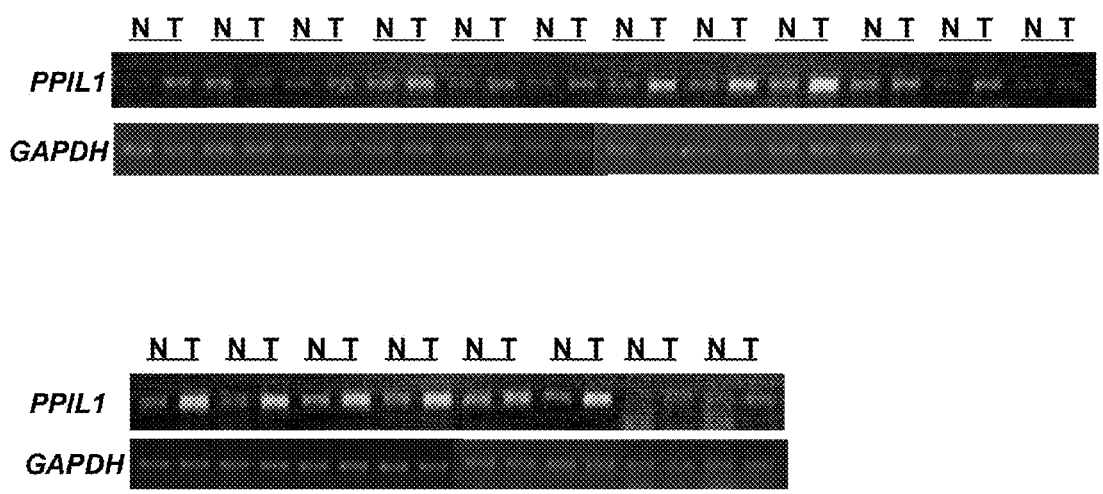

Identification of Novel Gene, PPIL1, Commonly Up-Regulated in Human Colon Cancer The expression profiles of 11 colon cancer tissues were compared with their corresponding non-cancerous mucosal tissues of the colon as in Example 1 using the cDNA microarray containing 23040 genes. This analysis identified a number of genes which expression levels were frequently elevated in cancer tissues compared to their corresponding non-cancerous tissues. Among them, a gene with an in-house accession number of B9486, corresponding to the CGI-124/PPIL1 gene (GenBank Accession number: AF151882) was revealed to have enhanced expression levels in the cancer tissues compared to their corresponding non-cancerous mucosae in a magnification range between 2.36 and 4.68 in all six cases that passed the cut-off filter (FIG. 14a). To clarify the results of the microarray, expression of these transcripts in additional colon cancer samples was examined by semi-quantitative RT-PCR as in Example 1 using primers: 5'-GGACAGGTCGAGGTGGTGC-3' (forward) [SEQ ID NO: 39] and 5'-CTCGACGAGTTC TCCCATCG-3' (reverse) [SEQ ID NO: 40]. According to the semi-quantitative RT-PCR, the expression of PPIL1 was confirmed to be increased in 17 of the 20 cases (FIG. 14b).

Example 14

Structure of PPIL1

Figure 15:
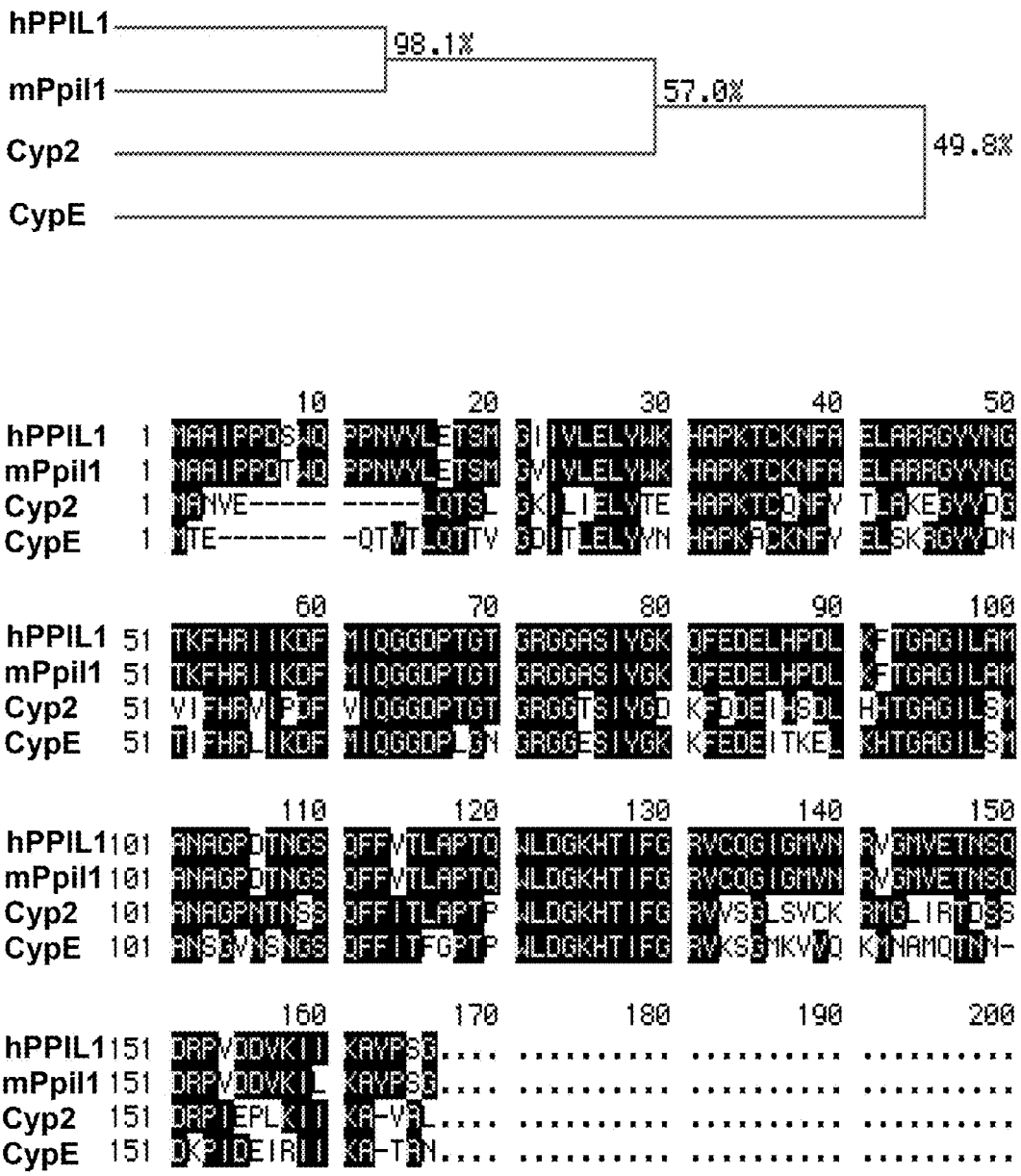
FIG. 15 depicts the similarity between PPIL1 (*Homo sapiens*), Ppil1 (*Mus musculus*), Cyp2 (*Schzosaccharomyces pombe*), and CypE (*Dictiostelium discoideum*).

Additional homology searches on the sequence of AF151882 corresponding to PPIL1 in public databases using BLAST program in the National Center for Biotechnology Information (see the world wide web at ncbi.nlm.nih.gov/BLAST/) identified ESTs including BE908798, AK026636 that contained 5' or 3' part of PPIL1, respectively, and a genomic sequence (GenBank Accession No. NT_007592) that had been assigned to chromosomal band 6p21.1. The assembled cDNA sequence of PPIL1 had 1734 nucleotides containing an open reading frame of 498 nucleotides. Comparison of the cDNA sequence with the genomic sequence disclosed that this gene consists of 4 exons. The predicted amino acid sequence of this gene shared 98% identity with that of murine (FIG. 15). The determined nucleotide sequence of PPIL1 and its predicted amino acid sequence are shown in SEQ ID NOs: 5 and 6, respectively.

Example 15

Effect of PPIL1 on Cell Growth

To investigate the effect of PPIL1 on cell growth, colony-formation assay by transfecting NIH3T3 cells (ATCC, Rockville, Md.) with a plasmid expressing myc-tagged PPIL1 protein (pcDNA3.1myc/His-PPIL1) was carried out. The plasmid was constructed as follows. First, total RNA was extracted with Qiagen RNeasy kit (Qiagen) or Trizol reagent (Life Technologies, Inc.) according to the manufacturers' protocol. Ten-microgram aliquot of total RNA were reverse transcribed into cDNAs using poly $dT_{12-18}$ primer (Amersham Pharmacia Biotech) with Superscript II reverse transcriptase (Life Technologies). Obtained single-stranded cDNA preparation was diluted in 20 µl of PCR buffer (TaKaRa). Then PCR amplification by standard RT-PCR experiment was conducted to amplify the entire coding region corresponding to PPIL1 using following primers: 5'-AGACAAGCTTTCCGCCGCCGGC-3' (forward) [SEQ ID NO: 41] and 5'-GTCTCTCGAGAAGGGTATGCCTTAATGATCTTC-3' (reverse) [SEQ ID NO: 42].

Figure 16:
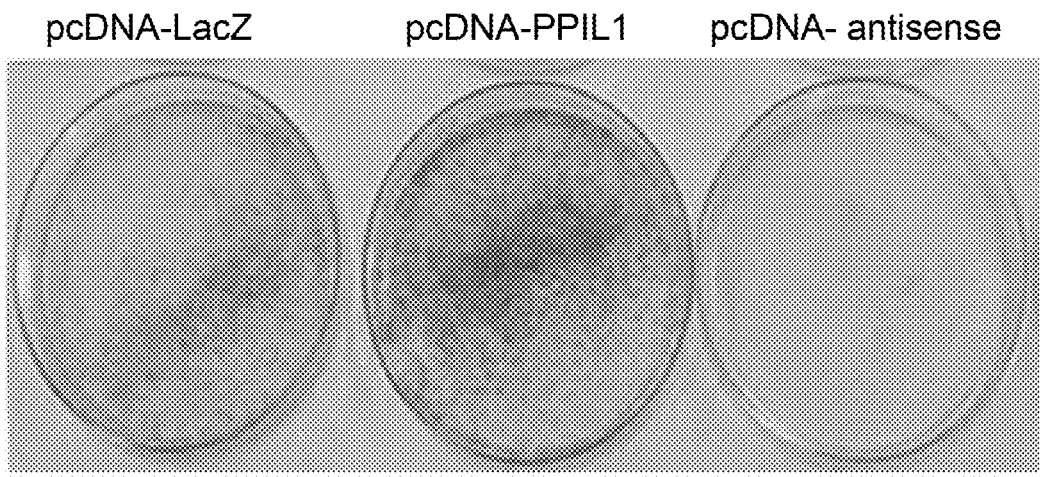
FIG. 16 depicts the effect of PPIL1 on the cell growth of NIH3T3 and HCT116 cells.
Figure 16:
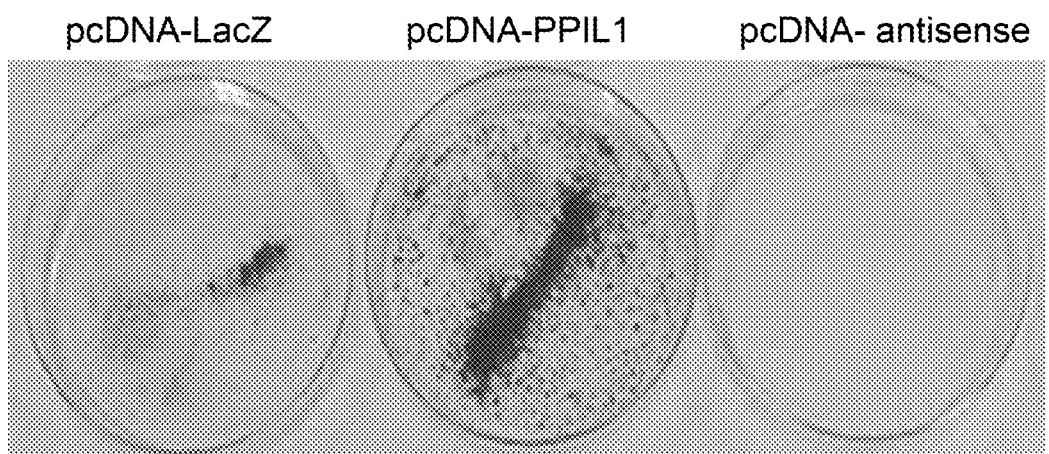

RT-PCR was conducted using GeneAmp PCR system 9700 (Perkin-Elmer, Foster City, Calif.) under following condition: denaturing at 94° C. for 4 min; 28 cycles of 94° C. for 30 s, 56° C. for 30 s, and 72° C. for 45 s. The amplified fragment was inserted into pcDNA3.1myc/His (Invitrogen) vector. Then the constructed pcDNA3.1myc/His-PPIL1 was transfected into NIH3T3 cells.

pcDNA3.1myc/His-PPIL1 induced markedly more colonies in NIH3T3 cells compared with control plasmids, pcDNA3.1myc/His-LacZ or pcDNA3.1myc/His-asPPIL1, that express the complementary strand of PPIL1 (FIG. 16a).

Further, a similar experiment as above was conducted except that HCT116 human colon cancer cells (ATCC, Rockville, Md.) that express low amount of endogenous PPIL1 were used as cells to be transfected with pcDNA3.1myc/His-PPIL1. As a result, enhanced activity of colony formation was observed in the transfected HCT116 human colon cancer cells (FIG. 16b).

Example 16

Growth Suppression of Colon Cancer Cells by Antisense S-Oligonucleotides Designated to Reduce Expression of PPIL1

To test whether suppression of PPIL1 may result in growth retardation and/or cell death of colon cancer cells, four pairs of control and antisense S-oligonucleotides corresponding to PPIL1 were synthesized: control sense oligonucleotide PPIL1-S2, 5'-CTTCGCTATGGCGGCA-3' [SEQ ID NO: 43]; antisense S-oligonucleotide PPIL1-AS2, 5'-TGCCGCCATAGCGAAG-3' [SEQ ID NO: 44]; and scramble S-oligonucleotide PPIL1-SCR2, 5'-GTTGCACAGCGACGCA-3' [SEQ ID NO: 92]. Each of the synthesized oligonucleotides was transfected, using LIPOFECTIN Reagent (GIBCO BRL), into human colon cancer cells SW480 (ATCC, Rockville, Md.), SNU-C4 and SNU-C5 (both from Korea Cell-line bank), which had shown higher levels of PPIL1 expression among examined 11 colon cancer cell lines. SW480 was cultured in Leibovitz's L-15, and SNU-C4 and SNU-C5 in RPMI1640, all medium supplemented with appropriate concentration of geneticin, for six to twelve days. The cells were then fixed with 100% methanol and stained by Giemsa solution.

Figure 17:
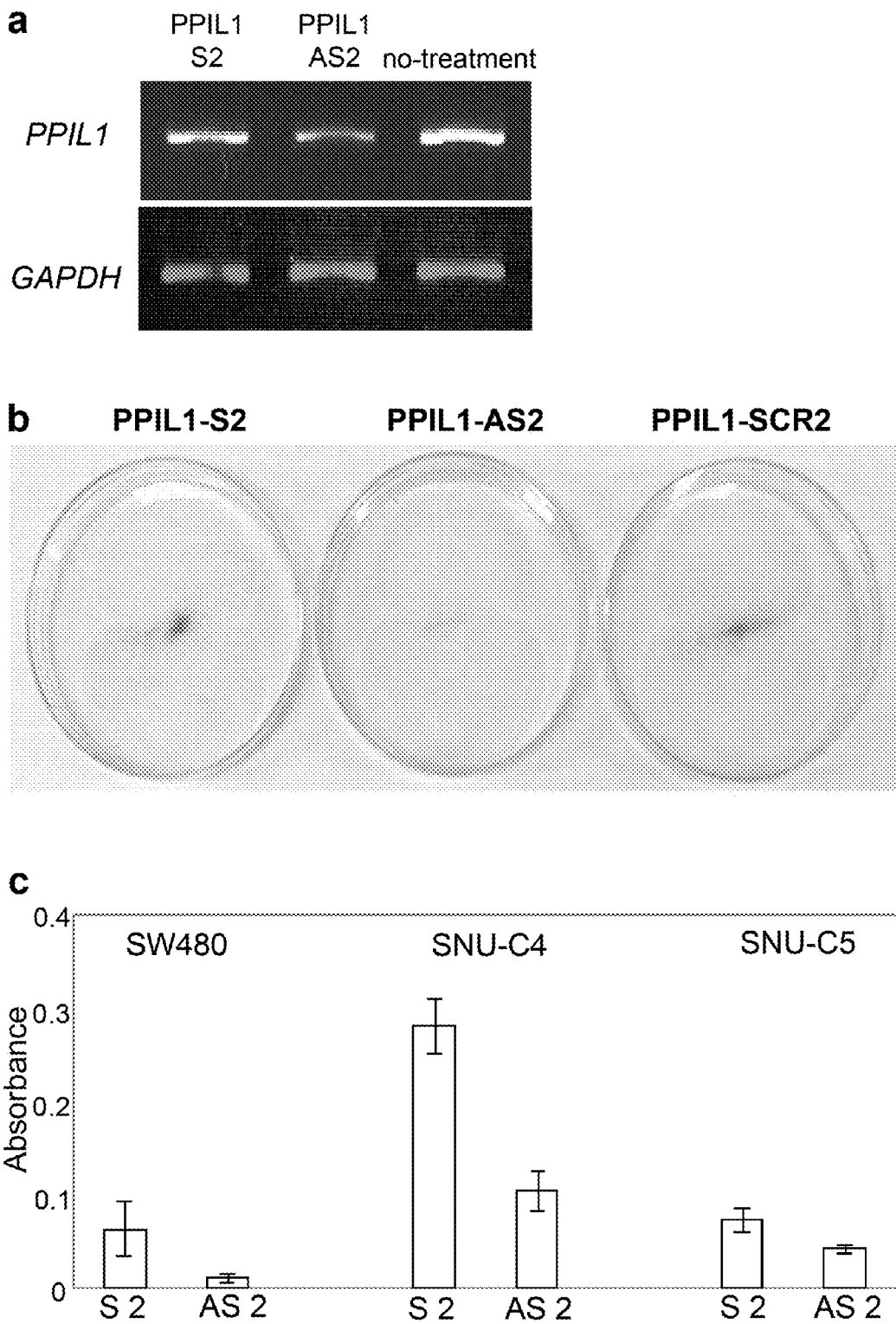
FIGS. 17a to 17c depict the growth suppressive effect of antisense S-oligonucleotides of PPIL1 in human colon cancer cell line, SW480.

Among the antisense S-oligonucleotides, PPIL1-AS2 significantly reduced the expression of PPIL1 compared to control sense (PPIL1-S2) in SNU-05 cells (FIG. 17a). Six days after transfection, the number of surviving cells transfected with PPIL1-AS2 was significantly fewer than that with controls, PPIL1-S2 or scramble S-oligonucleotides (PPIL1-SCR2), suggesting that suppression of PPIL1 reduced growth and/or survival of transfected cells (FIG. 17b). Consistent results were obtained in three independent experiments.

3-(4,5-dimethylthiazol-2-yl)-2,5-diphenyltetrazolium bromide (MTT) assay was additionally carried out to measure the growth-inhibitory effect of PPIL1-AS2 in SW480, SNU-C4 and SNU-C5 cells. Specifically, cells plated at a density of $5\times10^5$ cells/100 mm dish were transfected in triplicate with sense or antisense S-oligonucleotides designated to suppress PPIL1. 72 h after the transfection, the medium was replaced with fresh medium containing 500 µg/ml of MTT (Sigma) and the plates were incubated for 4 h at 37° C. Subsequently, the cells were lysed by the addition of 1 ml of 0.01 N HCl/10% SDS and the absorbance of lysates was measured with ELISA plate reader at a test wavelength of 570 nm (reference, 630 nm). The cell viability was represented by the absorbance compared to that of control cells. As a result, the number of viable cells transfected with PPIL1-AS2 was significantly fewer than that with PPIL1-S2 in these three cell lines (FIG. 17c).

Example 17

Interaction of PPIL1 Protein with SNW1

Two prokaryotic proteins, Cyp2 (*Schizosaccharomyces pombe*) and CypE (*Dictiostelium discoideum*), highly homologous to PPIL1 were reported to interact with Snw1 and SnwA, respectively. Thus, PPIL1 protein was hypothesized to be associated with SNW1/SKIP, a human homologue of Snw1 and SnwA. To investigate this hypothesis, pFLAG-PPIL1 expressing Flag-tagged PPIL1 protein was constructed. First, the entire coding region of PPIL1 was amplified as in Example 15 and the product was cloned into the cloning site of pFLAG-CMV-5c (Sigma) to prepare pFLAG-PPIL1. Similarly, the entire coding region of SNW1 was amplified by RT-PCR using gene specific primer set: 5'-TGGGAAQTTCCGGAAGAAGATGGCGCT-CACCAGC-3' (forward) [SEQ ID NO: 45] and 5'-GTGC-CTCGAGCTTCCTCCTCTTCTTGCCTTCATGC-3' (reverse) [SEQ ID NO: 46]; and cloned into the cloning site of pcDNA3.1myc/His (Invitrogen) to construct pcDNA3.1myc-SNW1 that expresses myc-tagged SNW1. Next, pFLAG-PPIL1 was transfected either with or without pcDNA3.1myc-SNW1 into COS7 cells (ATCC, Rockville, Md.).

Then, immunoprecipitation of the cell lysates with anti-FLAG antibody was conducted as follows: COS7 cells transfected with pFLAG-PPIL1 and pcDNA3.1myc/His-SNW1 were harvested 48 h after the transfection and lysed with lysis buffer containing 20 mM Tris-HCl pH7.5, 150 mM NaCl, 1% NP-40, and 1× complete Protease Inhibitor Cocktail EDTA (−) (Boehringer). Cell lysates were immunoprecipitated with anti-FLAG M2 antibody (SIGMA). The precipitated protein was separated by SDS-PAGE and immunoblot analysis was carried out using anti-FLAG M2 antibody.

Following the immunoprecipitation, immunoblot analysis with anti-c-Myc antibody was conducted. Specifically, cells transfected with pFLAG-PPIL1 and/or pcDNA3.1myc/His-SNW1 were washed twice with PBS and harvested in lysis buffer (150 mM NaCl, 1% Triton X-100, 50 mM Tris-HCl pH 7.4, 1 mM DTT, and 1× complete Protease Inhibitor Cocktail (Boehringer)). After the cells were homogenized and centrifuged at 10,000×g for 30 min, the supernatant were standardized for protein concentration by the Bradford assay (Bio-Rad). Proteins were separated by 10% SDS-PAGE and immunoblotted with mouse anti-myc antibody (SANTA CRUZ). HRP-conjugated goat anti-mouse IgG (Amersham) served as the secondary antibody for the ECL Detection System (Amersham).

Figure 18:
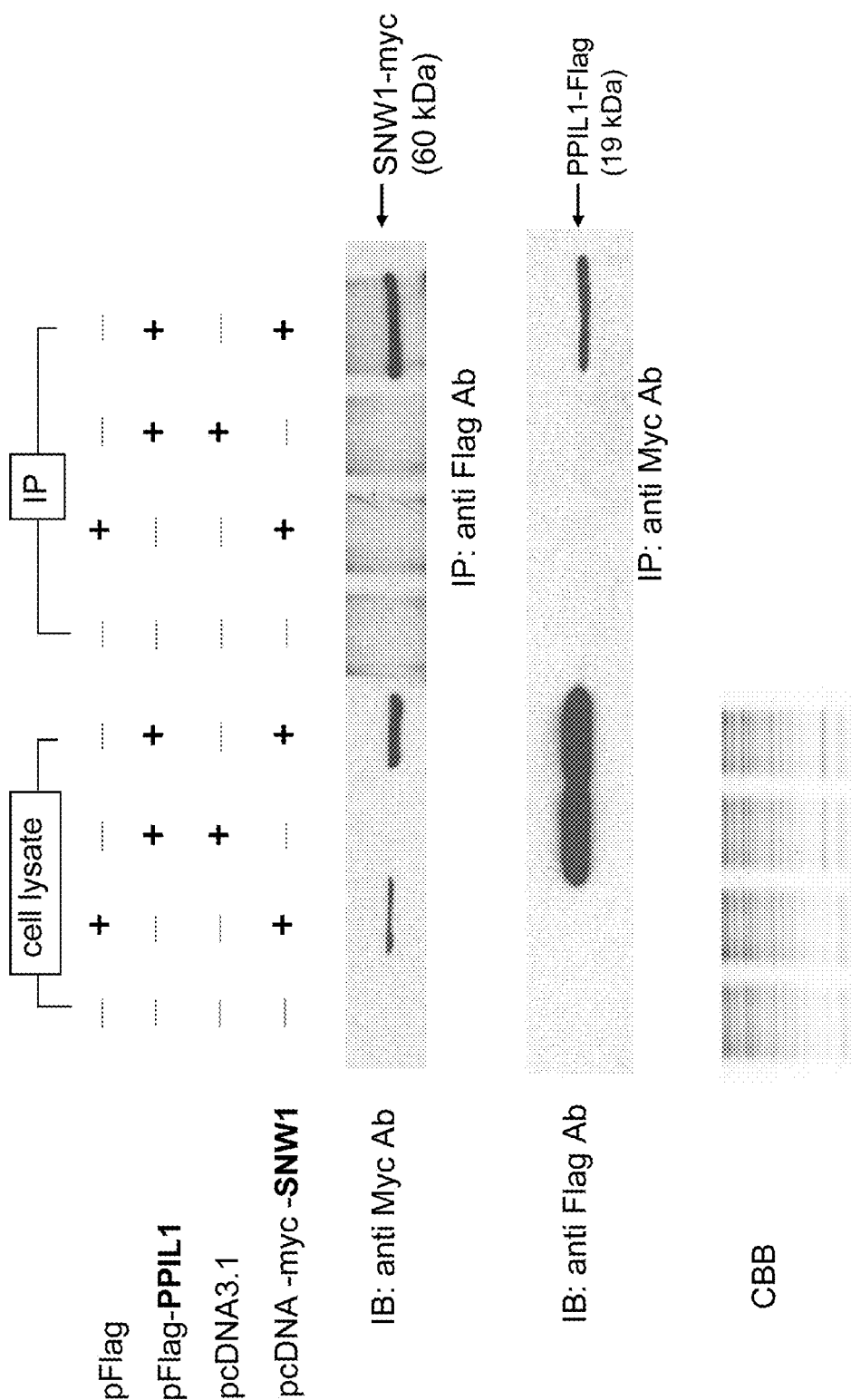
FIG. 18 presents photographs demonstrating that PPIL1 associates with SNW1 in vitro. COS7 cells were co-transfected with pFLAG CMV-PPIL1 and pcDNA3.1myc/His-SNW1. Lysates from the cells were immunoprecipitated with either anti c-Myc polyclonal antibody or anti FLAG monoclonal antibody, and immunoblot was performed with anti-FLAG monoclonal antibody or anti c-Myc polyclonal antibody, respectively.

The results demonstrated that bands corresponding to myc-tagged SNW1 protein were observed when cells were co-transfected with both plasmids (FIG. 18). Moreover, immunoprecipitation of the lysates with anti-cMyc antibody precipitated Flag-tagged PPIL1 protein. These results corroborated that PPIL1 can associated with SNW1 by either directly or indirectly in vivo.

Example 18

Co-Localization of PPIL1 with SNW1

To further confirm the association of PPIL1 with SNW1, subcellular localization of FLAG-tagged PPIL1 protein and myc-tagged SNW1 protein in COST cells was examined by immunohistochemical staining of cells co-transfected with pFLAG-PPIL1 and pcDNA3.1myc-SNW1 using anti-FLAG antibody. Specifically, cells transfected with pFLAG-PPIL1 and pcDNA3.1myc/His-SNW1 were fixed with PBS containing 4% paraformaldehyde for 15 min, then rendered permeable with PBS containing 0.1% Triton X-100 for 2.5 min at RT. Subsequently the cells were covered with 2% BSA in PBS for 24 h at 4° C. to block non-specific hybridization. 1:1000 diluted mouse anti-myc monoclonal antibody (Sigma) or 1:2000 diluted mouse anti-FLAG antibody (Sigma) was used for the first antibody, and the reaction was visualized after incubation with Rhodamine-conjugated anti-mouse second antibody (Leinco and ICN). Nuclei were counter-stained with DAPI. Fluorescent images were obtained under an ECLIPSE E800 microscope.

Figure 19:
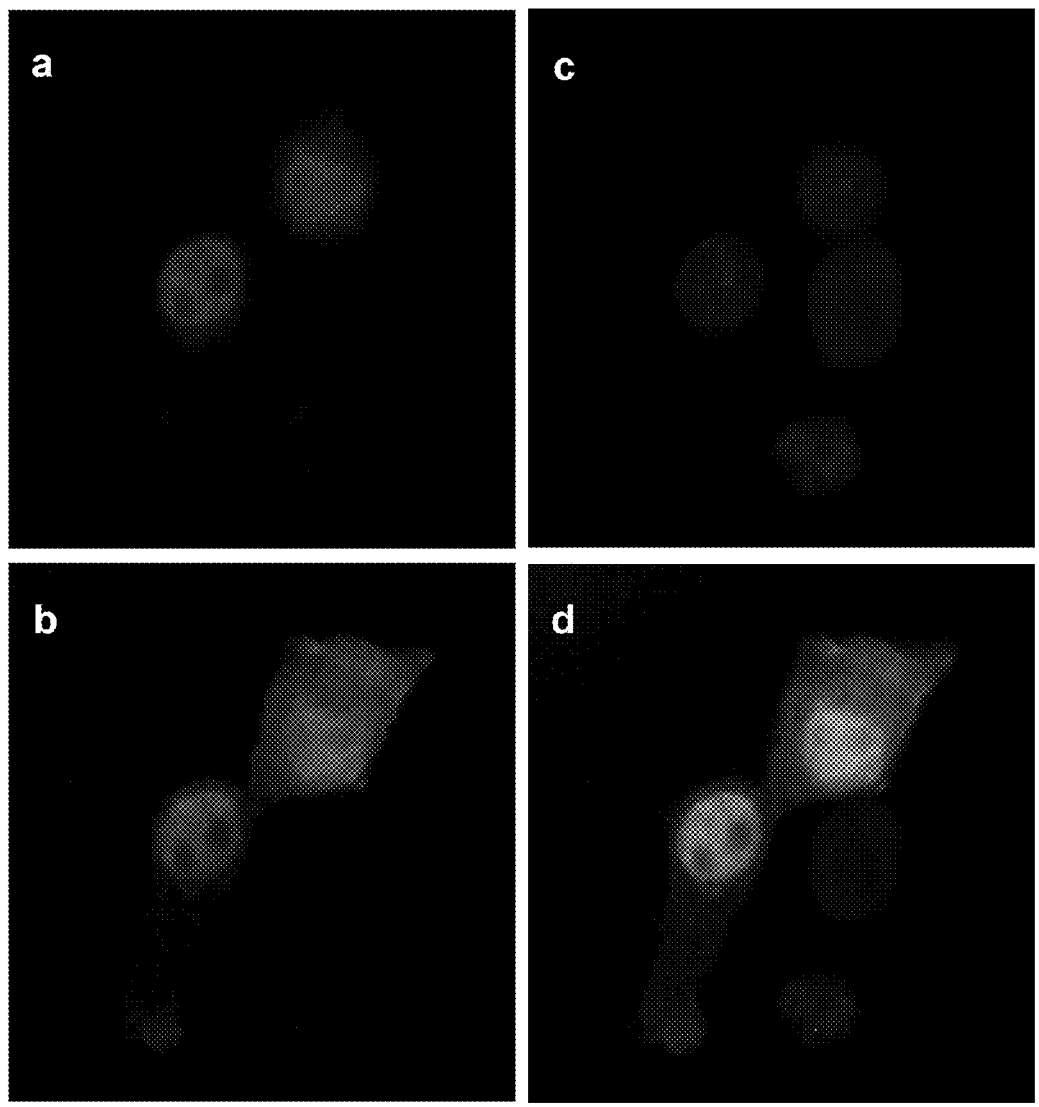
FIGS. 19a to 19d presents photographs depicting the subcellular localization of FLAG-tagged PPIL1 and myc-tagged SNW1 protein.

The immunohistochemical staining of the cells with anti-FLAG antibody demonstrated signals in the nucleus and that with anti-myc antibody revealed similar positive staining in the nucleus and cytoplasm. Merged image of (FIGS. 19a and b) and counter-staining with DAPI (FIG. 19c) showed co-localization of FLAG-tagged PPIL1 protein and myc-tagged SNW1 protein in the nucleus (FIG. 19d), in line with the notion of interaction between PPIL1 and SNW1.

Example 19

Expression of PPIL1 in Human Multiple Tissues

Multi-tissue northern blot analysis using PPIL1 cDNA as a probe was conducted. Specifically, human multiple-tissue blots (Clontech, Palo Alto, Calif.) were hybridized with a $^{32}$P-labeled PCR product of PPIL1. Pre-hybridization, hybridization, and washing were performed according to the supplier's recommendations. The blots were autoradiographed with intensifying screens at −80° C. for 24 to 72 h.

Figure 20:
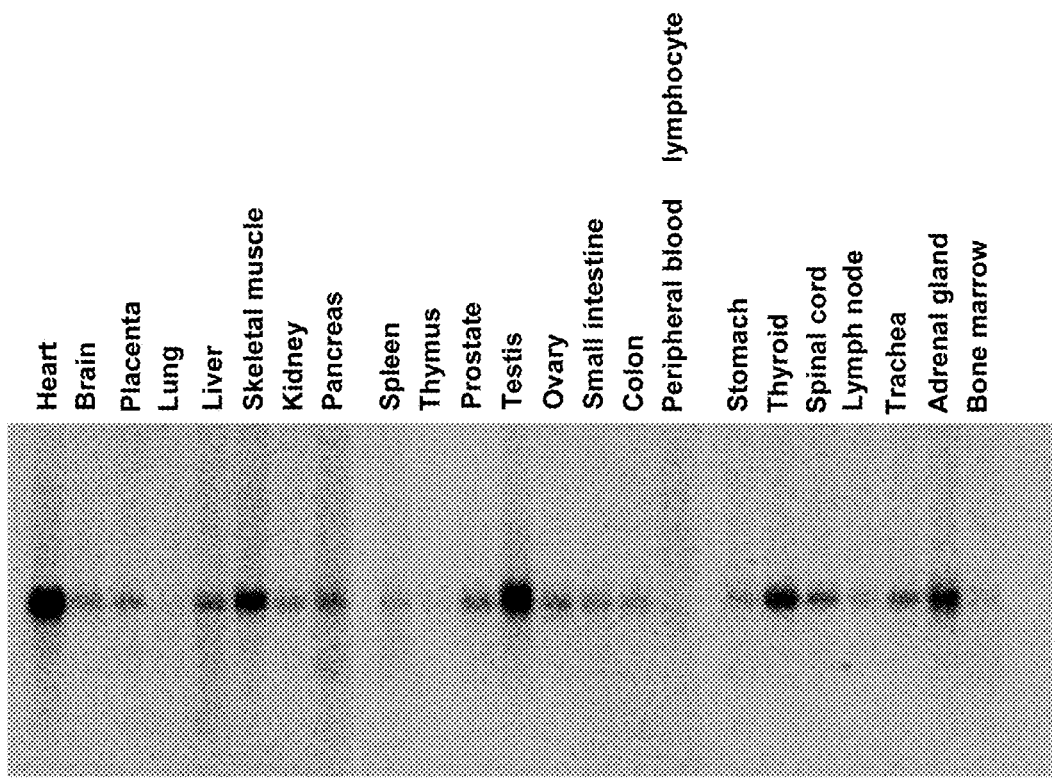
FIG. 20 is a photograph depicting the expression of PPIL1 in various human tissues analyzed by multiple-tissue northern blot analysis.

The result showed ubiquitous expression of a 1.7 kb transcript expressed. Among the tissues examined, abundant expression was observed in the heart, skeletal muscle, testis, thyroid and adrenal gland (FIG. 20).

Example 20

Construction of Plasmids Expressing PPIL1 siRNAs and their Effect on Growth of Colon Cancer Cells Plasmids expressing various PPIL1-siRNAs were constructed to examine their effect on PPIL1 expression. First, psiH1BX3.0 vector was constructed similarly to Example 6. Further, the control vector psiH1BX-EGFP was also prepared as in Example 6. Then, plasmids expressing PPIL1-siRNAs were prepared by cloning double-stranded oligonucleotides into the BbsI site of the psiH1BX3.0 vector. The oligonucleotides cloned into the vector was as follows:

```
psiH1BX-PPIL-A,
                                          [SEQ ID NO: 47]
5'-TCCCGCATGCTCCAAAGACCTGTTTCAAGAGAACAGGTCTTT

GGAGCATGC-3' and
                                          [SEQ ID NO: 48]
5'-AAAAGCATGCTCCAAAGACCTGTTCTCTTGAAACAGGTCTTT

GGAGCATGC-3';

psiH1BX-PPIL-B,
                                          [SEQ ID NO: 49]
5'-TCCCAGACTTCATGATCCAAGGATTCAAGAGATCCTTGGATC

ATGAAGTCT-3' and
                                          [SEQ ID NO: 50]
5'-AAAAAGACTTCATGATCCAAGGATCTCTTGAATCCTTGGATC

ATGAAGTCT 3';

and psiH1BX-PPIL-C,
                                          [SEQ ID NO: 51]
5'-TCCCTGGCAGCCAGTTCTTTGTGTTCAAGAGACACAAAGAAC

TGGCTGCCA-3' and
```

-continued

[SEQ ID NO: 52]
5'-AAAA<u>TGGCAGCCAGTTCTTTGTGT</u>CTCTTGAACACAAAGAAC
TGGCTGCCA-3'.

The target sequence of siRNA in each of the sequences is underlined.

The plasmids were transfected into colon cancer cells SNUC4 or SNUC5 using FuGENE6 reagent (Roche) according to the supplier's recommendations. Total RNA was extracted from the cells 48 h after the transfection.

Figure 21:
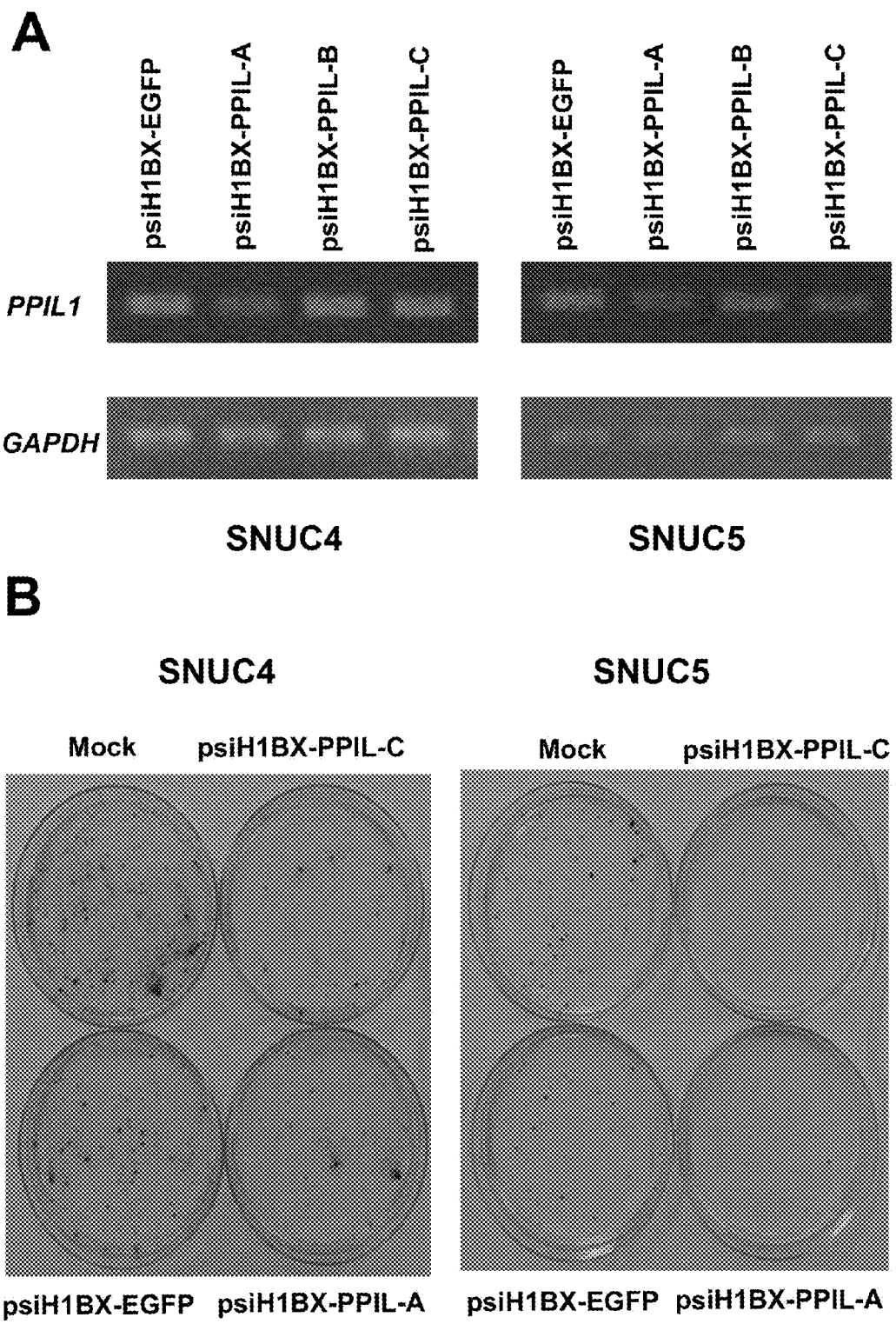
FIGS. 21A and 21B depict the growth suppressive effect of PPIL1-siRNAs in SNUC4 and SNUC5 cells.

Among them, psiH1BX-PPIL-A but not psiH1BX-PPIL-B or psiH1BX-PPIL-C significantly suppressed expression of PPIL1 in SNUC4 as well as SNUC5 cells (FIG. 21A). To test whether suppression of PPIL1 may result in growth suppression of colon cancer cells, SNUC4 and SNUC5, cells were transfected with psiH1BX-PPIL-A, psiH1BX-PPIL-B, psiH1BX-PPIL-C or a control psiH1BX-EGFP. Viable cells transfected with psiH1BX-PPIL-A were markedly reduced compared to those transfected with psiH1BX-PPIL-B, psiH1BX-PPIL-C, or psiH1BX-EGFP, suggesting that decreased expression of PPIL1 suppressed growth of colon cancer cells (FIG. 21B).

Example 21

Preparation of Recombinant PPIL1 Protein

Figure 22:
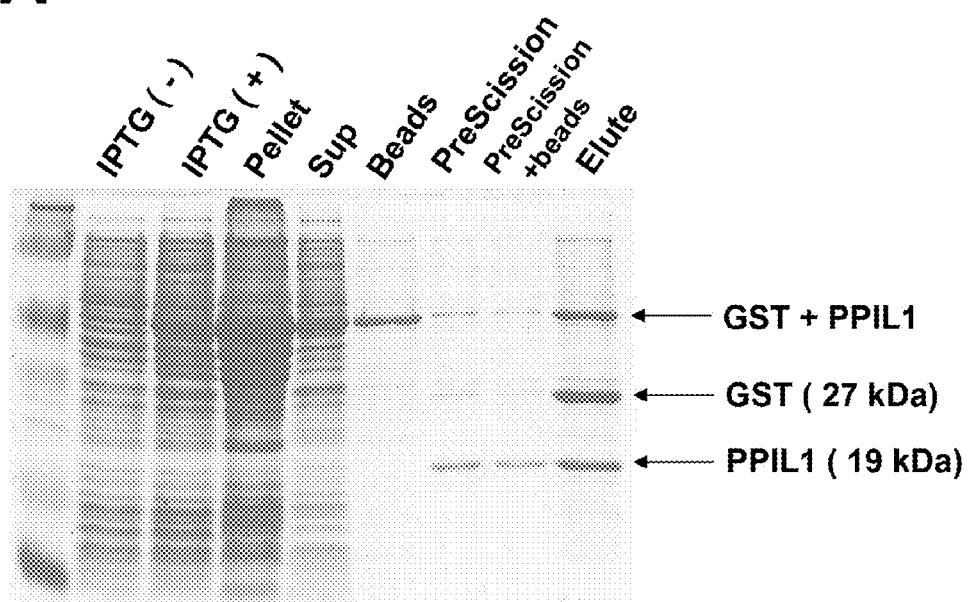
FIGS. 22A and 22B depict the expression of PPIL1 recombinant protein in *E. coli*.
Figure 22:
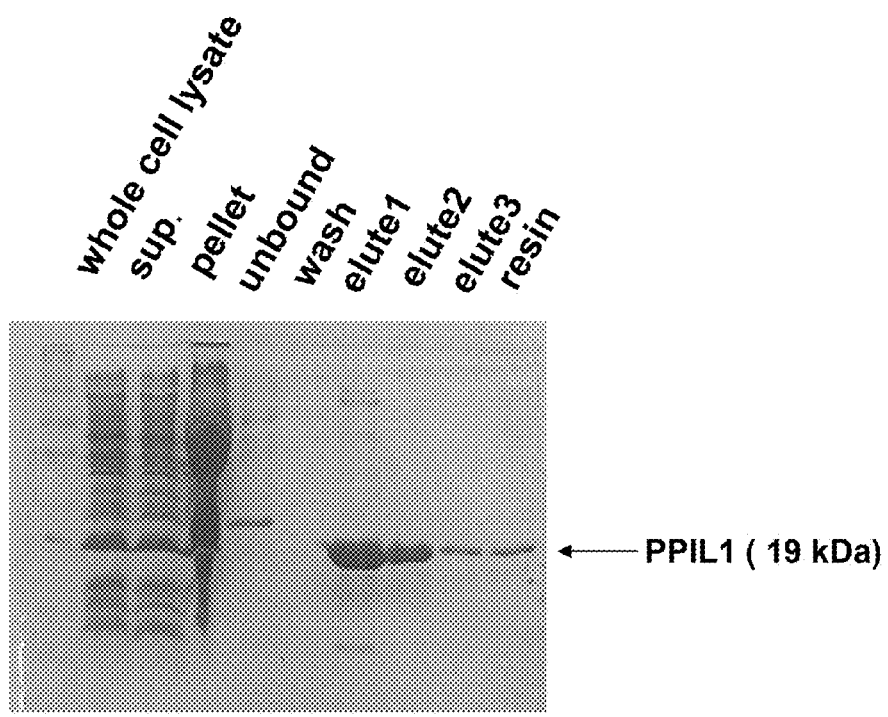

To generate specific antibody against PPIL1, recombinant protein of PPIL1 was prepared. The entire coding region of PPIL1 was amplified by RT-PCR with a set of primers, 5'-CGCCGGATCCGCTATGGCGGCAATTCCCCCAG-3' [SEQ ID NO: 53] and 5'-AGCACTCGAGCCCAGAAGGG-TATGCCTTAATGATC-3' [SEQ ID NO: 54]. The product was purified, digested with BamH1 and Xho1, and cloned into an appropriate cloning site of pGEX-6P-1 (pGEX-PPIL1) or pET21a (pET-PPIL1) vector. pGEX-PPIL1 or pET-PPIL1 was transformed into E. coli DH10B or BL21 codon plus cells. Recombinant protein was induced by the addition of IPTG, and purified from the extracts according to the manufacturers' protocols. When the plasmids were transformed into E. coli cells, production of recombinant protein at the expected size on SDS-PAGE could be observed (FIGS. 22A and B).

Example 22

Identification of Stathmin as a PPIL1-Interacting Protein by a Bacterial Two-Hybrid Screening System To analyze the function of PPIL1, PPIL1-interacting proteins were searched using bacterial two-hybrid screening system. The bacterial two-hybrid assay was performed with the BacterioMatch Two-Hybrid System (Stratagene) according to the manufacturer's protocols. The entire coding sequence of PPIL1 obtained as in Example 21 was cloned into the BamH1-Xho1 site of pBT vector as bait and screened a human fetal brain cDNA library (Stratagene). Among the positive clones identified, stathmin showed an interaction with PPIL1 by simultaneous transformation with pBT-PPIL1 and pTRG-STMN in bacteria (FIG. 23A).

Further, immunoprecipitation assay was conducted. Specifically, COS7 cells were transfected pFLAG-PPIL1 expressing FLAG-tagged PPIL1 prepared as in Example 17, and pCMV-HA-STMN expressing HA-tagged stathmin protein, or their combination, were washed with PBS and lysed in NET-N buffer containing 150 mM NaCl, 1% NP-40, 10 mM Tris-HCl pH8.0, 1 mM EDTA, and 1× complete Protease Inhibitor Cocktail (Roche). In a typical immunoprecipitation reaction, 300 µg of whole-cell extract was incubated with 1 µg of mouse anti-FLAG (SIGMA), or 3 µg of rat anti-HA antibody and 20 µl of protein G Sepharose beads (Zymed) at 4° C. for 1-2 h. Beads were washed five times in 1 ml of NET-N buffer and proteins bound to the beads were eluted by boiling in SDS sample buffer. The precipitated protein was separated by SDS-PAGE and immunoblot analysis was carried out using either anti-HA antibody or anti-FLAG M2 antibody.

Figure 23:
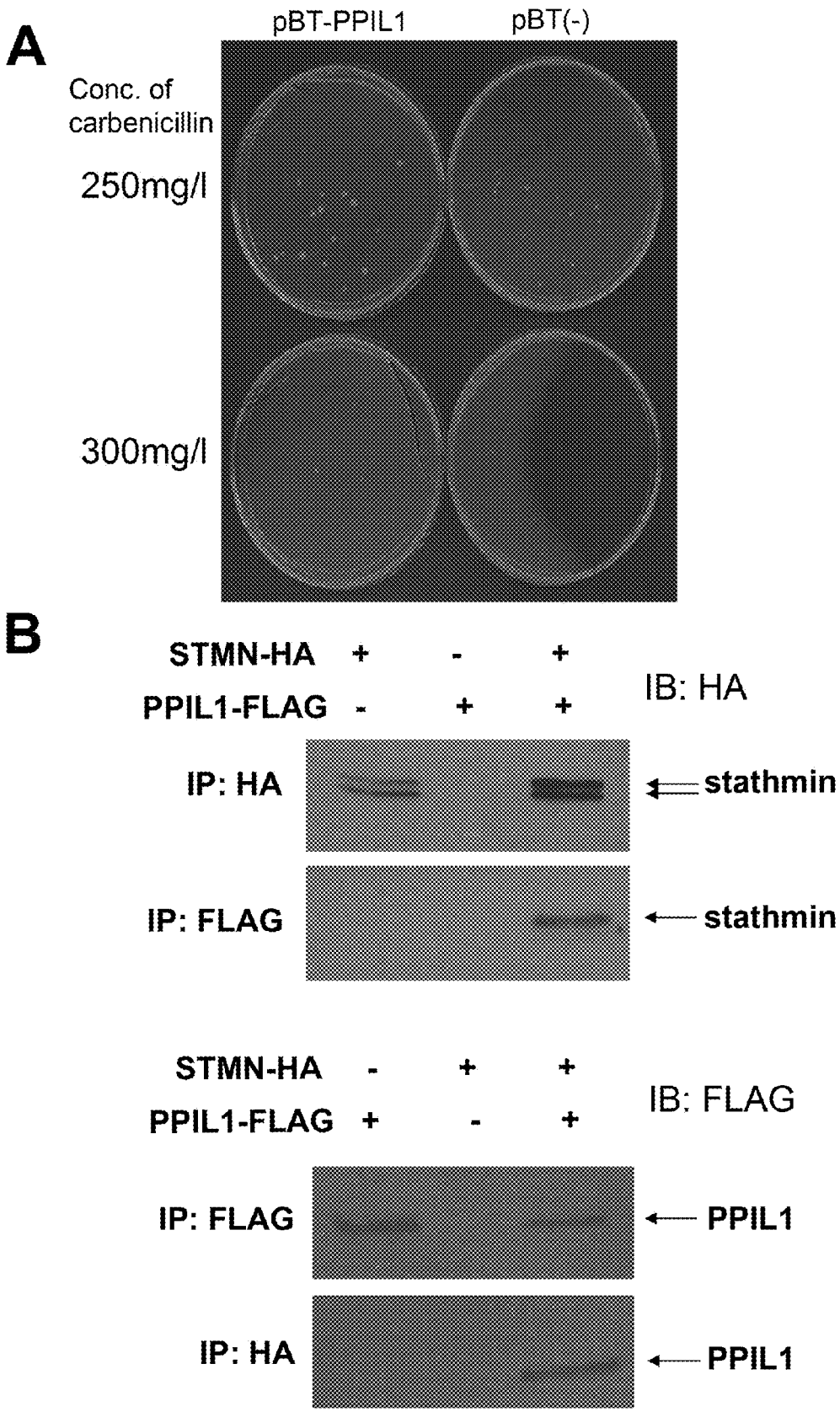
FIGS. 23A and 23B depict the interaction between PPIL1 and stathmin in yeast two-hybrid system.

As described above, the association between FLAG-tagged PPIL1 protein and HA-tagged stathmin protein in vivo was proven by the immunoprecipitation assay in COS7cells (FIG. 23B). Interestingly, Western blot analysis using anti-stathmin antibody revealed two bands corresponding to 18-kDa and 20-kDa protein, suggesting the existence of modified form(s) of stathmin. Since stathmin was shown to have putative serine/threonine phosphorylation sites (Ser16, Ser25, Ser38 and Ser63), the larger band may correspond to the phosphorylated form of stathmin. Furthermore, since the immunoprecipitation with anti-Flag antibody showed a single band corresponding to the 20-kDa protein, PPIL1 may associate with the modified form or increase the modification of stathmin by binding with it.

Example 23

Co-Localization of Flag-Tagged PPIL1 and HA-Tagged Stathmin in Cells

Figure 24:
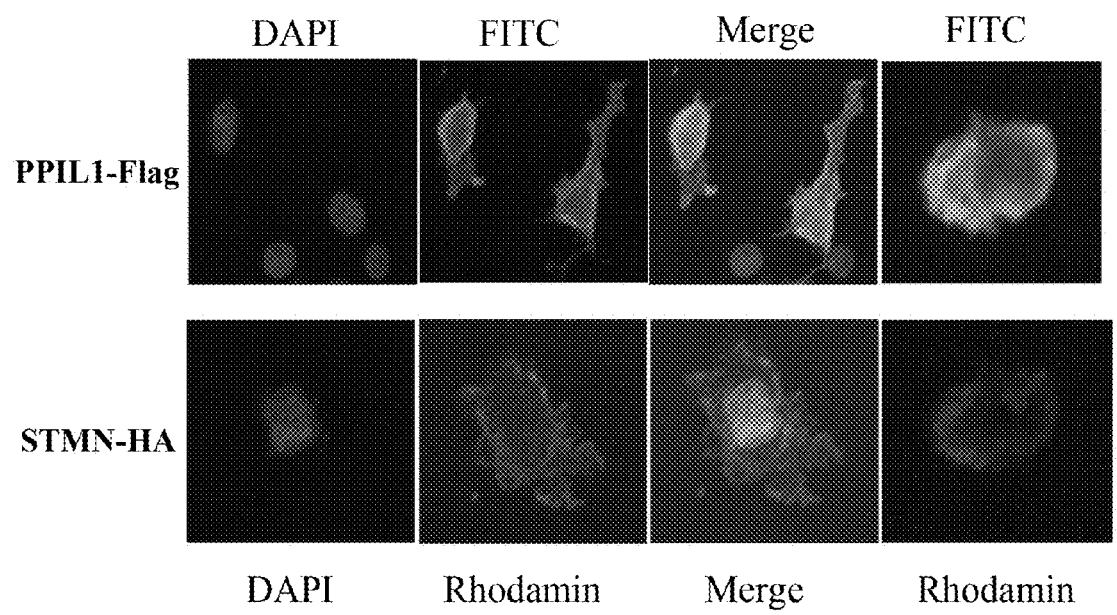
FIG. 24 depict the co-localization of PPIL1 and stathmin in the cytoplasms of COS7 cells co-transfected with pFLAG-PPIL1 and pCMV-HA-STMN.

To test whether PPIL1 and stathmin co-localized in cells, pFLAG-PPIL1 and pCMV-HA-STMN were co-transfected into COS7 cells as in Example 22 to examine their subcellular localization by immunohistochemical staining (FIG. 24). Staining with anti-FLAG antibody revealed that the Flag-tagged PPIL1 localized both in the nucleus and cytoplasm, while that with anti-HA antibody demonstrated that HA-tagged stathmin co-localized with PPIL1 in the cytoplasm. This data supports the view of the interaction between PPIL1 and stathmin in the cytoplasm.

Example 24

Responsible Region of Stathmin for the Interaction with PPIL1

Furthermore, immunoprecipitation assay was performed similar to Example 22 using various deletion mutants of pCMV-HA-STMN and wild-type pFLAG-PPIL1 to clarify the responsible region for the interaction. The deletion mutants of STMN was amplified using primer sets,
5'-ATTGGTACCATGGAGCTGATTCTCAGC-CCTCGGTC-3' [SEQ ID NO: 55] and 5'-AATCTCGAGGT-CAGCTTCAGTCTCGTCAGCAG-3' [SEQ ID NO: 56] for deletion mutant 1;
5'-ATTGGTACCATGGTTCCAGAATTC-CCCCTTTCCCCT-3' [SEQ ID NO: 57] and 5'-AATCTC-GAGGTCAGCTTCAGTCTCGTCAGCAG-3' [SEQ ID NO: 58] for deletion mutant 2;
5'-ATTGGTACCATGGATCTTTCCCTGGAG-GAAATTCAG-3' [SEQ ID NO: 59] and 5'-AATCTCGAG-GTCAGCTTCAGTCTCGTCAGCAG-3' [SEQ ID NO: 60] for deletion mutant 3;
5'-ATTGGTACCATGGCTGAGGTCTTGAAG-CAGCTGGC-3' [SEQ ID NO: 61] and 5'-AATCTCGAGGT-CAGCTTCAGTCTCGTCAGCAG-3' [SEQ ID NO: 62] for deletion mutant 4; and 5'-ATTGGTACCTTCACCATGGCTTCTTCTGATATCC-3' [SEQ ID NO: 63] and 5'-AATCTCGAGGCGTCTTTCTTCTGCAGCTTC-3' [SEQ ID NO: 64] for deletion mutant 5 and the full length clone (pFLAG-PPIL1) as a template. The PCR product was cloned into the Kpn1 and Xho1 site of pcDNA3.1myc/His.

Figure 25:
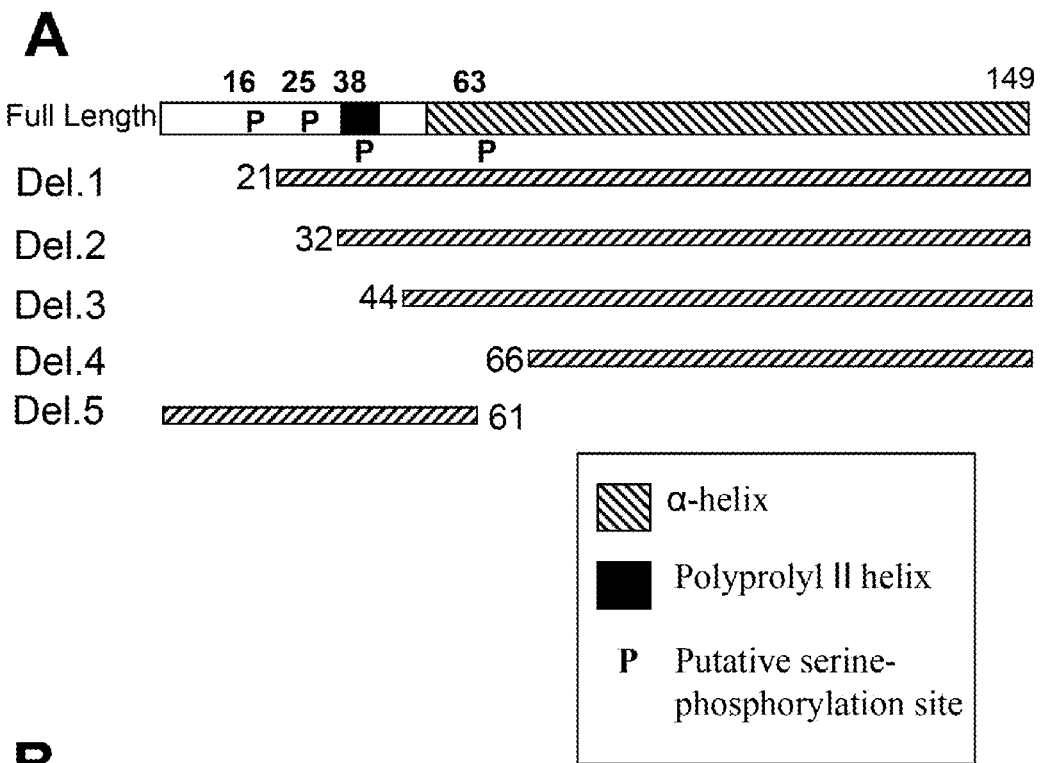
FIGS. 25A and 25B depict the interaction of various deletion mutants of stathmin with PPIL1 in vivo.
Figure 25:
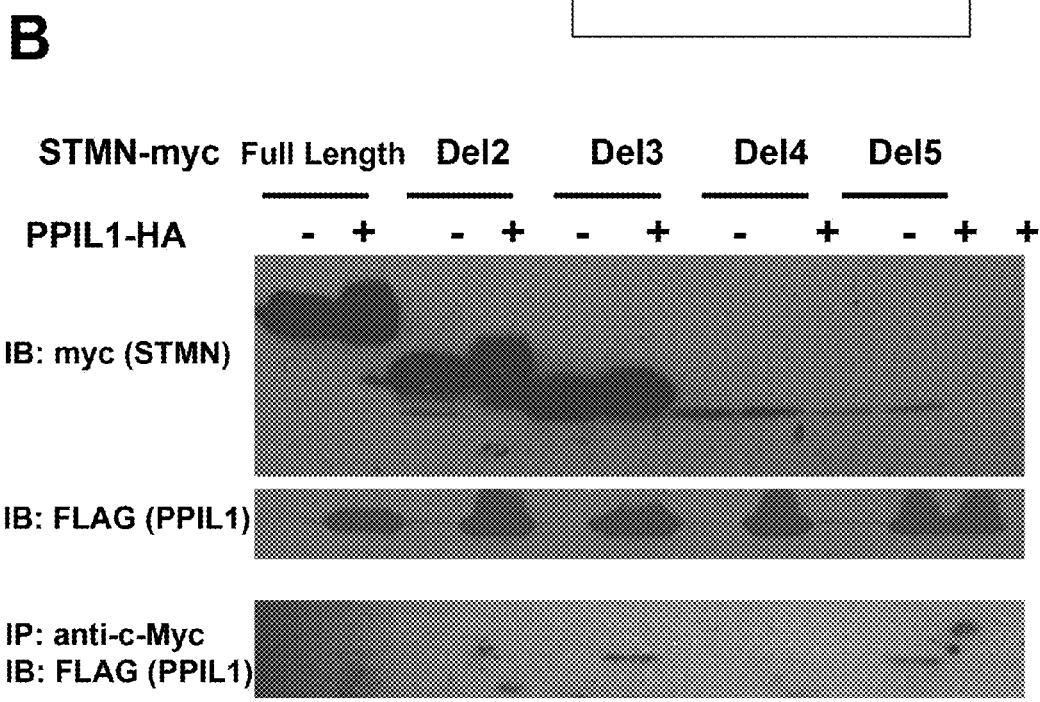

A deletion mutant (Del3) lacking amino acids 1-43 of stathmin was able to associate with PPIL1 but a mutant lacking 1 to 65 (Del 4) failed. Meanwhile, another mutant containing amino acids 1 to 61 was capable for the binding (FIGS. 25A and B), indicating that a region encompassing between codons 44 and 61 is crucial for the binding.

Example 25

Phosphorylation of Stathmin and its Interaction with PPIL1

Figure 26:
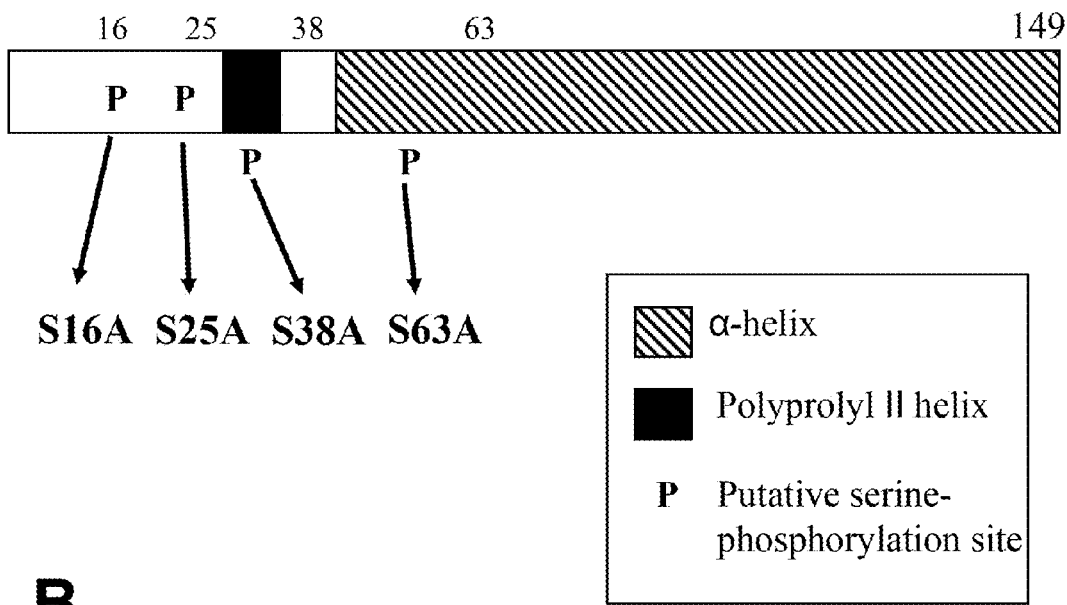
FIGS. 26A and 26B depict the expression and interaction of mutants of stathmin with PPIL1 in vivo.
Figure 26:
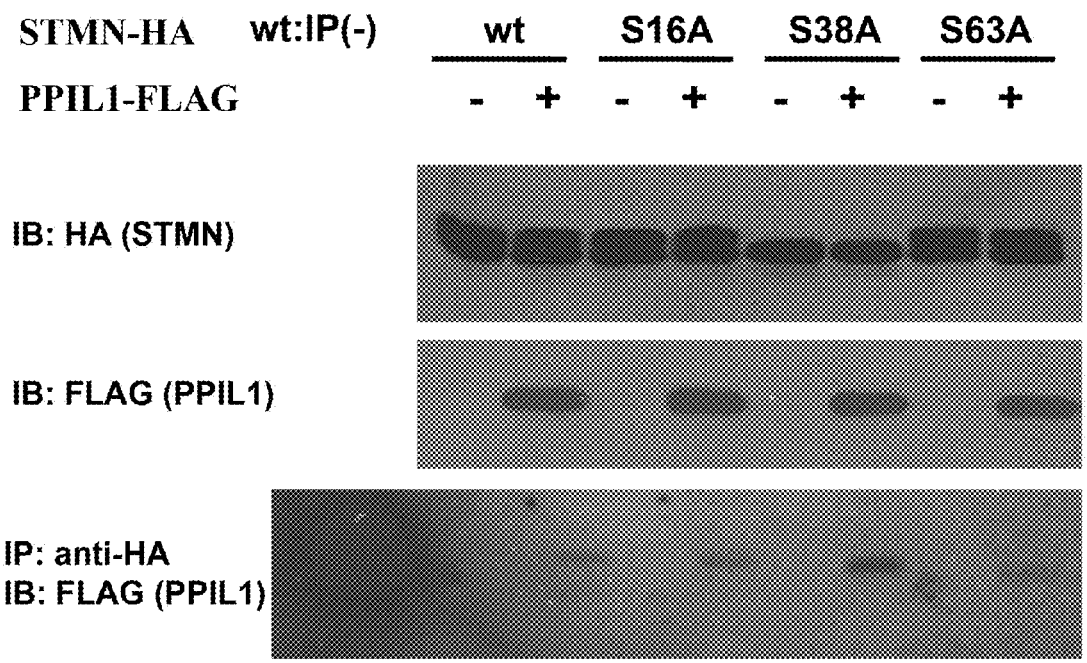

Since immunoprecipitation with anti-Flag antibody showed a single band corresponding to the modified form of stathmin, plasmids expressing its mutated form at the putative serine phosphorylation sites were prepared to test their binding with PPIL1 (FIG. 26A). Specifically, mutants (Ser substituted with Ala) were prepared using QuikChange site-directed mutagenesis kit (Stratagene) and primer sets, 5'-CTGGAGAAGCGTGCCGCAGGCCAGGCTTTTG-3' [SEQ ID NO: 65] and 5'-CAAAAGCCTGGCCTGCGGCACGCTTCTCCAG-3' [SEQ ID NO: 66] for S16A; 5'-GCTTTTGAGCTGATTCTCGCCCCTCGGTCAAAAGAATCTG-3' [SEQ ID NO: 67] and 5'-CAGATTCTTTTGACCGAGGGGCGAGAATCAGCTCAAAAGC-3' [SEQ ID NO: 68] for S25A; 5'-CCAGAATTCCCCCTTGCCCCTCCAAAGAAGAAG-3' [SEQ ID NO: 69] and 5'-CTTCTTCTTTGGAGGGGCAAGGGGGAATTCTGG-3' [SEQ ID NO: 70] for S38A; 5'-CAGAAGAAAGACGCAAGGCCCATGAAGCTGAGG-3' [SEQ ID NO: 71] and 5'-CCTCAGCTTCATGGGCCTTGCGTCTTTCTTCTG-3' [SEQ ID NO: 72] for S63A, according to the supplier's recommendations.

Western blot analysis of cells transfected with S16A, or S63A mutant detected the unphosphorylated and phosphorylated forms, while that with S38A showed a single band corresponding to the unphosphorylated form. Therefore, serine 38 of stathmin is possibly phosphorylated in the cells. Surprisingly, stathmin-S38A mutant was capable to associate with PP1L1 (FIG. 26B). Therefore, interaction of PPIL1 to stathmin may enhance the phosphorylation of the serine 38 that is adjacent to the PPIL1-binding site between codons 44 and 61 of stathmin.

Example 26

Isolation of APCDD1 as a Gene Regulated by APC

Colorectal carcinogenesis involves impaired regulation of β-catenin/Tcf pathway as an early step. Therefore, downstream genes of this pathway were searched in the next procedure. The transduction of APC reduces the level of β-catenin in the nucleus and subsequently represses the transactivating activity of β-catenin/Tcf complex in colon cancer cells (van der Heyden et al., J Cell Sci 111: 1741-9 (1998)). Thus, expression profiles of SW480 cells in which a large amount of β-catenin is accumulated in nuclei and cytoplasm were compared using microarray method similar as in Example 1.

For the identification of genes regulated by β-catenin/Tcf complex, SW480 cells (ATCC, Rockville, Md.) were infected at MOI=100 with adenovirus constructs that express either wild-type APC (Ad-APC) or LacZ (Ad-LacZ; control gene) and cultured in Leibovitz's L-15. 72 h after the infection, total RNA was extracted from the cells, and T7-based RNA amplification was carried out using polyA RNA purified from the extracts according to Satoh et al. (Nat Genet 24: 245-50 (2000)). The amplified RNA (aRNA) from SW480 cells with Ad-APC and Ad-LacZ were labeled with Cy5-dCTP and Cy3-dCTP, respectively, and equal amount thereof were subjected as probes for co-hybridization on microarray slides.

The expression profile of 23040 genes in SW480 cells infected with Ad-APC to that with Ad-LacZ was compared to identify a number of genes whose expression levels were down-regulated by the transfection of APC. Among the genes, a gene with an in-house accession number of B7323N corresponding to an EST, Hs.20665 of UniGene cluster in NCBI (the National Center for Biotechnology Information), whose expression level was decreased approximately 4-fold in response to Ad-APC compared to Ad-LacZ was identified.

Figure 27:
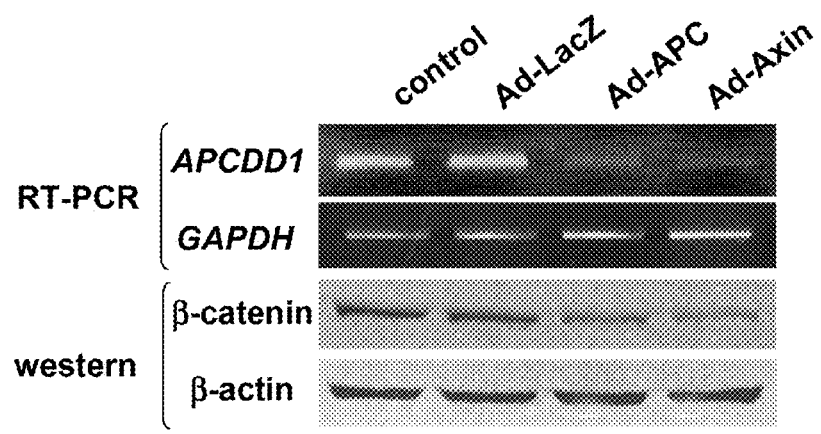
FIGS. 27a to 27c present photographs showing the expression of APCDD1.
Figure 27:
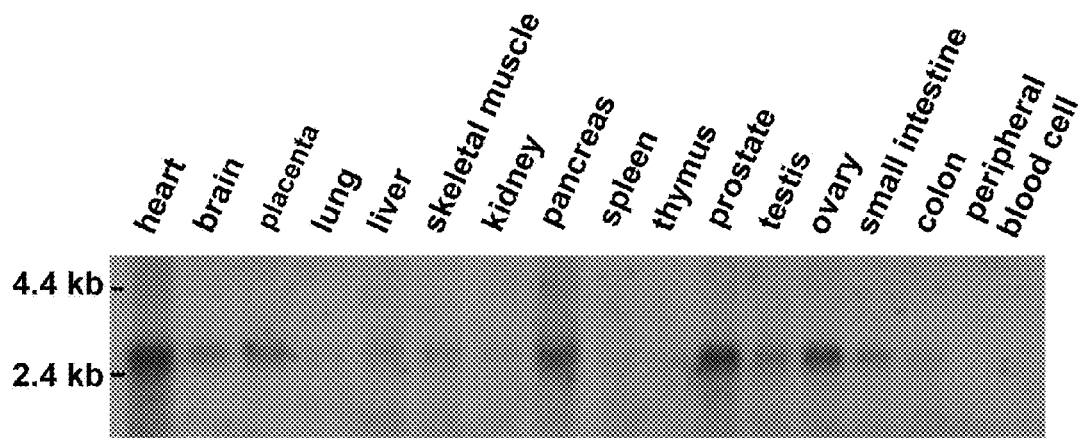
Figure 27:
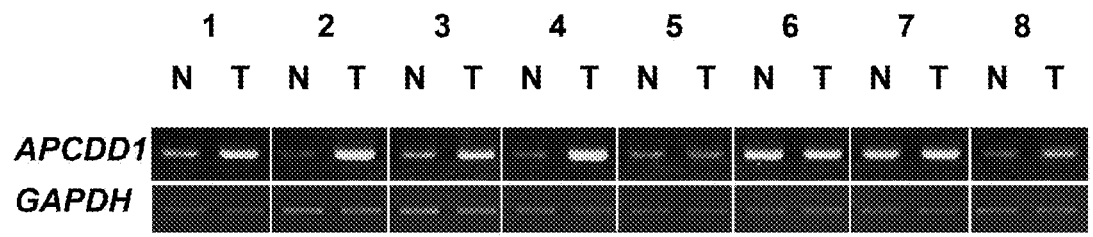

Subsequently, semiquantitative RT-PCR experiment was conducted to confirm the reduced expression of APC (FIG. 27a). Specifically, total RNA was extracted with Qiagen RNeasy kit (Qiagen) or Trizol reagent (Life Technologies, Inc.) according to the manufacturers' protocol. Ten-microgram aliquot of total RNA were reverse transcribed into cDNAs using poly $dT_{12-18}$ primer (Amersham Pharmacia Biotech) with Superscript II reverse transcriptase (Life Technologies). Obtained single-stranded cDNA preparation was diluted in 20 μl of PCR buffer (TaKaRa). Then PCR amplification by standard RT-PCR experiment was conducted using following primers: forward, 5'-GGATCATCTATCGGTCAGACG-3' [SEQ ID NO: 73]; and reverse; 5'-TGGGTCACATCCTGCTGGATG-3' [SEQ ID NO: 74]. The amplification was conducted using GeneAmp PCR system 9700 (Perkin-Elmer, Foster City, Calif.) under following condition: denaturing at 94° C. for 4 min; 30 cycles of 94° C. for 30 s, 56° C. for 30 s, and 72° C. for 45 s.

Furthermore, the cells were also treated with Ad-Axin, adenovirus expressing wild-type AXIN1 that also down-regulated the activity of β-catenin/Tcf-4 complex, and examined for their expression of B7323N. As a consequence, decreased expression of B7323N by the transduction of AXIN1 was observed as well (FIG. 27a).

Homology searches in public databases with the cDNA sequence of B7323N identified over one hundred of ESTs and a human genomic sequence (GenBank Accession number NT_019631) assigned on chromosomal band 18p11.2. To determine the full-length cDNA sequence of B7323N, 5'RACE was carried out as in Example 2 except using a gene-specific primer for B7323N (5'-GCTCGTCTGACCGATAGATGATCC-3' [SEQ ID NO: 75]) and obtained a cDNA sequence. Consequently its full-length cDNA sequence was determined. The cDNA consisted of 2607 nucleotides with an open reading frame of 1542 nucleotides encoding a putative 514-amino acid protein with a predicted molecular weight of 58.8 kD (GenBank accession No. AB104887). The predicted APCDD1 protein had 31% identity with the endo-1,4-beta-xylanase of *Thermobacillus xylanilyticus*. Motif searches using the computer programs SMART (see smart/embl-heidelberg/de/) and PSORT II Prediction (see psort.nibb.ac.jp/form2.html) did not identify any known domains in the databases. Therefore this gene was dubbed APCDD1 (down-regulated by APC 1). Comparison of the cDNA sequences with the genomic sequence allowed determining the genomic structure of APCDD1, which consisted of 5 exons and approximately covered a 40-kb genomic region (data not shown). The determined nucleotide sequence of APCDD1 and its predicted amino acid sequence are shown in SEQ ID NOs: 7 and 8, respectively Finally, Northern blot analysis was conducted as in Example 2 for APCDD1. The Northern blot analysis demonstrated that a 2.6-kb transcript of APCDD1 was expressed abundantly in heart, pancreas, prostate, and ovary but scarcely expressed in lung, liver, kidney, spleen, thymus, colon, and peripheral leukocytes (FIG. 27b).

Example 27

Expression of APCDD1 in Colon-Cancer Tissues

Since the accumulation of β-catenin is a frequent feature of colorectal tumors, the expression of APCDD1 in colon-cancer and corresponding non-cancerous tissues was examined by semiquantitative RT-PCR as in Example 26 to detect an increased expression in 20 (67%) of 30 tumors examined (FIG. 27c). This result was consistent with the fact that APCDD1 is up-regulated in response to activation of the β-catenin/Tcf transcriptional complex.

Example 28

Figure 28:
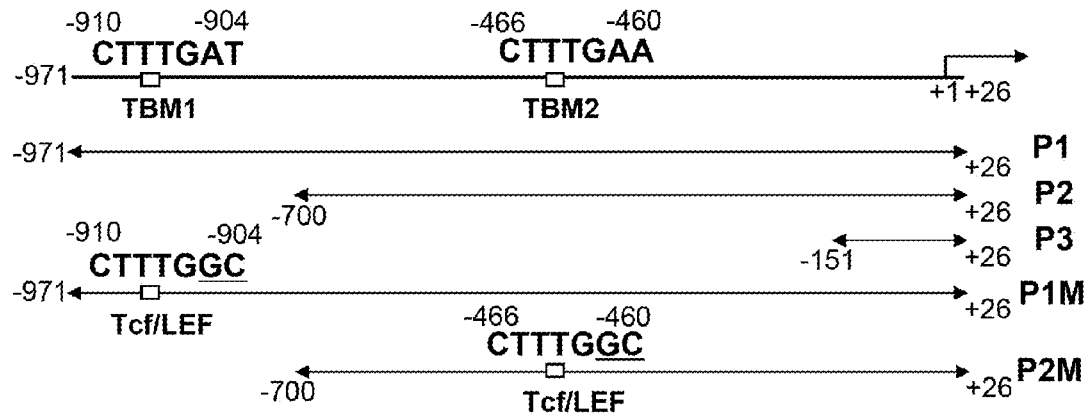
FIG. 28 depicts the result of reporter assay performed using various plasmids of APCDD1.
Figure 28:
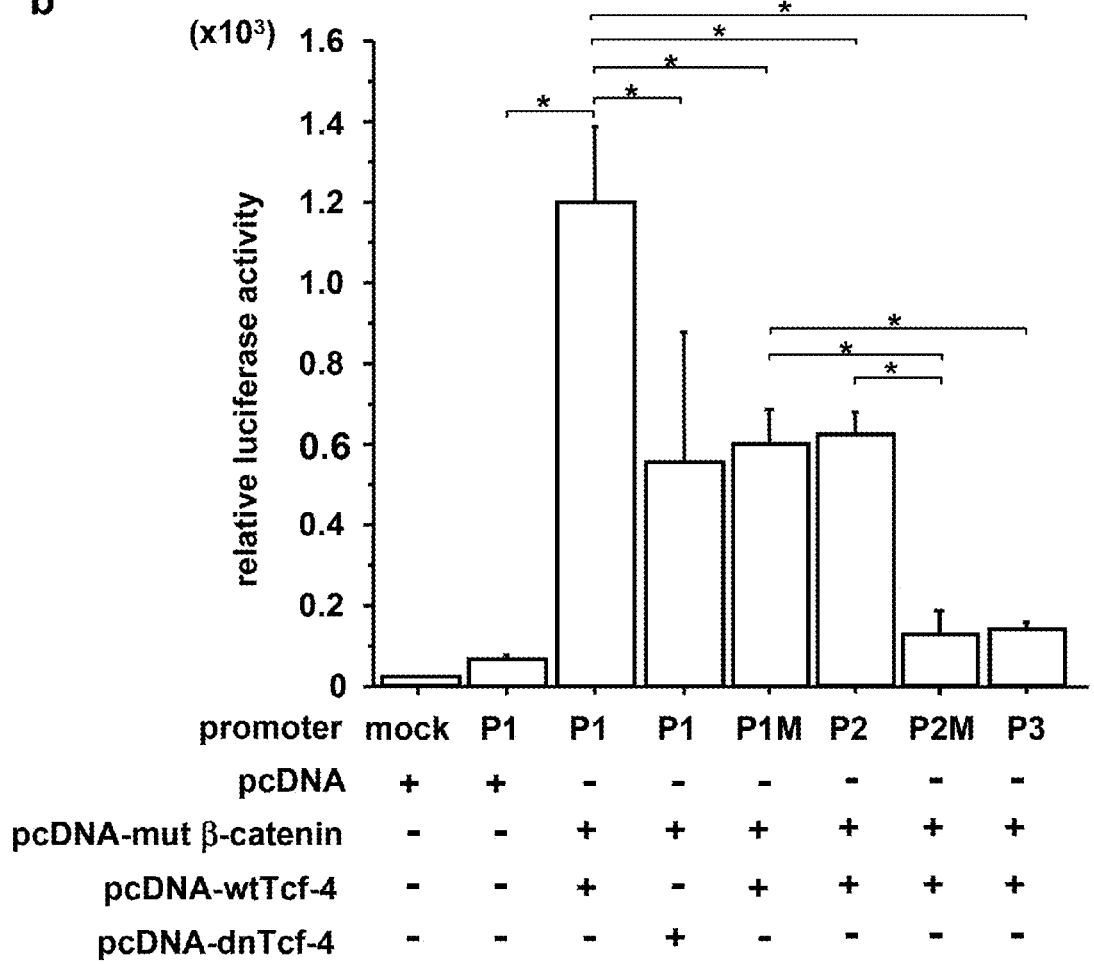

Promoter Activity of APCDD1 is Up-Regulated by β-Catenin and Wild-Type Tcf4 Complex To test whether the promoter activity of APCDD1 is regulated by β-catenin/Tcf4 complex, reporter plasmid P1 containing two putative Tcf/LEF binding motifs (TBM1 and 2) with/without an activated form of mutant β-catenin and wild-type Tcf4 were transfected into HeLa cells (FIG. 28a). More specifically, a putative transcriptional initiation site (TIS) of APCDD1 was determined by a comparison between a human genomic sequence (GenBank accession No. NT_019631.4) and the sequence of APCDD1 cDNA. Three fragments of the 5' flanking region of APCDD1 were amplified by PCR (P1, P2, and P3), and cloned into an appropriate enzyme site of pGL3-Basic vector (Promega). Site directed mutagenesis were performed using QuickChange™ Site-Directed Mutagenesis Kit (STRATAGENE) for P1 and P2 that contained one or two putative Tcf/LEF binding motifs. An activated form of mutant β-catenin was prepared by RT-PCR using a set of primers, 5'-AAGGATCCGCGTGGACAATG-GCTACTCAAG-3' [SEQ ID NO: 76] and 5'-GGACTC-GAGACAGGTCAGTATCAAACCAGGCCAG-3' [SEQ ID NO: 77] and RNA extracted from HCT116 colon cancer cells as a template, and subsequently cloned into an appropriate cloning site of pcDNA3.1 plasmid vector (Invitrogen). Human cDNA fragments of the entire coding region and its 5'deleted region of Tcf-4 (wtTcf4, dnTcf4) were amplified by RT-PCR using sets of primers TcfF1: 5'-AAGAATTCT-GCTGGTGGGTGAAAAAAAAATGC-3' [SEQ ID NO: 78] and TcfR1: 5'-CTACTCGAGTTCTAAAGACTTGGTGAC-GAGCGAC-3' [SEQ ID NO: 79], and TcfF3: 5'-AGGAAT-TCGTGCATCATGGTCCCACCACATCATAC-3' [SEQ ID NO: 80] and TcfR1, respectively. The products were also cloned into the pcDNA3.1 plasmid vector. Two μg of each reporter plasmid and 1.5 μg of each of the expression constructs were co-transfected with 0.5 μg of pRL-TK plasmid (Promega) into HeLa cells using FuGENE6 (Boehringer Mannheim) to normalize the efficiency of transfection. Reporter assay was carried out using a Dual-Luciferase Reporter Assay System according to the supplier's recommendations (Promega).

The reporter activity of plasmid P1 was significantly enhanced by the introduction of the activated form of β-catenin and wild-type Tcf4 (FIG. 28b). Interestingly, the enhanced activity was reduced when P1 was co-transfected with the dominant-negative form of Tcf4, suggesting that Tcf4 affected the promoter activity of APCDD1.

To determine the element(s) responsible for its promoter activity, the promoter activity for each of the various deletion mutants of P1 was further compared. The activity of P1 was significantly higher than that of P2 and P3 respectively, and the activity of P2 containing only TBM2 was significantly higher than that of P3 (FIG. 28b). These data suggested that a region encompassing −971 and −151 may associate with the β-catenin/Tcf4 complex, and is involved in the APCDD1 promoter activity. Since this region contained two possible Tcf/LEF-binding motifs, these motifs were hypothesized to be responsible for the transcriptional activation.

To investigate this hypothesis, reporter plasmids P1M and P2M, in which the candidate Tcf/LEF-binding motif was changed to CTTTGGC [SEQ ID NO: 81] to which β-catenin/Tcf4 complex was unable to bind were constructed. Reporter assay using these five plasmids revealed that the P1M and P2M fragment containing the mutated motif had decreased ability to activate transcription of APCDD1; and its luciferase activity was equivalent to that of the P2 or P3 fragment (FIG. 28b). These results imply that both the putative Tcf/LEF-binding motifs are involved in transcriptional activation of APCDD1.

Example 29

Electrophoretic Mobility Shift Assay

In order to examine whether the β-catenin/Tcf4 complex associates directly with TBM1 and TBM2, an electrophoretic mobility shift assay (EMSA) was carried out using oligonucleotides designed to encompass the TBM1 sequence (APCDD1-TBM1) and the TBM2 sequence (APCDD1-TBM2). Specifically, EMSA was performed using extracts from intact nuclei of SW480 cells as previously described (van der Heyden et al., J Cell Sci 111: 1741-9 (1998)). Two double-stranded 16-nucleotide DNA probes were prepared by annealing FF (5'-GCTTTGATTGTGGTGA-3' [SEQ ID NO: 82]) and RR (5'-TCACCACAATCAAAGC-3' [SEQ ID NO: 83]) for APCDD1-TBM1, and FF2 (5'-CCCCTTTGAA-CACCTT-3' [SEQ ID NO: 84]) and RR2 (5'-AAGGTGT-TCAAAGGGG-3' [SEQ ID NO: 85]) for APCDD1-TBM2.

Figure 29:
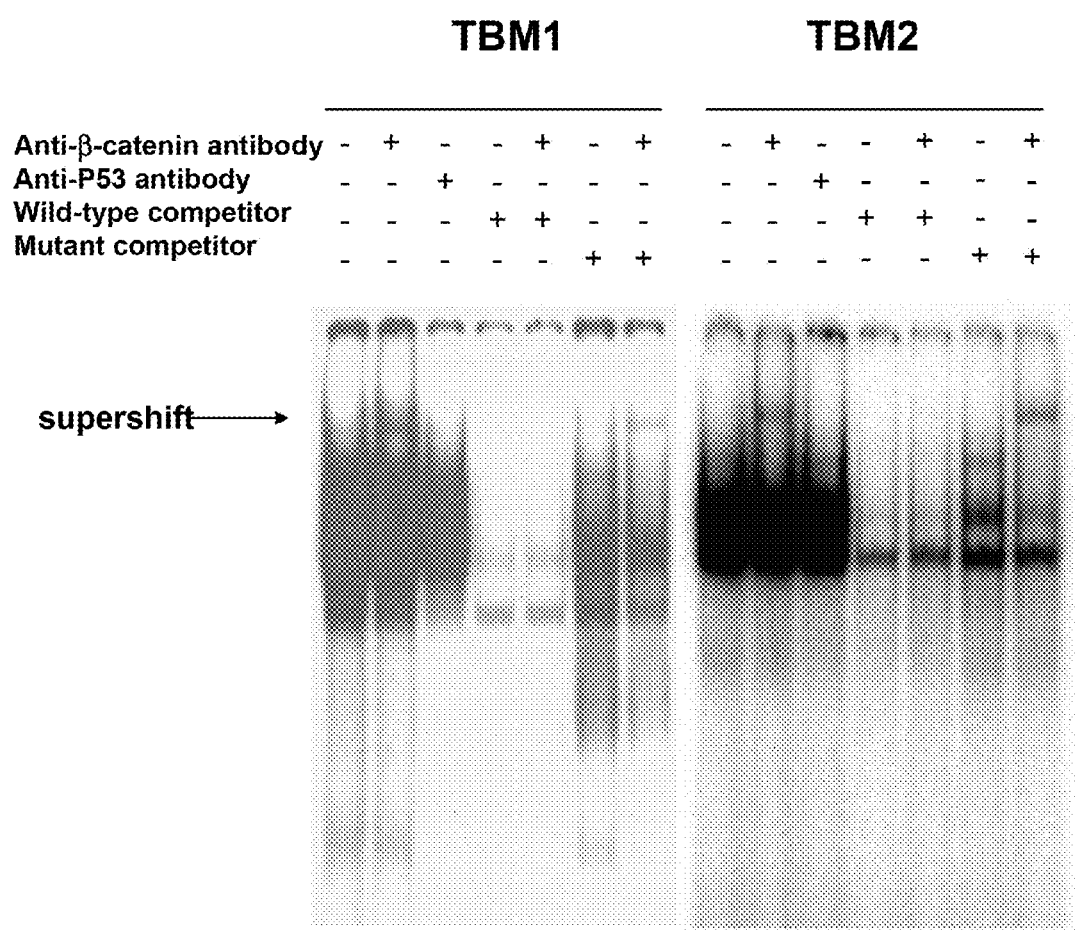
FIG. 29 is a photograph depicting the result of EMSA showing the interaction between elements containing either TBM1 or TBM2 and the β-catenin/Tcf4 complex. A supershift of the band representing the complex was observed after the addition of anti-β-catenin antibody (Lane 2) but not with anti-P53-antibody (Lane 3). Bands corresponding to Tcf4-probe and β-catenin/Tcf4-probe were blocked specifically by the addition of non-labeled wild-type probe (Lane 5).

A shift in the band corresponding to the binding of β-catenin/Tcf4 to both APCDD1-TBM1 and APCDD1-TBM2 was observed by the addition of anti-β-catenin antibody, but not by P53 antibody (control) (FIG. 29). As expected, this binding was abrogated by addition of wild-type unlabelled oligonucleotides, but not by mutant unlabelled oligonucleotides.

Example 30

Effect of APCDD1 on Cell Growth in LoVo Cells In Vitro

To disclose a potential role of APCDD1 in colorectal tumorgenesis, plasmids expressing APCDD1 (pcDNA-APCDD1) and complementary strand of APCDD1 (pcDNA-antisense) were prepared to carry out a colony formation assay in LoVo cells (ATCC, Rockville, Md.) expressing low amount of APCDD1. More specifically, the entire coding region of APCDD1 was amplified by RT-PCR using gene specific primer set: 5'-GCGGAATTCAGGGCCCAGAG- CAGGACTG-3' [SEQ ID NO: 86] and 5'-TAGCTC-GAGCTAAAACTTCTATCTGCGGATGT-3' [SEQ ID NO: 87]. The PCR product was cloned into appropriate cloning site of pcDNA3.1 (Invitrogen). Then, LoVo cells were transfected with either the constructed pcDNA-APCDD1 or pcDNA-antisense, and the cells were incubated in HAM's F-12 supplemented with an appropriate concentration of geneticin for 10 to 21 days. The cells were fixed with 100% methanol and stained with Giemsa solution.

Figure 30:
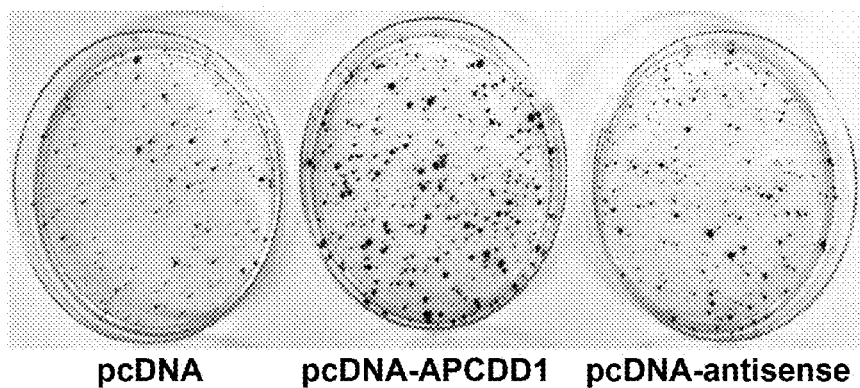
FIG. 30 depicts the effect of APCDD1 on cell growth in LoVo cells in vitro.
Figure 30:
Figure 30:
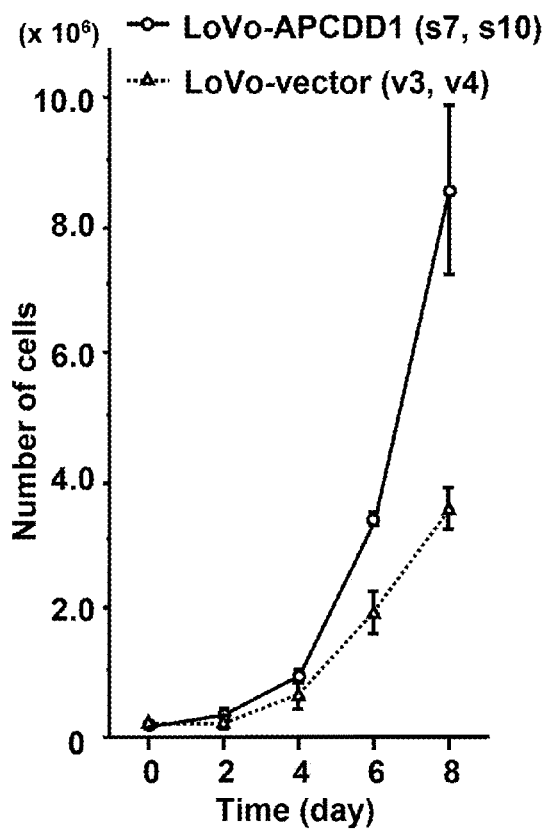
Figure 30:
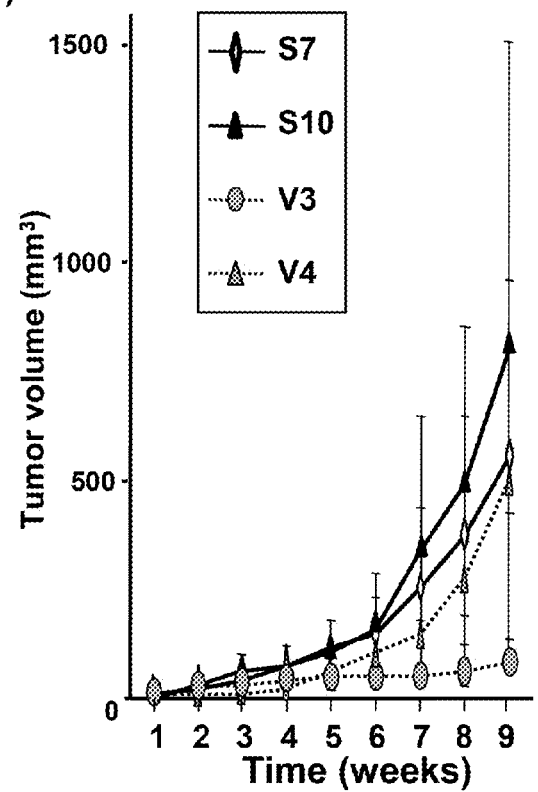

As a result, compared with control plasmids pcDNA-antisense or pcDNA, pcDNA-APCDD1 produced markedly more colonies (FIG. 30a). This result was confirmed by three independent experiments. To corroborate its effect on cell growth in vitro, LoVo cells expressing exogenous APCDD1 (LoVo-APCDD1 cells) were established to compare their growth with control cells transfected with mock vector (FIG. 30b). LoVo-APCDD1 cells grew at a markedly increased rate compared to the control LoVo-mock cells (FIG. 30c).

Example 31

Effect of APCDD1 on Tumor Growth in Nude Mice

To investigate roles of APCDD1 in vivo, either two clones of LoVo-APCDD1 cells or two clones of LoVo-mock cells were subcutaneously transplanted into 12 BALBcAnN Crj-nu/nu mice. Specifically, tumor cells, LoVo-APCDD1 or LoVo-vector, were adjusted to a final concentration of $5 \times 10^7$ cells/ml, and 100 µl were injected s.c. into the posterior mid-dorsum of BALB/cAnN Crj-nu/nu mice respectively. Tumors were measured every 7 days for 8 weeks, and the volumes were estimated by the formula $V=\pi/6 \times a^2 \times b$, where "a" is the short axis, and "b" the long axis.

As a result, the average sizes of tumors of LoVo-APCDD1 clones reached sizes of approximately 482 and 653 mm$^3$ while those of LoVo-mock were 65 and 277 mm$^3$ eight weeks after the transplantation; indicating that the introduction of APCDD1 renders growth promoting effect on cells in vivo (FIG. 30d).

Example 32

Growth-Inhibitory Effect of Antisense S-Oligonucleotides Designated to Reduce Expression of APCDD1

To assess the growth-promoting role of APCDD1, various pairs of control and antisense S-oligonucleotides corresponding to APCDD1 were synthesized to transfect them into SW480 cells, which expressed abundant amount of APCDD1 among examined 11 colon cancer cell lines. The method was conducted following the procedures described in Example 5 except SW480 cells were used in place of SNU475 cells, and following S-oligonucleotides were used: control sense S-oligonucleotide APCDD1-S2, 5'-ATGTCCTGGCCGCGCC-3' [SEQ ID NO: 88]; antisense S-oligonucleotide APCDD1-AS2, 5'-GGCGCGGCCAGGACAT-3' [SEQ ID NO: 89]; reverse S-oligonucleotide APCDD1-R2, 5'-TACAGGAC-CGGCGCGG-3' [SEQ ID NO: 90]; and scrambled S-oligonucleotides APCDD1-Sc2 5'-ATCTGGTCCGGCGCGG-3' [SEQ ID NO: 91].

Figure 31:
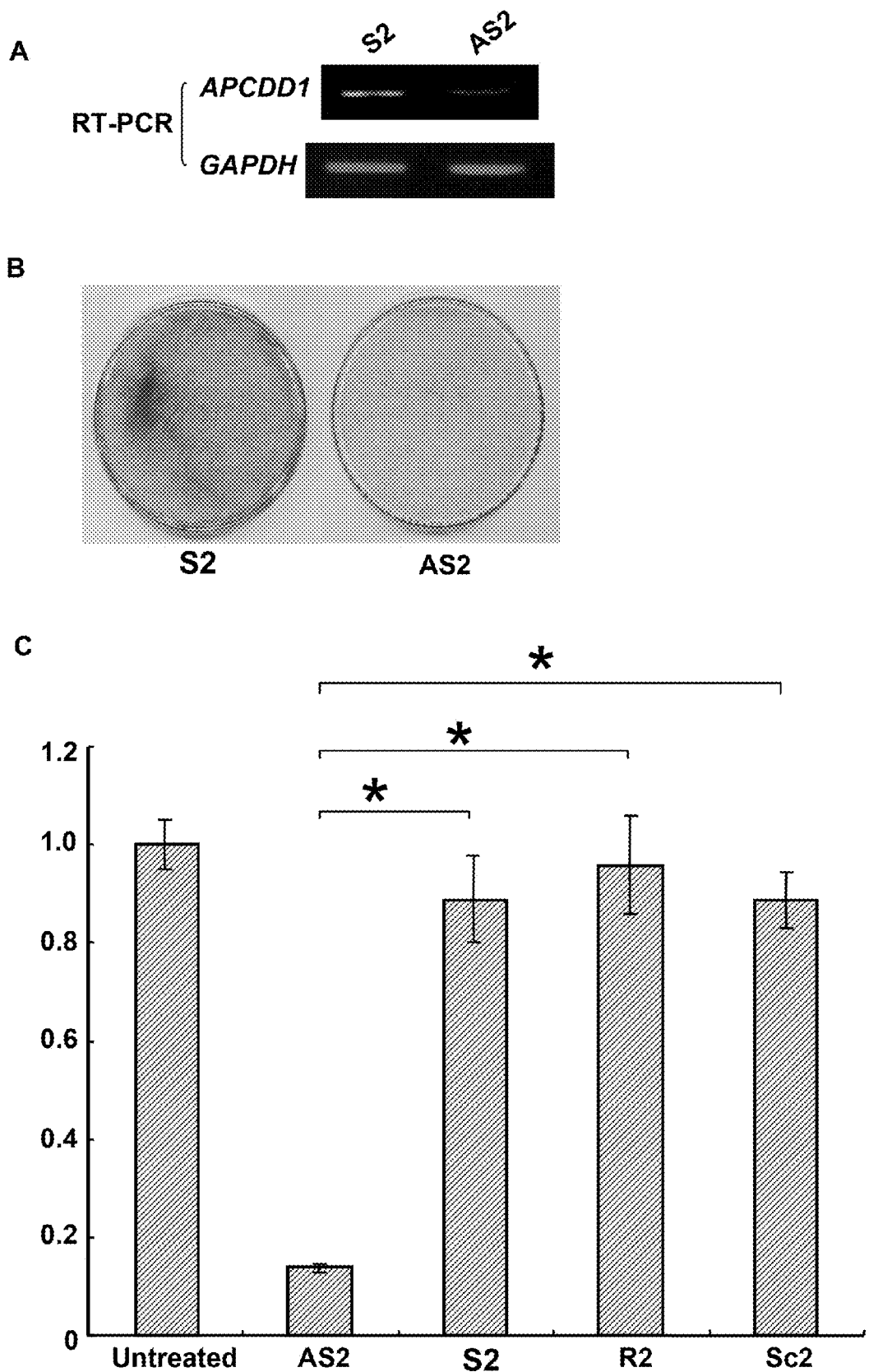
FIGS. 31A to 31C depict the growth inhibitory effect of antisense S-oligonucleotides designated to reduce the expression of APCDD1.

Among the oligonucleotides, APCDD1-AS2 significantly suppressed the expression of APCDD1 compared to control APCDD1-S1 in the cells (FIG. 31a). Interestingly, six days after transfection, introduction of APCDD1-AS2 clearly suppressed focus formation of the cells, compared with APCDD1-S2, suggesting that suppression of APCDD1 reduces growth and/or survival of transfected cells (FIG. 31b). MTT assay confirmed decreased cell survival in response to APCDD1-AS2 compared to APCDD1-R2, APCDD1-Sc2, and untreated cells (FIG. 31c).

Example 33

Expression of APCDD1 in Colon Cancer Cell Lines

To examine the expression and function of APCDD1, polyclonal antibody against APCDD1 was prepared as follows. First, recombinant His-tagged APCDD1 protein was produced in E. coli and purified from the cells using Pro Bond™ histidine Resin (Invitrogen) according to the manufacturer's recommendations. The recombinant protein was used for the immunization of rabbits. The polyclonal antibody against APCDD1 was purified from the sera. For western blot analysis, proteins were separated by 10% SDS-PAGE and immunoblotted with anti-APCDD1 antibody. HRP-conjugated goat anti-rabbit IgG (Santa Cruz Biotechnology) served as the secondary antibody for the ECL Detection System (Amersham Pharmacia Biotech).

Figure 32:
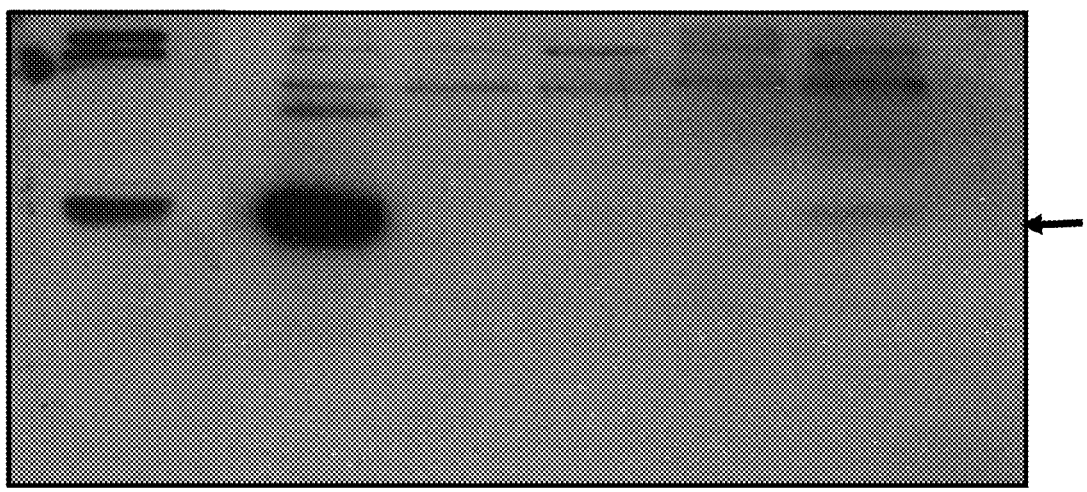
FIG. 32 is a photograph demonstrating the result of Western blot analysis of COS7 cells transfected with APCDD1 and with or without pFLAG-APCDD1, and colon cancer cell lines.

Immunohistochemical staining of SW480 cells and frozen tissues was also carried out as described in Example 18 using anti-APCDD1 antibody. Paraffin-embedded tissue sections were subjected to the SAB-PO peroxidase immunostaining system (Nichirei, Tokyo, Japan) according to the manufacturer's recommended method. Antigens were retrieved from deparaffinized and re-hydrated tissues by pre-treating the slides in citrate buffer (pH6) in a microwave oven for 10 min at 700 W. Western blot analysis with anti-APCDD 1 antibody using extracts of colon cancer cells, including HCT116, SNUC4, and SW480 showed 58-kDa bands corresponding to APCDD1 (FIG. 32). The size of endogenous APCDD1 protein was quite similar to that of exogenous Flag-tagged APCDD1 protein detected with anti-FLAG antibody. The expression of APCDD1 was most abundant in SW480 cells among the three colon cancer cell lines.

Example 34

Subcellular Localization of APCDD1 in Colon Cancer Cells and Tissues

Figure 33:
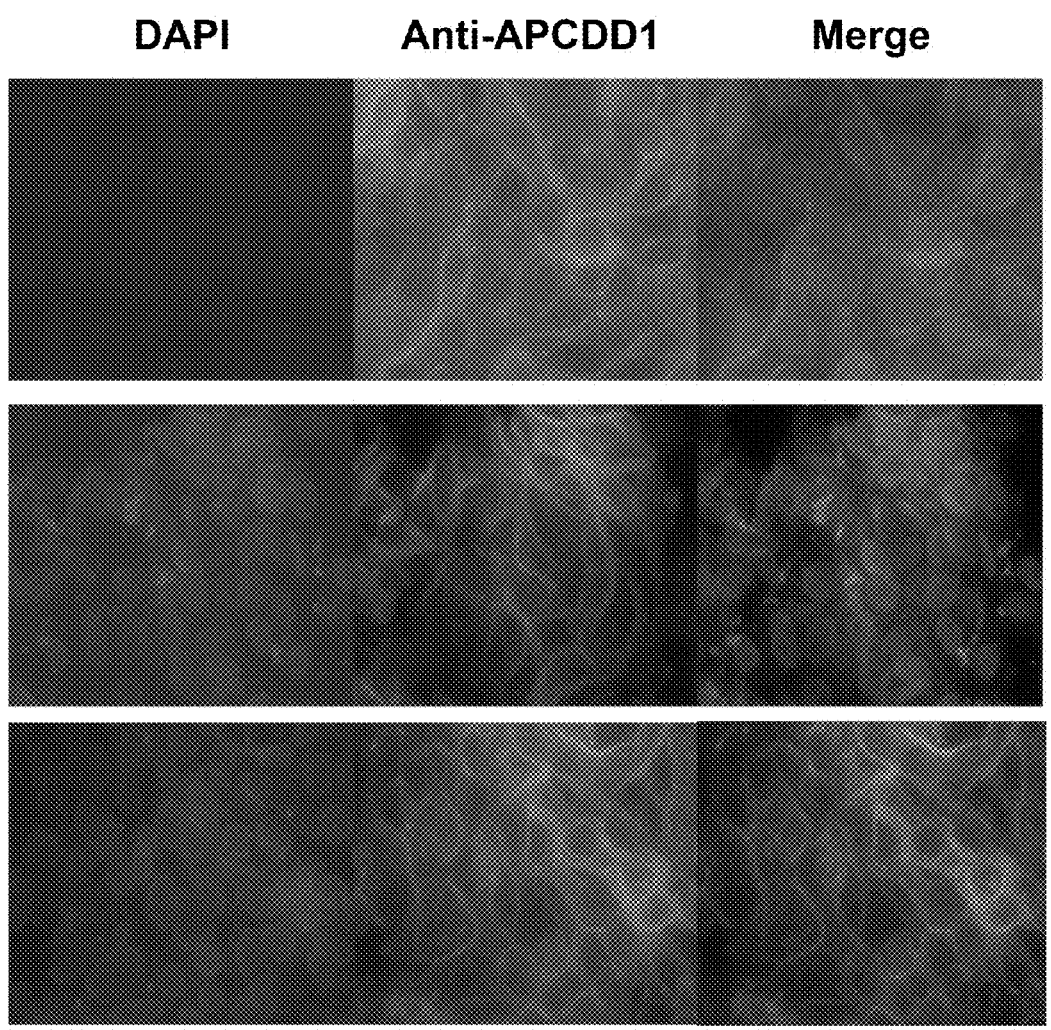
FIG. 33 presents photographs depicting the subcellular localization of APCDD1 protein in SW480 cells.

To investigate its subcellular localization, fluorescent immunohistochemical staining of APCDD1 was carried out using SW480 cells. Cells were fixed, stained with anti-APCDD1, and visualized with fluorescein conjugated secondary antibody. Signals were observed at the cell-to-cell boundaries and cytoplasms (FIG. 33).

Figure 34:
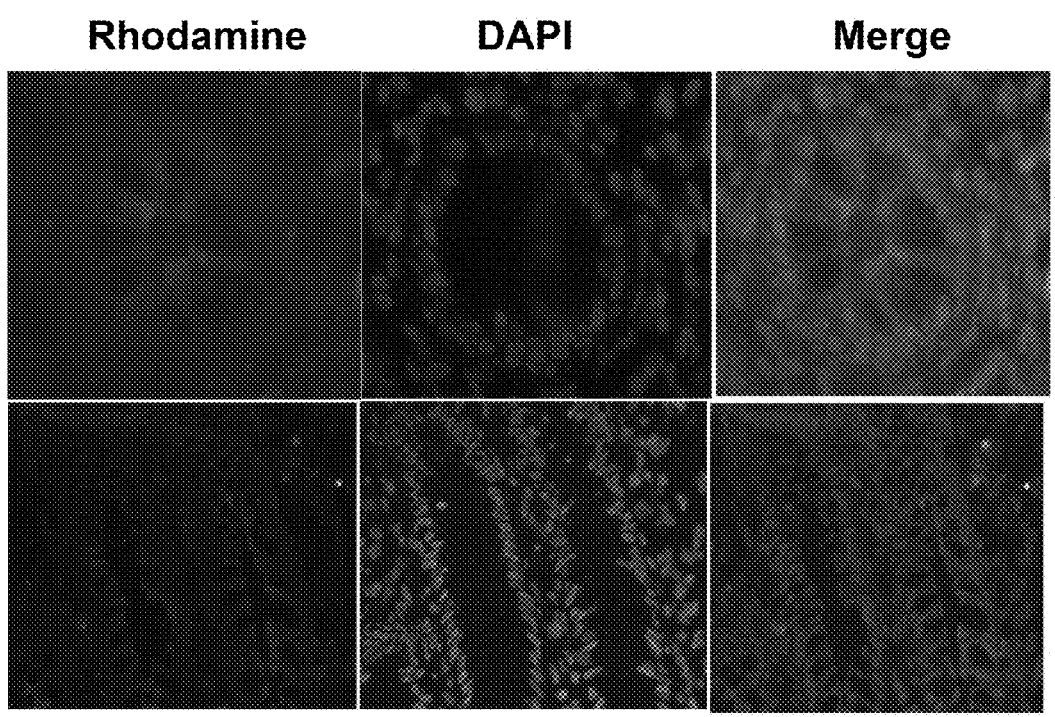
FIG. 34 presents photographs depicting the result of fluorescent immunohistochemical staining of APCDD1 in non-cancerous mucosa (A) and adenocarcinoma (B) of the colon.
Figure 34:
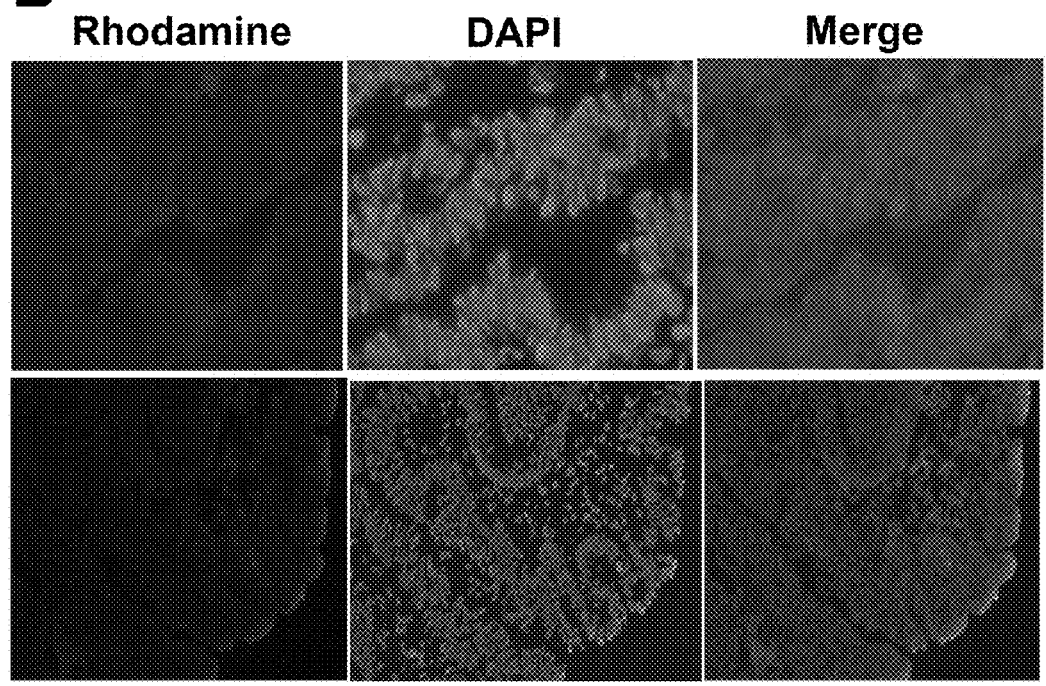

APCDD1 expression in non-cancerous colonic mucosae and carcinoma tissues were also investigated and staining were revealed in the cytoplasms of the non-cancerous and cancerous cells (FIG. 34). Notably, strong signals were observed at the apical boarder of epithelial cells.

Example 35

Figure 35:
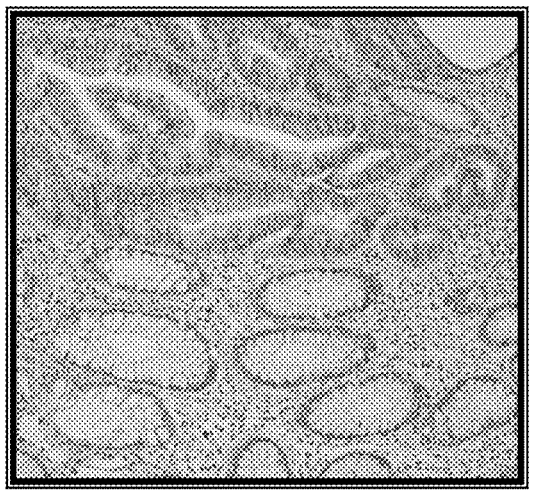
FIG. 35 presents photographs depicting the result of immunohistochemical staining of APCDD1 in colon cancer tissues.
Figure 35:
Figure 35:
Figure 35:
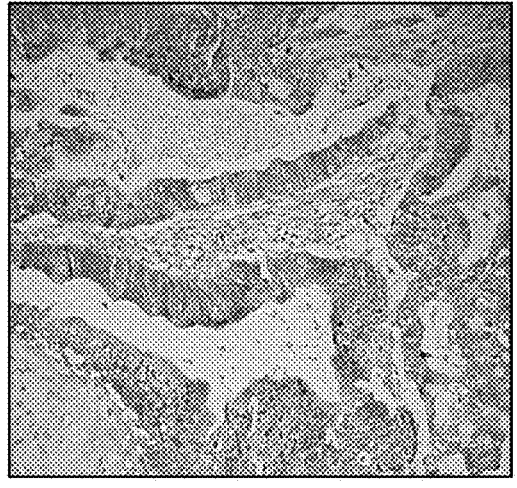
Figure 36:
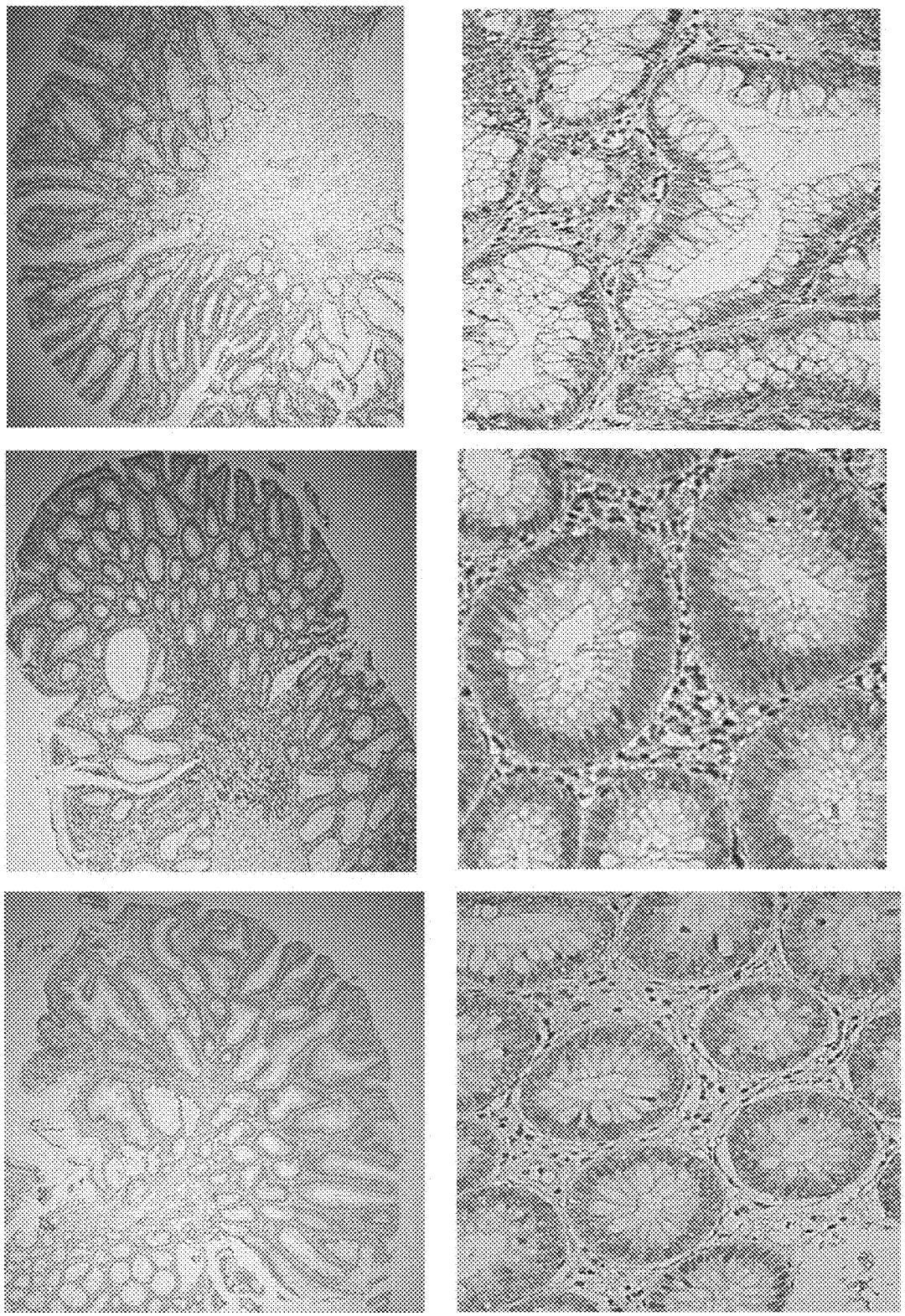
FIG. 36 presents photographs depicting the result of immunohistochemical staining of APCDD1 in adenomas of colon.

Expression of APCDD1 in Normal Epitheria, Adenocarcinomas, and Adenoma of the Colon To compare the expression levels of APCDD1 protein between non-cancerous epitherial cells and tumor cells, paraffin-embedded tissues were subjected to immunohistochemical staining. Cancerous cells were more strongly stained with anti-APCDD1 antibody than non-cancerous epithelial cells (FIG. 35). In addition, weak signals were also observed in adenoma cells (FIG. 36).

INDUSTRIAL APPLICABILITY

The expression of novel human genes WDRPUH and KRZFPUH is markedly elevated in hepatocellular carcinoma as compared to non-cancerous liver tissues. On the other hand, the expression of novel human genes PPIL1 and APCDD1 is markedly elevated in colon cancer cells as compared to non-cancerous tissues. Accordingly, these genes may serve as a diagnostic marker of cancer and the proteins encoded thereby may be used in diagnostic assays therefore.

The present inventors have also shown that the expression of novel protein WDRPUH, KRZFPUH, PPIL1, or APCDD1 promotes cell growth whereas cell growth is suppressed by antisense oligonucleotides or siRNAs corresponding to the WDRPUH, KRZFPUH, PPIL1, or APCDD1 gene. These findings suggest that WDRPUH, KRZFPUH, PPIL1, or APCDD1 protein stimulates oncogenic activity. Thus, this novel oncoprotein is a useful target for the development of anti-cancer pharmaceuticals. For example, agents that block the expression of WDRPUH, KRZFPUH, PPIL1, or APCDD1 or prevent its activity may find therapeutic utility as anti-cancer agents, particularly anti-cancer agents for the treatment of HCC and colon cancer. Examples of such agents include antisense oligonucleotides, siRNAs, and antibodies that recognize WDRPUH, KRZFPUH, PPIL1, or APCDD1.

Furthermore, the present inventors have shown that PPIL1 directly associates with stathmin, which result suggests the ability of PPIL1 to enhance phosphorylation of stathmin in vivo. Since stathmin is reported to be involved in the progression of cell cycle and linked to various types of cancer, agents that inhibit the activity of the complex may also find utility in the treatment and prevention of colorectal cancer.

Moreover, the binding of β-catenin/Tcf-4 complex to the two Tcf/LEF binding motifs of APCDD1 was demonstrated to be involved in the transcriptional activation of APCDD1 by the present invention. Thus, agents that inhibit the binding of the complex to the binding motif may also find utility in the treatment and prevention of colorectal cancer.

While the invention has been described in detail and with reference to specific embodiments thereof, it will be apparent to one skilled in the art that various changes and modifications can be made therein without departing from the spirit and scope of the invention.

The invention claimed is:

1. A method for diagnosing a hepatocellular carcinoma, said method comprising the steps of:
   (a) detecting the expression level of the gene encoding the amino acid sequence of SEQ ID NO: 2 in a biological sample comprising liver tissue(s) or liver cell(s), wherein the expression level is detected by detecting the mRNA encoding the amino acid sequence of SEQ ID NO: 2 or the protein comprising the amino acid sequence of SEQ ID NO: 2; and
   (b) comparing the expression level detected in step (a) with that in a normal sample, where a higher than normal expression level is indicative of hepatocellular carcinoma.

* * * * *